(12) United States Patent
Baerson et al.

(10) Patent No.: US 9,248,145 B2
(45) Date of Patent: Feb. 2, 2016

(54) TWO ALKYLRESORCINOL SYNTHASE GENES FROM SORGHUM; CLONING, EXPRESSION, TRANSFORMATION AND CHARACTERIZATION

(75) Inventors: Scott R. Baerson, Oxford, MS (US); Zhiqiang Pan, Oxford, MS (US); Agnes M. Rimando, Oxford, MS (US); Franck E. Dayan, Oxford, MS (US); Daniel Cook, Providence, UT (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 853 days.

(21) Appl. No.: 12/721,206

(22) Filed: Mar. 10, 2010

(65) Prior Publication Data
US 2011/0225676 A1    Sep. 15, 2011

(51) Int. Cl.
| | | |
|---|---|---|
| C12N 5/14 | (2006.01) | |
| A01H 5/00 | (2006.01) | |
| A61K 31/713 | (2006.01) | |
| C12N 9/00 | (2006.01) | |
| C12N 15/82 | (2006.01) | |

(52) U.S. Cl.
CPC ............ *A61K 31/713* (2013.01); *C12N 9/00* (2013.01); *C12N 15/825* (2013.01); *C12N 15/8242* (2013.01); *C12N 15/8257* (2013.01); *C12N 15/8279* (2013.01)

(58) Field of Classification Search
USPC .......................................................... 800/278
See application file for complete search history.

(56) References Cited

U.S. PATENT DOCUMENTS

| 7,202,397 | B2 * | 4/2007 | Conceicao et al. ........... 800/298 |
|---|---|---|---|
| 2004/0031072 | A1 * | 2/2004 | La Rosa et al. ............... 800/278 |
| 2009/0094717 | A1 * | 4/2009 | Troukhan et al. ............. 800/290 |

OTHER PUBLICATIONS

Austin and Noel, The Chalcone Synthase Superfamily of Type III Polyketide Synthases, 20 Nat. Prod. Rep. 79-110 (2003).*
NCBI Accession No. XM$_{13}$002449699 [online], [retrieved on Nov. 2, 2012], retrieved from the internet <http://www.ncbi.nlm.nih.gov/nuccore/XM_002449699.1>.*
Baerson et al., A Functional Genomics Investigation of Allelochemical Biosynthesis in Sorghum bicolor Root Hairs, 283 J. Bio. Chem. No. 6, 3231-3247 (2008).*
Dayan et al., Elucidation of the Biosynthetic Pathway of the Allelochemical Sorgoleone Using Retrobiosynthetic NMR Analysis, 278 J. Bio. Chem. No. 31, 28607-28611 (2003).*
Cook et al., Alkylresorcinol Synthases Expressed in Sorghum bicolor Root Hairs Play an Essential Role in the Biosynthesis of the Allelopathic Benzoquinone Sorgoleone, 22 The Plant Cell, 867-887 (2010).*
Friedberg, Automated protein function prediction-the genomic challenge, 7 Briefings in Bioinformatics, 225-242 at p. 231, top right col. (2006).*
NCBI CDD cd00831 [online], [retrieved on Oct. 19, 2012], retrieved from the internet <http://www.ncbi.nlm.nih.gov/Structure/cdd/cddsrv.cgi?uid=29418>.*
NCBI Accession No. XM_02449699 ([online], [retrieved on Nov. 9, 2012], retrieved from the internet <http://www.ncbi.nlm.nih.gov/nuccore/XM_002449699.1> (hereinafter XM_002449699) submitted Sep. 27, 2008; of record).*
SCORE information for SEQ ID No. 633 of 12286964 published as Troukhan et al. US PG Pub No. 2009/0094717 on Apr. 9, 2009.*
SCORE information for SEQ ID No. 634 of 12286964 published as Troukhan et al. US PG Pub No. 2009/0094717 on Apr. 9, 2009.*
SCORE information for SEQ ID No. 635 of 12286964 published as Troukhan et al. US PG Pub No. 2009/0094717 on Apr. 9, 2009.*
SCORE information for SEQ ID No. 636 of 12286964 published as Troukhan et al. US PG Pub No. 2009/0094717 on Apr. 9, 2009.*

* cited by examiner

*Primary Examiner* — David H Kruse
*Assistant Examiner* — Jason Deveau Rosen
(74) *Attorney, Agent, or Firm* — John D. Fado; Evelyn M. Rabin

(57) ABSTRACT

Sorghum is considered an allelopathic crop species and sorgoleone likely accounts for much of its allelopathic properties. Prior investigations into the biosynthesis of sorgoleone suggested the participation of one or more alkylresorcinol synthases (ARS), which are type III polyketide synthases (PKS) that produce 5-alkylresorcinols using medium to long-chain fatty acyl-CoA starter units via iterative condensations with malonyl-CoA. Quantitative real-time RT-PCR analysis of PKS-like sequences mined from isolated root hairs revealed that two sequences, designated ARS1 and ARS2, were preferentially expressed. Recombinant enzyme studies demonstrated that both sequences encode ARS enzymes capable of accepting a variety of fatty acyl-CoA starter units. RNA interference (RNAi) experiments directed against ARS1 and ARS2 resulted in the generation of multiple independent transformant events exhibiting dramatically reduced sorgoleone levels. Thus, both ARS1 and ARS2 participate in the biosynthesis of sorgoleone in planta. ARS1 and ARS2 sequences were used to identify rice genes encoding alkylresorcinol synthases.

5 Claims, 13 Drawing Sheets
(3 of 13 Drawing Sheet(s) Filed in Color)

TWO ALKYLRESORCINOL SYNTHASE GENES FROM SORGHUM; CLONING, EXPRESSION, TRANSFORMATION AND CHARACTERIZATION

BACKGROUND OF THE INVENTION

1. Field of the Invention

This invention relates to two alkylresorcinol synthase genes cloned from sorghum, the sorghum alkylresorcinol synthase 1 gene, ARS1, and the alkylresorcinol synthase 2 gene, ARS2; constructs containing the ARS1 gene or the ARS2 gene and its promoter; a vector containing a ARS1 or ARS2 gene; ARS1 and ARS2 protein; a method of making ARS1 and ARS2 protein; a method of transforming plants; and transgenic plants which express ARS1 or ARS2 resulting in the biosynthesis of alkylresorcinol precursors to sorgoleone in planta, RNAi constructs, and a method of blocking the production of sorgoleone through RNA interference.

2. Description of the Relevant Art

Allelopathy, a form of chemical warfare between plants, can be defined as the production and release of chemical substances by one species that inhibit the growth of another species (Inderjit and Duke. 2003. *Planta* 217:529-539; Weston and Duke. 2003. *Crit. Rev. Plant Sci.* 22:367-389). Allelopathic interactions have been proposed to have profound effects on the evolution of plant communities through the loss of susceptible species via chemical interference, and by imposing selective pressure favoring individuals resistant to inhibition from a given allelochemical (e.g., Schulz and Wieland. 1999. *Chemoecology* 9:133-141). Furthermore, allelopathic compounds released by grain crop species are thought to play a significant role in cover crops or within intercropping systems where they act as weed suppressants. Allelopathic compounds have been characterized in number of plants such as black walnut, wheat, rice, and sorghum (Bertin et al. 2003. *Plant Soil* 256: 67-83; Inderjit and Duke, supra; Duke at al. 2005. *Outlooks Pest Management* 16: 64-68).

Despite the ecological and agronomic importance of allelochemicals, relatively few pathways have been characterized in detail at the molecular level. One notable exception is the identification and characterization of all the genes encoding the enzymes responsible for the biosynthesis of the benzoxazinoid, 2,4-dihydroxy-7-methoxy-2H-1,4-benzoxazin-3 (4H)-one in *Zea mays* (Frey et al. 1997. *Science* 277:696-699). Benzoxazinoids are thought to act as alleopathic chemicals in the rhizosphere, in addition to being defense compounds against microbial pathogens and insect herbivores (Sicker at al. 2000. *Int. Rev. Cytol.* 198:319-346; Friebe, A. 2001. *J. Crop Prod.* 4:379-400).

Sorgoleone, an allelochemical of particular interest to plant chemical ecology as well as agriculture, has only been found to be produced by members of the genus *Sorghum* (Czarnota at al. 2003b. *J. Chem. Ecol.* 29:2073-2083; Baerson et al. 2008b. *Plant Signal Behav.* 3:667-670). The term sorgoleone is most frequently used to describe the compound corresponding to the predominant congener identified in sorghum root exudates (Netzly et al. 1988. *Weed Sci.* 36:441-446; Kagan et al. 2003. *J. Agric. Food Chem.* 51: 7589-7595), 2-hydroxy-5-methoxy-3-[(Z,Z)-8',11',14'-pentadecatriene]-p-benzoquinone (FIG. 1), which has been estimated to account for between approximately 40-90% of the exudate material (w/w) in various accessions (e.g. Nimbal et al. 1996. *J. Agric. Food Chem.* 44: 1343-1347; Czarnota et al. 2001. *Weed Technol.* 15: 813-825; Baerson et al. 2008a. *J. Biol. Chem.* 283:3231-3247; Dayan et al. 2009. *J. Exp. Bot.* 60:2107-2117). The remaining exudate consists primarily of 4,6-dimethoxy-2-[(Z,Z)-8',11',14'-pentadecatriene]resorcinol(methoxy-dihydrosorgoleone), and sorgoleone congeners differing in the length or degree of saturation of the aliphatic side chain, and in the substitution pattern of the quinone ring (Erickson et al. 2001. *J. Agric. Food Chem.* 49: 5537-5542; Kagan et al., supra; Rimando et al. 2003. *J. Nat. Prod.* 66: 42-45; Dayan et al. 2009, supra). The fact that sorgoleone acts as a potent broad-spectrum inhibitor active against many agronomically important monocotyledonous and dicotyledonous weed species, exhibits a long half-life in soil, and appears to affect multiple targets in vivo (e.g., Netzly & Butler. 1986. *Crop Sci.* 26: 775-780; Einhellig and Souza. 1992. *J. Chem. Ecol.* 18: 1-11; Nimbal et al., supra; Rimando et al., 1998. *J. Nat. Prod.* 61: 927-930; Czarnota et al. 2001. *Weed Technol.* 15: 813-825; Bertin et al. 2003. *Plant Soil* 256:67-83; Duke, S. O. 2003. *Trends Biotechnol.* 21: 192-195) may make it promising for development as a natural product alternative to synthetic herbicides (Duke, supra).

The biosynthesis of sorgoleone is thought to occur exclusively in root hairs, which appear as cytoplasmically dense cells in sorghum, containing large osmiophilic globules presumably associated with sorgoleone rhizosecretion (Czarnota et al. 2001, supra; Czarnota et al. 2003a. *Int. J. Plant Sci.* 164:861-866). Prior labeling studies have indicated a polyketide origin for the quinone ring of sorgoleone (Fate and Lynn. 1996. *J. Amer. Chem. Soc.* 118:11369-11376; Dayan et al. 2003. *J. Biol. Chem.* 278: 28607-28611), thus lending support for the initial steps in the proposed biosynthetic pathway shown in FIG. 1, where 5-pentadecatrienyl resorcinol (5-[(8'Z,11'Z)-8',11',14'-pentadecatrienyl]resorcinol) is produced by a polyketide synthase enzyme accepting a $16:3\Delta^{9,12,15}$ fatty acyl-CoA starter unit. A specific sub-class of type III polyketide synthases, referred to as alkylresorcinol synthases [first described in microorganisms—(Funa et al. 2006. *Proc. Nat. Acad. Sci. USA* 103:6356-6361; Funa et al. 2007. *J. Biol. Chem.* 282:14476-14481)], have been proposed to participate in the biosynthesis of plant alkylresorcinols such as 5-pentadecatrienyl resorcinol (Austin and Noel. 2003. *Nat. Prod. Rep.* 20: 79-110; Dayan et al. 2003, supra). Two *S. bicolor* fatty acid desaturases (designated DES2 and DES3) likely involved in the formation of the proposed $16:3\Delta^{9,12,15}$ fatty acyl-CoA starter unit have recently been characterized (Pan et al. 2007. *J. Biol. Chem.* 282:4326-4335). Subsequent modification of the 5-pentadecatrienyl resorcinol intermediate is likely mediated by the AdoMet-dependent O-methyltransferase OMT3 (Baerson et al. 2008a. *J. Biol. Chem.* 283:3231-3247) and by unidentified hydroxylases (possibly P450 monooxygenases), yielding dihydrosorgoleone, which rapidly undergoes oxidation to the benzoquinone (FIG. 1).

Type III polyketide synthases, which have been identified in both plants and microorganisms, are involved in the biosynthesis of a wide array of natural products, including flavonoids derived from the key intermediate 2',4,4',6'-tetrahydroxychalcone synthesized by the enzyme chalcone synthase (CHS; Austin and Noel, supra). These enzymes occur as homodimers possessing subunits between 40-45 kDa in size, and catalyze iterative decarboxylative condensation reactions, typically using malonyl-CoA extender units. Type III PKSs from various sources can differ in the types of starter units accepted, the number of condensation steps performed, and the type of intramolecular cyclization reaction performed, all of which contribute to the diversity of compounds produced by these enzymes (Austin and Noel, supra; Khosla et al., 1999. *Annu. Rev. Biochem.* 68:219-253). For example, the closely-related CHS and stilbene synthase (STS) type III enzymes both catalyze the formation of identical tetraketide intermediates from p-coumaryl-CoA, yet form different products due to cyclization occurring via a C6→C1 Claisen condensation for CHS, and a C2→C7 aldol condensation for STS-type enzymes (Tropf et al. 1994. *J. Mol. Evol.* 38:610-618). Alkylresorcinol synthases, which produce 5-alkylresorcinols from fatty acyl-CoA starter units, also use a STS-type cyclization mechanism, and with specific acyl-CoA starters may also generate pyrone by-products via intramolecular C5 oxygen→C1 lactonization (Funa et al. 2006, supra; Funa et al. 2007, supra; Funabashi at al. 2008. *J. Biol. Chem.* 283: 13983-13991; Goyal et al. 2008. *J. Struct. Biol.* 162:411-421).

Alkylresorcinols are members of an extensive family of compounds possessing varied bioactivities and biological roles referred to as phenolic lipids, which are thought to be derived predominantly from polyketide-associated pathways (Austin and Noel, supra). Sorgoleone represents one of the more extensively-studied phenolic lipids identified in plants; other important examples include urushiol, an allergen from poison ivy (*Toxicodendron radicans*), anacardic acid, an antifeedant found in several dicotyledonous species such as cashew (*Anacardium occidentale*), as well as the alkylresorcinol phytoanticipins found throughout the Poaceae (grass) family (Kozubek and Tyman. 1999. *Chem. Rev.* 99:1-26; Kozubek et al., 2001. *Cell. Mol. Biol. Lett.* 6:351-355). Plant-derived phenolic lipids have also been used by industry, for example in manufacturing of formaldehyde-based polymers and in lacquering processes (Kozubek and Tyman, supra).

Prior studies on type III PKS-like sequences from *S. bicolor* have involved the characterization of 8 sequences (designated CHS1-8) obtained from genomic library screens and analysis of expressed sequence tags (Lo et al. 2002. *Physiol. Mol. Plant. Path.* 61:179-188; Yu at al. 2005. *Plant Physiol.* 138:393-401). Recombinant enzyme studies have identified CHS8 as an STS and CHS2 as a typical CHS-type enzyme, and it is has been proposed that CHS1, 3, 4, 5, 6 and 7 also represent CHS-type enzymes given their high degree of sequence identity (≥97.5%) with CHS2 (Christine et al., supra).

Relatively little functional data exists concerning the genes and corresponding enzymes involved in the biosynthesis of alkylresorcinols in higher plants, thus new tools for exploring related pathways are needed, particularly in the Poaceae family where the occurrence of presumed phytoanticipin alkyresorcinols is widespread. Here, we have cloned and characterized two paralogous alkylresorcinol synthases (ARS) from *S. bicolor* (genotype BTx623), designated ARS1 and ARS2, important for the biosynthesis of the 5-pentadecatrienyl resorcinol precursor to sorgoleone.

SUMMARY OF THE INVENTION

We have cloned, expressed and characterized ARS1 (SEQ ID NO:1) and ARS2 (SEQ ID NO:3), two alkylresorcinol synthase genes from sorghum, and confirmed that their expression results in the production of the enzyme sorghum alkylresorcinol synthase 1 (ARS1) and alkylresorcinol synthase 2 (ARS2) in vitro and in vivo.

In accordance with this discovery, it is an object of the invention to provide isolated nucleic acid molecules which encode the ARS1 (SEQ ID NO:2) and ARS2 (SEQ ID NO:4) proteins, enzymes involved in the biosynthesis of the 5-pentadecatrienyl resorcinol precursor to sorgoleone.

It is a further object of the invention to provide constructs which encode the *Sorghum bicolor* ARS1 and ARS2 proteins.

It is a still further object of the invention to provide a vector which comprises a construct which is capable of expressing said ARS1 and ARS2 genes.

It is an additional object of the invention to provide transgenic plants, plant cells, and seeds containing the nucleic acid construct.

It is a another object of the invention to provide a method of transforming the ARS1 and ARS2 genes into plants by administering a vector, wherein said vector comprises an effective amount of a nucleic acid construct, which is a DNA sequence capable of transforming the ARS1 or ARS2 gene into a plant, and whereby said administration of the vector is effective for the resulting in the biosynthesis of alkylresorcinol precursors to sorgoleone in said plant.

It is yet another object of the invention to provide vectors for RNAi-mediated repression of ARS1 and ARS2 gene expression and a method for reducing sorgoleone accumulation in plants through RNA interference.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 2A depicts the determination of 5-pentadecatrienyl resorcinol levels by GC-MS analysis of methanol extracts prepared from isolated root hairs (upper panel) and total roots (lower panel) of 8-day-old etiolated seedlings of *S. bicolor* genotype BTx623. Extracted ion chromatograms are shown defined at m/z 314, and 5-pentadecatrienyl resorcinol peaks (retention time 14.8 min) are indicated by arrows. The corresponding mass spectrum for 5-pentadecatrienyl resorcinol is shown as an inset in the lower panel. FIG. 2B shows the relative expression levels of five PKS-like contig sequences identified in root hair ESTs determined by quantitative real-time RT-PCR using gene-specific primers. Data were normalized to an internal control (18S rRNA), and the ΔΔCT method was used to obtain the relative expression levels for each sequence, expressed as mean±SD from assays performed in triplicate.

FIG. 3 shows the alignment of the deduced amino acid sequences encoded by root hair-specific contigs 2_126, 2_127, and 0_1848. The deduced amino acid sequences based on contigs 2_126 (ARS1; SEQ ID NO:2), 2_127 (ARS2; SEQ ID NO:4), and 0_1848 (SEQ ID NO:9) were aligned with *Medicago sativa* chalcone synthase 2 (CHS2; SEQ ID NO:5), *Gerbera hybrida* 2-pyrone synthase (2-PS; SEQ ID NO:6), *Sorghum bicolor* chalcone synthase 2 (CHS2; SEQ ID NO:7), and *S. bicolor* stilbene synthase 1 (STS1; SEQ ID NO:8) using ClustalW. Residues associated with PKS functional diversity, catalysis ('catalytic triad'), and coenzyme A binding are indicated based on previous crystallography studies (Ferrer et al. 1999. *Nat. Struct. Biol.* 6: 775-784) and Jez et al. (2000. *Chem. Biol.* 7:919-930), and by computational homology modeling of ARS1 and ARS2. Numbering shown above the 'catalytic triad' positions, as well as several key residues potentially contributing to active site architecture is based on the *M. sativa* CHS2 sequence. Also indicated by boxes are atypical residues identified within the 0_1848-encoded polypeptide which could account for the lack of enzymatic activity observed in recombinant enzyme studies.

FIG. 7A depicts the real-time PCR analysis of 35S::ARS1 and 35S::ARS2 transcript levels from assays performed in triplicate. Values are shown as average±S.D. FIG. 7B depicts the average C15:0 alkylresorcinol content from 2 technical replicates. Line designations: PKS40-1, 5, 6, 7, 8 generated using the binary vector pZP212_ARS1; PKS44-1, 2, 10, 13, 14 generated using the binary vector pZP212_ARS2.

FIG. 9A shows the relative ARS1 and ARS2 endogenous transcript levels in 10 day-old *S. bicolor* hpRNA "+" and hpRNAi "−" seedlings (representing 6 independent transformant events) determined by quantitative real-time RT-PCR using gene-specific primers. Data were normalized to an internal control (18S rRNA), and the ΔΔCT method was used to obtain the relative expression levels for each sequence, expressed as mean±SD from assays performed in triplicate. FIG. 9B shows that ten micrograms of genomic DNA isolated from leaf samples of the 6 *S. bicolor* RNAi transformant events and control (genotype Tx430) seedlings were digested with either BamHI or SphI, then size-fractionated on 0.8% (w/v) agarose gels and transferred to nylon membranes. Blots were then hybridized using $^{32}$P-labeled *A. thaliana* FAD2 gene intronic sequences, washed at high stringency, then subjected to autoradiography. D, control; B, BamHI; S, SphI. FIG. 9C shows sorgoleone levels determined by GC-MS analysis of root exudates prepared from 10 day-old hpRNA "+" and hpRNAi "−" seedlings representing the 6 RNAi transformant events. Data are expressed as mean±SD, from four measurements. The limit of quantitation (LOQ), determined to be approximately 0.003 µg/mg fresh weight, is also indicated by a dashed line.

FIG. 12A depicts *Medicago sativa* CHS2 active site (MsCHS2). FIG. 12B depicts *Gerbera hybrida* 2-pyrone synthase active site (Gh 2-PS). FIGS. 12C and 12D depict ARS1 and ARS2 three-dimensional active site models, respectively.

FIG. 13 depicts the alignment of *Oryza sativa* (cv. Nipponbare) sequences exhibiting alkylresorcinol synthase activity. The predicted open reading frames (SEQ ID NOs:11, 12, and 13, encoded by *O. sativa* XP 476153, NP 920020, and NP 001064197, respectively, were aligned with *Medicago sativa* chalcone synthase 2 (CHS2), *S. bicolor* chalcone synthase 2 (CHS2), *O. sativa* chalcone synthase 1 (CHS1; SEQ ID NO:10), as well as the three *S. bicolor* sequences used for recombinant enzyme studies in the present work (ARS1, ARS2, and putative PKS 0_1848) using Clustal W. Residues associated with PKS functional diversity, catalysis ('catalytic triad'), and coenzyme A binding are indicated based on previous crystallography studies (Ferrer et al. and Jez at al., supra), and by computational homology modeling of ARS1 and ARS2. Numbering shown above the 'catalytic triad' positions, as well as several key residues potentially contributing to active site architecture is based on the *M. sativa* CHS2 sequence. Also indicated by boxes are atypical residues identified within the 0_1848-encoded polypeptide which could account for the lack of enzymatic activity observed in recombinant enzyme studies.

DETAILED DESCRIPTION OF THE INVENTION

Figure 1:
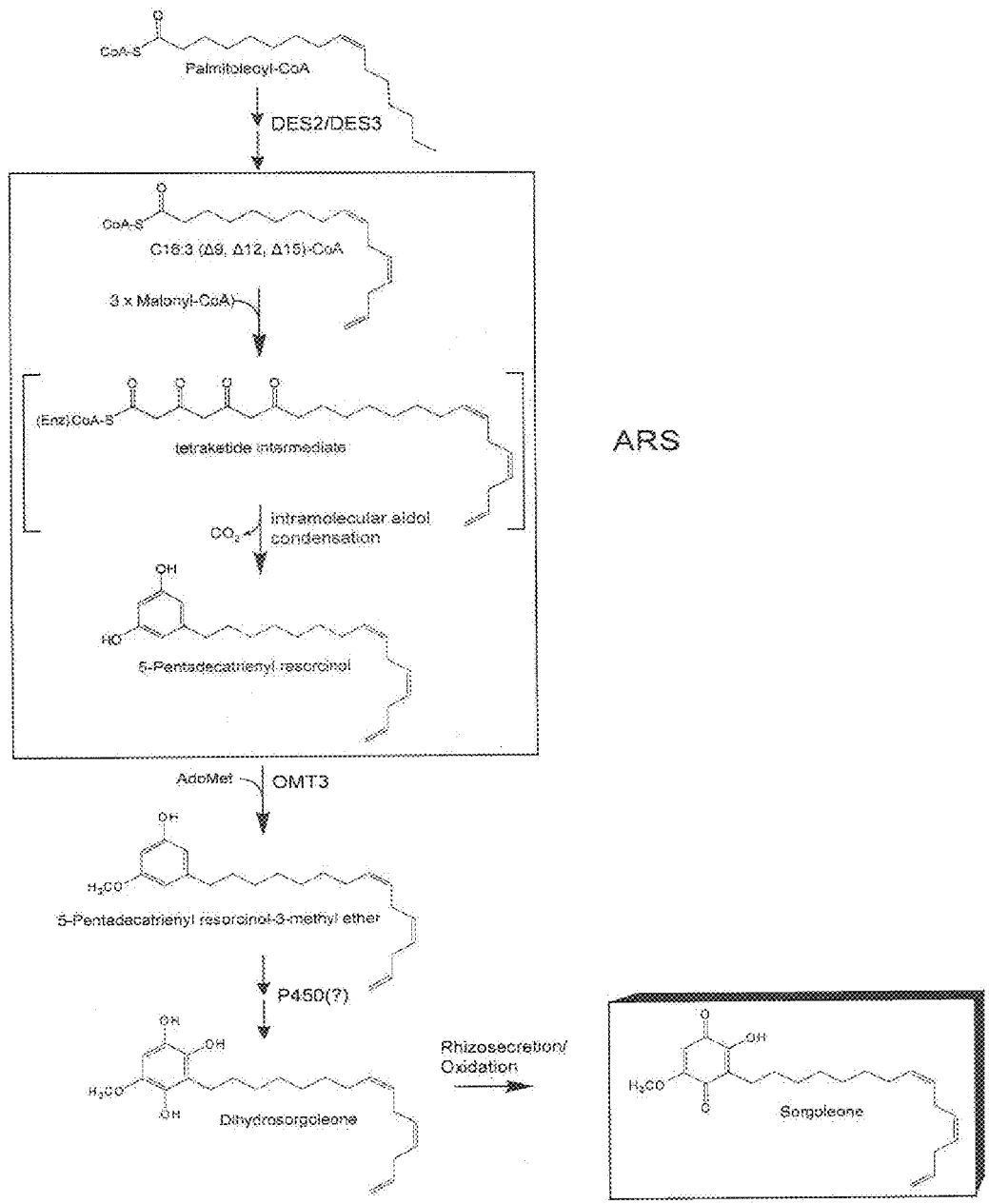
FIG. 1 depicts the biosynthetic pathway of the allelochemical sorgoleone. The hydroquinone, dihydrosorgoleone, produced in vivo, is thought to undergo autooxidation once secreted into the rhizophere to yield the more stable benzoquinone, sorgoleone. ARS, alkylresorcinol synthase; DES, fatty acid desaturase; OMT, O-methyltransferase; P450, cytochrome P450.

This invention concerns the cloning and functional characterization of two paralogous alkylresorcinol synthases (ARS) from *S. bicolor* (genotype BTx623), designated ARS1 (SEQ ID NO:2) and ARS2 (SEQ ID NO:4), for the biosynthesis of the 5-pentadecatrienyl resorcinol precursor to sorgoleone. These enzymes can potentially produce a range of different alkylresorcinols, possessing different side chains, in plants (not just 5-pentadecatrienyl resorcinol), depending on what fatty acyl-CoA substrates are available. The various different alkylresorcinol type products have various uses for industry as well as agriculture. In addition, the sequences of ARS1 and ARS2 were also used in the present work to identify several genes from rice (ssp. *japonica* cv. Nipponbare) involved in the biosynthesis of alkylresorcinols in this species.

These alkylresorcinol synthases catalyze the formation of phenolic lipids, utilizing fatty acyl-CoA precursors plus malonyl-CoA. One such phenolic lipid produced by these enzymes, 5-pentadecatrienyl resorcinol, serves as a precursor for the biosynthesis of the allelochemical sorgoleone in sorghum plants. The catalytic activity of these enzymes was confirmed by heterologous expression in *Escherichia coli* cells.

Alkylresorcinol synthases play several important roles in plant secondary metabolism, including providing precursors used for the biosynthesis of compounds involved in host defense against microbial pathogens, as well as compounds thought to play a role in inhibiting the growth of competing plant species. The lipid resorcinol sorgoleone is associated with the latter phenomenon, referred to as allelopathy, and has also been shown to possess antimicrobial activity. In addition to serving as host defense compounds in plants, polyketide-derived pigments such as anthocyanins are responsible for many of the colors found in flowers and fruits, which serve as attractants for pollinators, UV protectants, as well as fulfilling several other important biological roles. The identification of these enzymes from sorghum provides new genetic engineering opportunities in plants, not only for altering phenolic lipid content potentially leading to the generation of novel germplasm possessing enhanced agronomic characteristics such as increased allelopathy and disease resistance (e.g., Duke S. O., 2003. *Trends in Biotechnology* 21:192-195; Suzuki et al. 1998. *Phytochemistry* 47:997-1001; Arkadiusz and Tyman. 1999. *Chem. Rev.* 99:1-26), but also for the use of plants cells as bioreactors, thus providing an efficient source for obtaining phenolic lipids in large scale.

Based on the demonstrated ability of alkylresorcinol synthases (ARSs) ARS1 and ARS2 to generate phenolic lipids utilizing fatty acyl-CoA precursors plus malonyl-CoA in in vitro assays, a strategy was devised for the production phenolic lipids in transgenic plants. A second strategy was also devised to produce transgenic sorghum plants lacking the allelochemical sorgoleone using RNA interference technology (Small, I. 2007. *Curr. Opin. Biotechnol.* 18:148-53). The latter strategy is intended to circumvent problems associated with the allelopathic effects of sorghum grown under field conditions, which is known to cause inhibition of certain crops such as peanut and wheat grown in rotation with sorghum in cropping systems (e.g., Roth et al. 2000. *Agronomy Journal* 92:855-860; Sene of al. 2000. *J. Chem. Ecol.* 26: 625-637).

Figure 5:
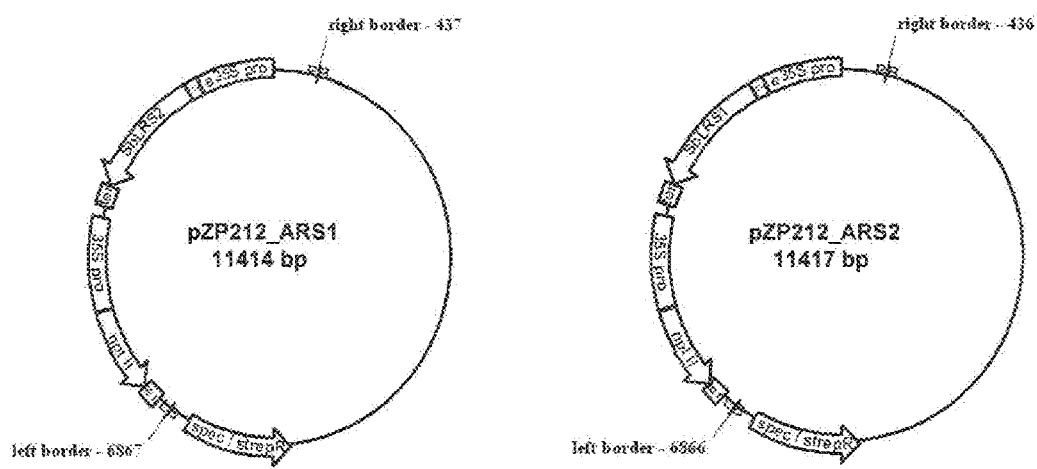
FIG. 5 depicts the binary vectors for the production of phenolic lipids in planta, through the overexpression of sorghum ARS1 or ARS2.

To test for the production of phenolic lipids in transgenic plants by expression of sorghum ARSs, ARS1 or ARS2, binary vectors were developed for expression of these sequences in planta (see FIG. 5). Recombinant *A. tumefaciens* strains harboring the vectors were used to transform *Arabidopsis thaliana* (cv. Col-0) using the 'floral-dip' procedure (Clough and Bent. 1998. *Plant J.* 16:735-43), and transgenic $T_1$ individuals were identified by selection on MS plates containing kanamycin. $T_2$ generation seedlings were used for all chemical analyses.

For experiments involving ARS1 and ARS2 overexpression in *Arabidopsis* plants, expression of both transgene cassettes in the various transgenic lines generated was confirmed by quantitative real-time PCR analyses, performed using leaf tissues samples as previously described (Baerson et al. 2005. *J. Biol. Chem.* 280:21867-21881). To assess whether C15:0 alkylresorcinol (5-pentadecyl resorcinol) was produced in plants harboring the ARS1 or ARS2 constructs, leaf tissues were harvested and pooled from transgenic *Arabidopsis* lines, and analyzed by gas chromatography/mass spectrometry (GC-MS).

Figure 7:
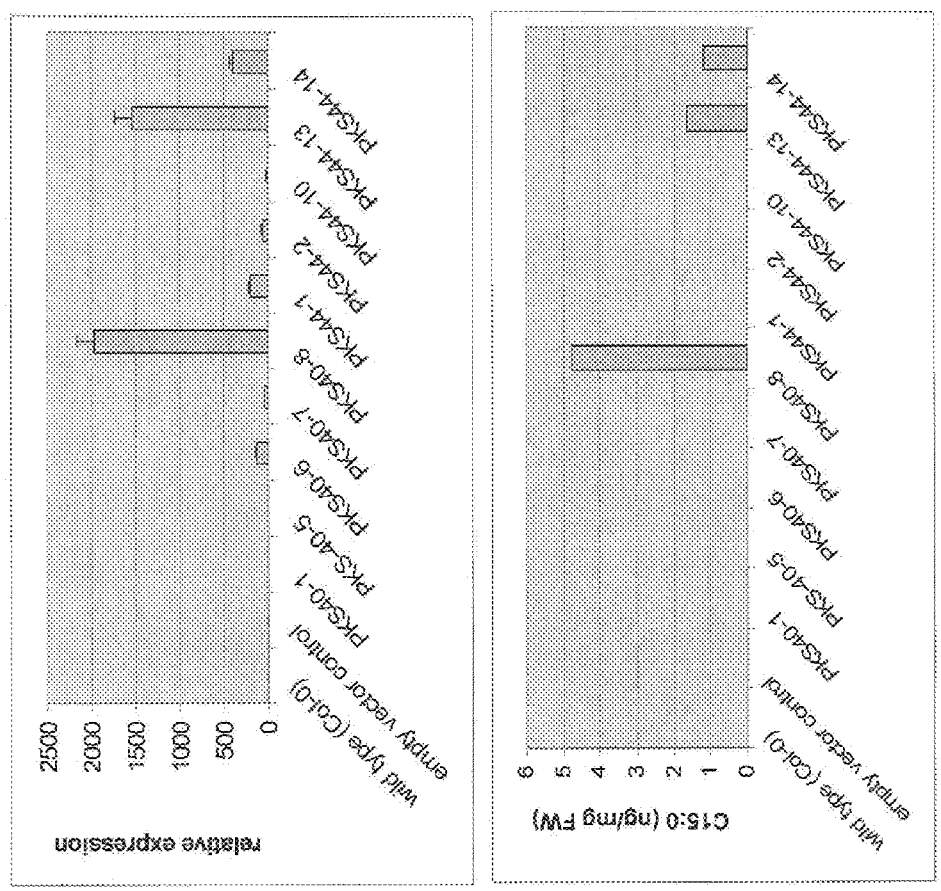
FIGS. 7A and 7B show the relative transgene expression and C15:0 alkylresorcinol content in transgenic and wild type *A. thaliana* plants.

As is the case for the majority of alkylresorcinol synthases, ARS1 and ARS2 can both utilize malonyl-CoA as the extender substrate, a compound ubiquitously present in plant tissues. Furthermore, ARS1 and ARS2 can both utilize fatty acyl-CoAs of various chain lengths as starter units, directly leading to the formation phenolic lipids possessing resorcinolic head groups. In leaf tissues of *A. thaliana*, palmitoyl-CoA (16:0) represents one of the predominant acyl-CoA pools (Browse and Somerville. 1991. *Annu. Rev. Plant Physiol. Plant Mol. Biol.* 42:467-506), thus a C15:0 alkylresorcinol would be predicted to accumulate in leaf tissues of ARS1- or ARS2-overexpressing *Arabidopsis* transformants (see Example 6; FIG. 7).

Five independent *Arabidopsis* lines transformed using the ARS1 binary vector, and 5 lines transformed using ARS2 vector were screened for expression of the 35S::ARS1 and 35S::ARS2 transcripts, respectively, as Well as for the presence of the C15:0 alkylresorcinol. Due to the extensive sequence identity shared between ARS1 and ARS2 coding sequences, the same real-time PCR assay was used to monitor both 35S::ARS1 and 35S::ARS2 transcript levels, thus their relative expression could be directly compared. The relative levels of alkylresorcinol detected in these three lines roughly paralleled their respective transgene expression levels suggesting that higher C15:0 alkylresorcinol levels could be achievable via increased ARS1 and ARS2 expression in planta.

These experiments demonstrate a utility of the invention described herein: transgenic plants expressing alkylresorcinol synthases such as ARS1 or ARS2 from *Sorghum bicolor* accumulate alkylresorcinols by utilizing available host fatty acyl-CoA and malonyl-CoA pools. The ability of ARS1 and ARS2 to efficiently utilize fatty acyl-CoA substrates in planta yielding phenolic lipids such as 5-pentadecyl resorcinol is a central feature of this technology. The present proof-of-concept represents a relatively simple test case, which can be further optimized for the production of phenolic lipids at higher levels or in specific tissues, for example, by the use of alternative promoter elements or other genetic elements required for the optimal expression of the transgene cassettes employed. It is anticipated that these relatively straight-forward modifications would result in significant increases in phenolic lipid production, or in the production in specific plant organs such as developing seeds or fruits. Related alkylresorcinol synthases could also be identified with more favorable kinetics that could also significantly enhance compound production. Such alternative alkylresorcinol synthase sequences could be isolated from diverse species by virtue of their sequence similarity to ARS1 and ARS2 using standard molecular biology techniques. In addition, while in the present example both ARS1 and ARS2 transgene cassettes used the strong, constitutively-expressed CaMV 35S promoter, gene promoters specifically induced by chemicals, pathogen infection, and other types of elicitors could be employed. In this case, the phenolic lipid would only be produced when crops are treated with specific chemical elicitors by growers, or automatically produced when plants are under attack by microorganisms or other adverse circumstances where phenolic lipid production would be beneficial to overall crop yields.

Figure 8:
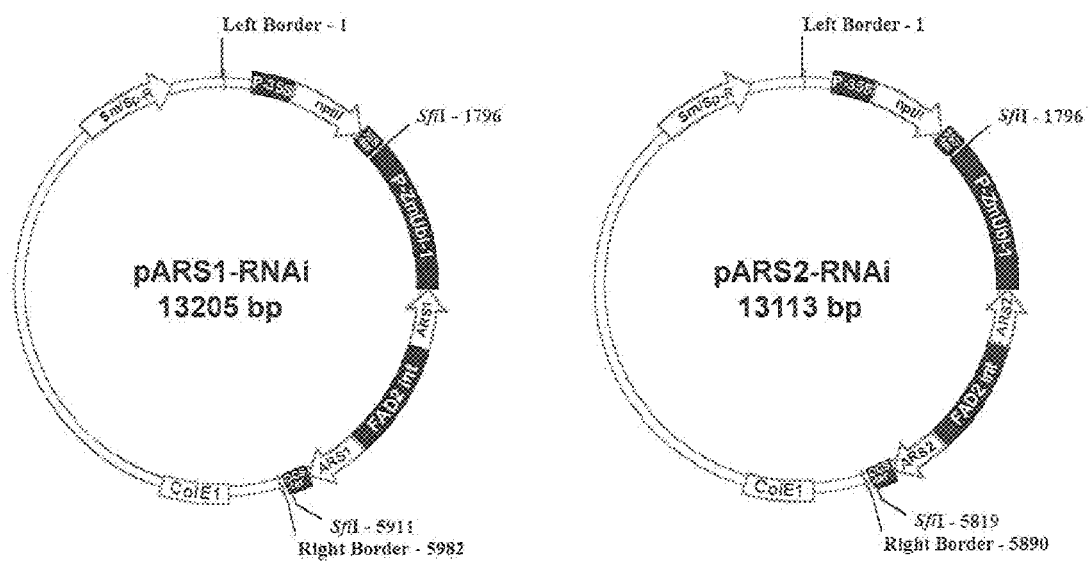
FIG. 8 depicts the binary vectors developed for RNAi-mediated inhibition of ARS1 and ARS2 expression. Construction of pARS1-RNAi and pARS2-RNAi are described (Example 7). The hpRNA-generating cassettes for both vectors were directionally-cloned using asymmetric SfiI restriction sites within the T-DNA borders of the binary vector pLH9000 (Hausmann and Töepfer, 1999. In: *Bioengineering of Custom-Tailored Rape Varieties*, Brauer et al, Eds, Göttingen, Germany), and include (5' to 3'): the constitutive *Zea mays* polyubiquitin-1 gene promoter and introns 1[P-ZmUbi-1; (Christensen et al. 1992. *Plant Mol. Biol.* 18:675-689)], sense and antisense ARS1 and ARS2 target regions separated by intron 1 of the *Arabidopsis thaliana* FAD2 gene [FAD2 int; (Okuley et al. 1994. *Plant Cell* 6: 147-158)], and the *Agrobacterium tumefaciens* octapine synthase gene terminator [OCS-ter; (De Greve et al. 1982. *J. Mol. Appl. Genet.* 1:499-511)]).

To disrupt the production of phenolic lipids (sorgoleone) in *Sorghum bicolor*, binary vectors were developed for RNAi-mediated repression of ARS1 and ARS2 (see FIG. 8). For these constructs, approximately 500 base pair target regions spanning the 3' coding regions and 3' UTRs of ARS1 and ARS2 were cloned in both sense and antisense orientation, separated by a 1.131 kb intron sequence derived from the FAD2 gene of *A. thaliana* (Okuley, et al., 1994. *Plant Cell* 6:147-158). The target regions chosen represent just one example of ARS1 and ARS2 gene sequences useful for RNAi-mediated repression of phenolic lipid synthesis in sorghum, however in principle any transcribed region from these genes could be used with potentially similar efficacy.

The ARS1 and ARS2-targetting RNAi cassettes were cloned within the T-DNA borders of the binary vector pLH9000 (Hausmann and Toepfer. 1999. In *Bioengineering of Custom-Tailored Rape Varieties*, Brauer, et al., Eds., Gesellschaft fuer Pflanzenzuechtung, Goettingen, Germany). The resulting constructs contain the RNAi expression cassettes arranged in a head-to-tail orientation (See Example 7). Recombinant *A. tumefaciens* strains harboring ARS1-RNAi and ARS2-RNAi constructs were used to transform immature embryos of *S. bicolor* (genotype Tx430).

The *S. bicolor* lines used to evaluate whether RNA interference-based inhibition of ARS1 and ARS2 expression results in sorgoleone-deficient plants were predominantly comprised of segregating $R_1$ individuals. We pre-screened individual seedlings using real-time PCR to confirm expression of the RNAi transgene in root tissues, then pooled root tissues obtained from these seedlings into either "+" (positive expressors) or "−" (non-expressors) pools for subsequent analysis of sorgoleone accumulation levels by GC-MS.

Eight independent *S. bicolor* lines were analyzed; and overall, a striking correlation was observed between RNAi transgene expression ("+" individuals) and loss of detectable amounts of sorgoleone found in roots. Among the eight lines tested, 4 were generated using the vector ARS1-RNAi and 4 were generated using the vector ARS2-RNAi. Comparable results were obtained with both vectors; loss of sorgoleone detectability occurred in all instances where either the ARS1-RNAi or the ARS2-RNAi-derived transgene was expressed. In two of the lines, RNAi transgene expression was not detected in any of the seedlings screened, and sorgoleone was found to be present in roots of those ("−") individuals. The high degree of sequence identity between ARS1 and ARS2, particularly within their 3' coding sequences, accounts for the observation that RNAi transgenes derived from either ARS1-RNAi or ARS2-RNAi severely inhibits or abolishes sorgoleone biosynthesis by simultaneously affecting the expression of both genes.

These experiments demonstrate an additional utility of the invention described herein: transgenic sorghum plants expressing sequences derived from ARS1 or ARS2 can be utilized to generate novel germplasm lacking the potent phytotoxin sorgoleone. Such germplasm has the potential to significantly expand the available options for farmers desiring to cultivate other crop species sensitive to sorgoleone in rotation with sorghum.

In the present example the RNA interference technique was employed to inhibit the expression of ARS1 and ARS2, however other techniques such as antisense expression (van den Elzen et al. 1989. *Plant Mol. Biol.* 13:337-346) or co-suppression (Jorgensen R. 1990. *Trends Biotechnol.* 8:340-344) utilizing sequences derived from ARS1 or ARS2 could also be used in theory to generate sorgoleone-deficient sorghum. Moreover, as mentioned, ARS1 or ARS2-derived sequences potentially useful for inhibiting sorgoleone biosynthesis could be derived from both coding and non-coding transcribed sequences, as well as non-transcribed sequences. The sequences selected for use in the vectors ARS1-RNAi or ARS2-RNAi which successfully inhibited sorgoleone biosynthesis in planta simply represent two examples out of many possibilities.

In addition, while in the present example both RNAi transgene cassettes were expressed using the strong, constitutively-expressed CaMV 35S promoter, gene promoters specifically induced by chemicals, or tissue-specific promoters could also be employed. In the former case, sorgoleone biosynthesis would only be inhibited when crops are treated with specific chemical elicitors by growers, and in the latter case expression of the RNAi transgene could be restricted to specific cell types to reduce potential off-target effects (Filichkin et al. 2007. *Plant Biotech. J.* 5:615-626).

Given that previous studies indicate that root hair cells serve as the primary site of sorgoleone biosynthesis in *Sorghum* spp. (Czarnota et al., 2001, supra; Czarnota et al. 2003a, supra), it is reasonable to speculate that the corresponding alkylresorcinol synthase(s) are predominantly or exclusively expressed in this cell type, and that the expected product, 5-pentadecatrienyl resorcinol, should also predominantly accumulate in root hairs. To further explore this, methanol extracts prepared from root hairs, root systems, developing panicles, stems, immature and fully-expanded leaves, and shoot apices were analyzed by GC-MS for the presence of 5-[(8'Z,11'Z)-8',11',14'-pentadecatrienyl]resorcinol. 5-pentadecatrienyl resorcinol was identified from total ion chromatograms of extracts prepared from the total root and isolated root hairs and the corresponding mass spectra for the peaks revealed characteristic fragment ions supporting this identification. Significantly, 5-pentadecatrienyl resorcinol was not detectable in any of the other tissues; moreover, signal levels obtained were consistently far higher in isolated root hairs than in total root systems. Collectively, these data are consistent with the suggested sorgoleone biosynthetic pathway localization in root hairs, involving a $16:3\Delta^{9,12,15}$ fatty acyl-CoA utilizing alkylresorcinol synthase expressed predominantly in this cell type.

The terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second. Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the ARS1 and/or ARS2 enzyme, operably linked to a promoter and/or other regulatory sequences.

As used herein, the term "express" or "expression" is defined to mean transcription alone. The regulatory elements are operably linked to the coding sequence of the ARS1 or ARS2 gene such that the regulatory element is capable of controlling expression of the ARS1 or ARS2 gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence which specifically induces the ARS1 or ARS2 gene expression in root hairs and roots. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense. RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

As used herein, the term "expressed sequence tag" (EST) refers to a short strand of DNA (approximately 200 base pairs long) which is part of a cDNA. ESTs provide an indication of the abundance of the genes that are being expressed in that tissue at that stage of development. Because an EST is usually unique to a particular cDNA, and because cDNAs correspond to a particular gene in the genome, ESTs can be used to help identify unknown genes and to map their position in the genome.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., 1985. Supp. 1987. *Cloning Vectors: A Laboratory Manual*; Weissbach and Weissbach. 1989. *Methods for Plant Molecular Biology*, Academic Press, New York; and Flevin of al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to the ARS1 or ARS2 polypeptide that is substantially free of other proteins, lipids, carbohydrates, or other materials with which it is naturally associated. One skilled in the art can purify ARS1 or ARS2 using standard techniques for protein purification. The purity of the ARS1 and ARS2 polypeptides can also be determined by amino-terminal amino acid sequence analysis.

The invention includes functional ARS1 and ARS2 polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of ARS1 or ARS2 polypeptide", refers to all fragments of ARS1 and ARS2 that retain ARS1 or ARS2 activity and function in the sorgoleone biosynthetic pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of ARS1 or ARS2 in the sorgoleone pathway can be utilized in bioassays to identify functional fragments of ARS1 or ARS2 polypeptide or related polypeptides.

Modifications of the ARS1 or ARS2 primary amino acid sequence may result in further mutant or variant proteins having substantially equivalent activity to the ARS1 and ARS2 polypeptides described herein. Such modifications may be deliberate, as by site-directed mutagenesis, or may occur by spontaneous changes in amino acid sequences where these changes produce modified polypeptides having substantially equivalent activity to the ARS1 and ARS2 polypeptides. Any polypeptides produced by minor modifications of the ARS1 or ARS2 primary amino acid sequence are included herein as long as the biological activity of ARS1 or ARS2 is present; e.g., having a role in pathways leading to sorgoleone accumulation in plants and in vitro.

A heterologous coding sequence refers to coding sequences which encode peptides or proteins, unrelated to, or, other than, the ARS1 or ARS2 polypeptides provided above and which are not intrinsically found in the position provided in the chimeric gene construct.

Genes encoding a ARS1 or ARS2 protein can be cloned using a variety of techniques according to the invention. The simplest procedure for the cloning of ARS1 and ARS2 genes requires the cloning of genomic DNA from an organism identified as producing an ARS1 or ARS2 protein, and the transfer of the cloned DNA on a suitable plasmid or vector to a host organism which does not produce the ARS1 or ARS2 protein, followed by the identification of transformed hosts to which the ability to produce the ARS1 or ARS2 protein has been conferred. The transforming ARS1 or ARS2-conferring DNA can be cleaved into smaller fragments and the smallest which maintains the ARS1 or ARS2-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a ARS1 or ARS2 polypeptide and which hybridize under stringent conditions, as described herein, to the ARS1 or ARS2 sequences disclosed herein, or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. For example, that portion of the ARS1 or ARS2 protein beginning with amino acid 209, i.e., isoleucine, and consisting of 94 contiguous amino acids or less (as described above), can be used to identify or isolate the ARS1 or ARS2 gene encoding said ARS1 or ARS2 protein in nucleotide sequences of plants other than sorghum. Thus, such a portion represents a "substantial portion" and can be used to establish "substantial identity", i.e., sequence identity of at least 80%, compared to the reference sequence, sorghum. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the ARS1 or ARS2 polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, ARS1 or ARS2 activity as described herein. Such variants may result from, for example, genetic polymorphism or from human manipulation. Biologically active variants of a native ARS1 or ARS2 protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired ARS1 or ARS2 activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of ARS1 or ARS2 protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The results described in the present work provide compelling evidence arguing in favor of a role for ARS1 and ARS2 in the sorgoleone biosynthetic pathway. Moreover, alkylresorcinols and their derivatives are wide-spread in higher plants, and are often of clinical significance, e.g. urushiol in poison ivy (reviewed in Kozubek and Tyman 1999, supra; Kozubek et al. 2001, supra). The sequences for ARS1 and ARS2 will therefore undoubtedly serve as invaluable tools for the detailed analysis of alkylresorcinol biosynthetic pathways from other plant species, particularly those identified in cereals such as rye, wheat, and barley (reviewed in Kozubek and Tyman 1999, supra; Kozubek et al. 2001, supra) where the alkyresorcinol synthases involved would be anticipated to share a high degree of sequence identity with these enzymes. The sequences of ARS1 and ARS2 were also used in the present work to identify several genes from rice (ssp. *japonica* cv. Nipponbare) likely involved in the biosynthesis of alkylresorcinols in this species.

EXAMPLES

Having now generally described this invention, the same will be better understood by reference to certain specific examples, which are included herein only to further illustrate the invention and are not intended to limit the scope of the invention as defined by the claims.

Example 1

Plant Materials and Growth Conditions

Seeds of *S. bicolor* genotype BTx623 were purchased from Crosbyton Seed Company (Crosbyton, Tex.), and seeds of *S. bicolor* genotype Tx430 were harvested from greenhouse-grown plants maintained at the University of Nebraska-Lincoln greenhouse facilities. For real-time RT-PCR experiments and 5-pentadecatrienyl GC-MS analyses, root tissues were obtained from 8-day-old dark-grown BTx623 seedlings grown under soil-free conditions using a capillary mat system devised by Czarnota and co-workers (Czarnota et al. 2001, supra) and root hairs were isolated from this material in bulk as previously described (Baerson at al. 2008a, supra). Immature leaves and shoot apices were isolated from BTx623 seedlings maintained in a growth chamber at 28° C. for 8 days in standard (approximately 20×40 cm) nursery flats using Premier Pro Mix PGX potting media (Hummert International, Earth City, Mo.) under a combination of cool-white fluorescent and incandescent lighting at an intensity of approximately 400 µmol $m^{-2}s^{-1}$ and a 16 h photoperiod; developing panicles, mature leaves, and culm (stem) tissues were isolated from 10-week-old greenhouse-grown BTx623 plants. At the time of harvest, panicles were partially exerted from flag leaf sheaths, just prior to anthesis. All harvested plant material was directly flash-frozen in liquid nitrogen and stored at –80° C. prior to analysis.

Example 2

EST Sequencing

Identification of PKS-Like Transcripts

EST Database mining was performed using the Magic Gene Discovery software (Cordonnier-Pratt at al. 2004. *Comp. Funct. Genomics* 5: 268-275), and by BLASTN and TBLASTN analysis. The EST data set used was derived from isolated root hair cells of *S. bicolor* genotype BTx623 and has been previously described (Baerson et al. 2008a, supra). All ESTs have been deposited in GenBank and have been incorporated into the current NCBI unigene release (build #27, 2 Mar. 2008).

The high levels of sorgoleone produced and exuded by root hair cells of *Sorghum* spp. members (Czarnota et al., 2001, supra), suggests that mRNAs encoding enzymes associated with sorgoleone biosynthesis could be among the most abundant in this cell type. Therefore, in effort to identify and functionally characterize these enzymes, we have previously initiated a functional genomics strategy involving the analysis of a data set comprised of 5,468 expressed sequence tags (ESTs) derived from isolated root hair cells of *S. bicolor* genotype BTx623 (Pan et al., supra; Baerson et al. 2008a, supra). Importantly, BTx623 is also the genotype used to generate the recently-completed sorghum genome sequence (Paterson et al., 2009. *Nature* 457:551-556), thus additional information such as predicted gene structures and chromosomal organization can be readily obtained for all contigs identified within the root hair EST data set.

For the identification of 5-pentadecatrienyl resorcinol in various wild-type *S. bicolor* (genotype BTx623) tissues, 250 mg aliquots of flash frozen, pulverized tissues were first washed by gentle swirling in 2 mL chloroform for 30 s to remove excess sorgoleone, then centrifuged at 16,000×g for 10 min at 4° C. Following removal of supernatants, tissue samples were dried under a stream of nitrogen, then lyophilized. The lyophilized samples were then mixed with 1.25 mL methanol, homogenized using a hand-held homogenizer for 30 s at 25,000 rpm, then filtered through 0.45 µm Puradisc 25AS syringe filters (Whatman, Piscataway, N.J.) into GC vials, and dried to completion under a stream of nitrogen gas. The dried extracts were then re-dissolved in methanol, and analyzed by GC-MS as described above for sorgoleone content determinations. Verification and identification of 5-pentadecatrienyl resorcinol in different tissues was performed by comparison of sample retention times and mass spectra (shown in FIG. 2A) relative to purified 5-pentadecatrienyl resorcinol standards.

To identify potential alkylresorcinol synthase-encoding transcripts expressed in root hairs, the root hair ESTs were mined for candidate polyketide synthases using both the MAGIC Gene Discovery software (Cordonnier-Pratt et al., supra), and also analyzed by BLASTN and TBLASTN searches (Altschul et al. 1997. *Nucleic Acids Res.* 25:3389-3402) using functionally characterized plant type III polyketide synthase sequences as queries. From these analyses, 9 polyketide synthase-like ESTs were identified, which assembled into 5 unique sequences by cluster analysis, 3 of which were singletons. Two of the PKS-like assemblies (I.D. numbers 2_126 and 2_127) are each comprised of 3 ESTs, and collectively represent approximately 0.11% of the total 5,468 expressed sequences identified in root hairs (Baerson et al. 2008a, supra). Additionally, two of the sequences (I.D. numbers 0_164 and 0_1821) correspond to CHS5 and CHS1, respectively, previously identified by Lo et al. (2002. *Physiol. Mol. Plant. Path.* 61:179-188) from genomic library screens which have not yet been functionally characterized.

To determine if the identified root hair PKS-like sequences exhibit expression patterns correlating with the accumulation of 5-pentadecatrienyl resorcinol (FIG. 2A), all 5 unique root hair PKS-like sequences were subjected to quantitative real-time RT-PCR analysis.

Example 3

Quantitative Real-Time RT-PCR Analysis

Quantitative Real-time PCR was performed as previously described (Baerson et al. 2005. *J. Biol. Chem.* 280:21867-21881). Total RNAs for use in real-time PCR experiments shown in FIG. 2B were isolated from 0.5 g aliquots of flash-frozen *S. bicolor* genotype BTx623 tissues using the Trizol reagent (Invitrogen Corp., Carlsbad, Calif.), with an additional homogenization step of 30 s at 25,000 rpm using a handheld homogenizer. RNAs were then re-purified with a RNeasy Plant Mini-Kit (Qiagen Inc., Valencia, Calif.), including an "on-column" DNase I treatment to remove residual DNA contamination (Qiagen Inc., Valencia, Calif.). RNA recovery and purity were determined spectrophotometrically for these samples, and sample integrity was also assessed by agarose gel electrophoresis.

Real-time PCR reactions were performed in triplicate using a model 7300 Sequence Detection System (Applied Biosystems, Foster City, Calif.) with gene-specific primers, and primers specific to 18S rRNA as internal controls. Gene-specific PCR primer pairs used for the 18s rRNA and five candidate polyketide synthases (FIG. 2B) are as follows: (18S rRNA, forward, 5'-GGCTCGAAGACGATCAGATACC-3'; SEQ ID NO:14, and reverse, 5'-TCGGCATCGTTTATG-GTT-3' (SEQ ID NO:15); 2_127, forward, 5'-ATAAAC-CCGCCATAGAAGTTGC-3' (SEQ-ID NO:16), and reverse, 5'-TTAGCCACAAGGAGCTCATTTTAC-3'; SEQ ID NO:17); 2_126, forward, 5'-CCCTGGCTAAAATAAG-GTCCAC-3' (SEQ ID NO:18), and reverse, 5'-CCTTAT GGTCCATGAATTGGC-3'; SEQ ID NO:19); (0_1848, forward, 5'-CTGGCGGAGGCA TGAGAC-3' (SEQ ID NO:20), and reverse, 5'-TGCAATCCTGATCCAAGTTCC-3'; SEQ ID NO:21); 0_164, forward, 5'-CGCTCGGTCTC-CATGAATC-3' (SEQ ID NO:22) and reverse, 5'-AAC-GATCGACGACTGGTGG-3'; SEQ ID NO:23); and 0_1821, forward, 5'-GAATGCTCCAGACATGGTAGA-CAG-3'(SEQ ID NO:24), and reverse, 5'-TTGTCATG-TAATGGACTCTAGACAGG-3' (SEQ ID NO:25). PCR primers were designed using Primer Express® v2.0 software (Applied Biosystems, Foster City, Calif.) and the Amplify program (Engels, W. R. 1993. *Trends Biochem. Sci.* 18: 448-450). A dissociation curve was generated at the end of each PCR cycle to verify that a single product was amplified using software provided with model 7300 Sequence Detection System. A negative control reaction minus cDNA template (non-template control) was also routinely performed in triplicate for each primer pair. The change in fluorescence of SYBR® Green I dye in every cycle was monitored by the GenAmp® 7300 system software, and the threshold cycle ($C_T$) above background for each reaction was calculated. The $C_T$ value of 18S rRNA was subtracted from that of the gene of interest to obtain a $\Delta C_T$ value. The $C_T$ value of an arbitrary calibrator (e.g., the tissue sample from which the largest $\Delta C_T$ values were obtained) was subtracted from the $\Delta C_T$ value to obtain a $\Delta\Delta C_T$ value. The fold-changes in expression level relative to the calibrator were calculated as $2^{-\Delta\Delta C_T}$.

Figure 2:
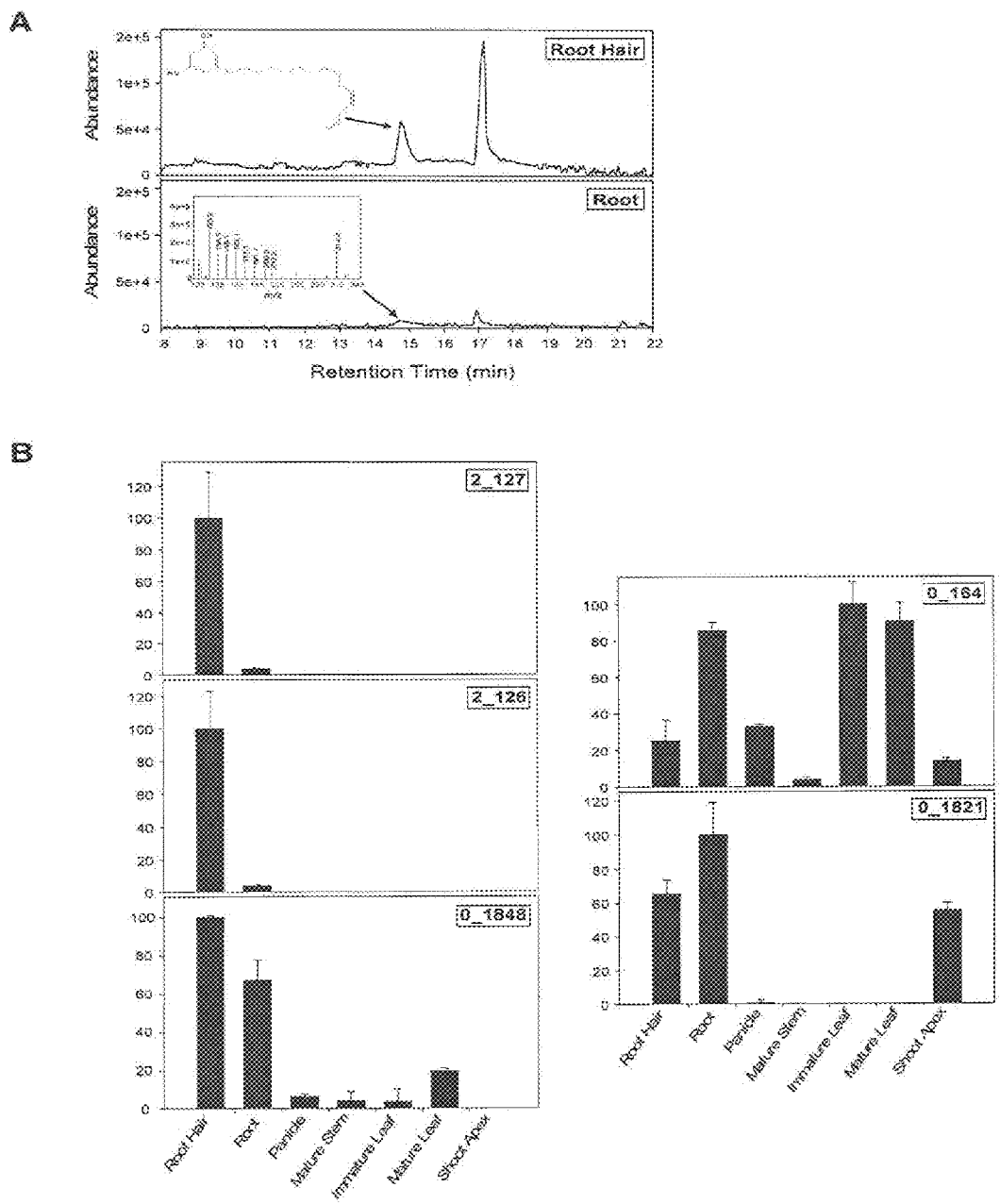
FIGS. 2A-2B show a comparison of 5-pentadecatrienyl resorcinol and PKS-like transcript accumulation in various *S. bicolor* tissues.

Gene-specific primers were designed for monitoring mRNA steady-state accumulation levels in assays using cDNAs prepared from root hairs, root systems, developing panicles, stems, immature and fully-expanded leaves, and shoot apices (FIG. 2B). All cDNAs used in these experiments were derived from the identical tissue samples used for GC-MS analysis of 5-pentadecatrienyl resorcinol.

Figure 3:
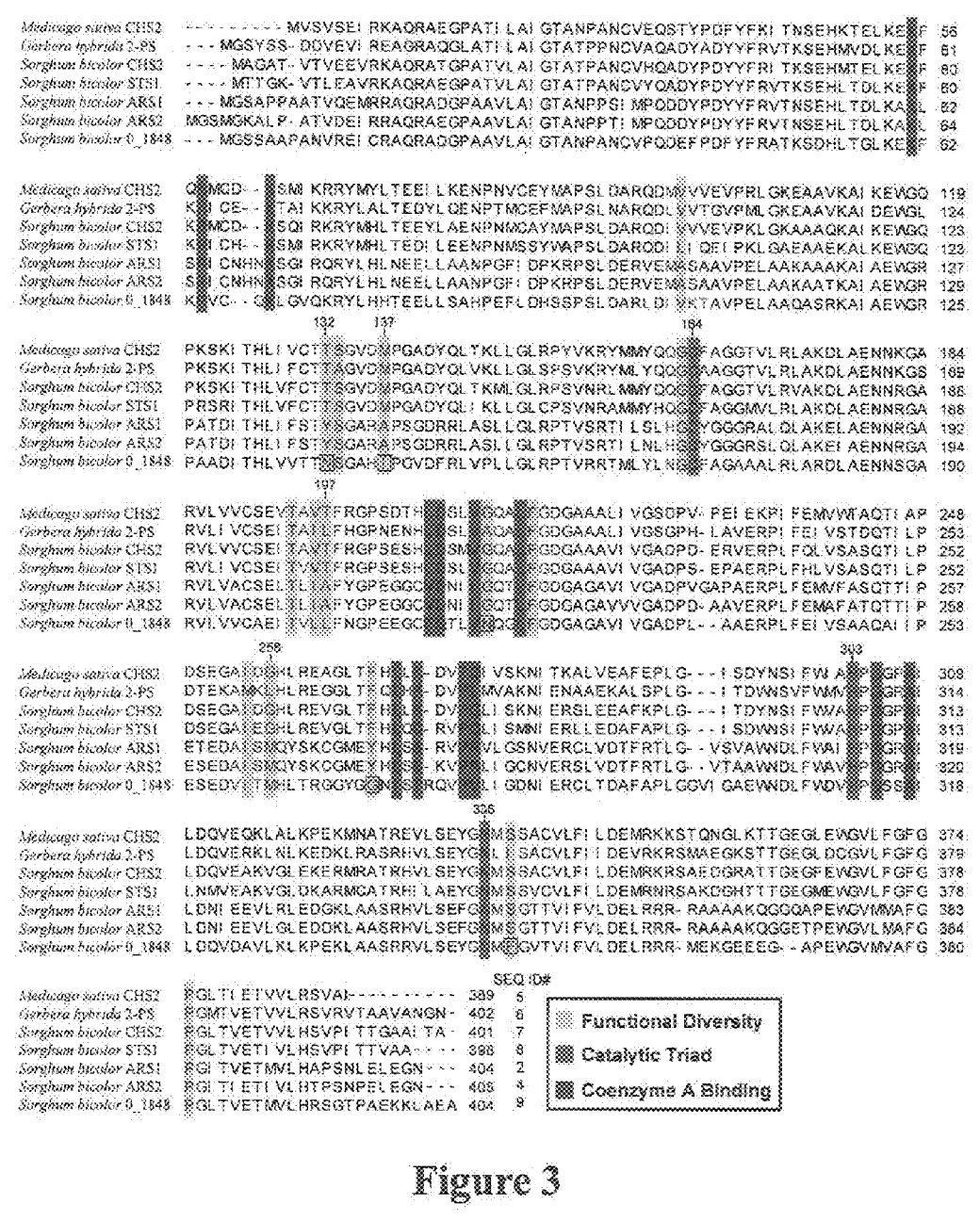

As shown in FIG. 2B, 3 of the 5 PKS-like candidates, (2_127, 2_126, and 0_1848—FIG. 2B), exhibited root hair-preferential expression patterns, whereas sequences 0_164 (CHS5) and 0_1821 (CHS1) were maximally expressed in developing leaves and total roots, respectively. The expression patterns of the 5 PKS-like sequences were further analyzed in silico by monitoring EST counts within the 18 different *S. bicolor* (genotype BTx623) EST libraries developed by the University of Georgia Laboratory for Genomics and Bioinformatics (Retrieved from the Internet: <URL:fungen.org/Sorghum.htm). Interestingly, EST's corresponding to PKS-like sequences 0_1848, $0_{164}$ (CHS5), and 0_1821 (CHS1) were found in several different EST libraries, whereas sequences 2_127 and 2_126, exhibiting the most highly root hair-preferential expression pattern in quantitative RT-PCR experiments (FIG. 2B), could only be identified in root hair ESTs (not shown).

Complete open reading frames (ORFs) were determined for the three candidate sequences exhibiting root hair-preferential expression (2_127, 2_126 and 0_1848) by 5'-rapid amplification of cDNA ends (RACE). The predicted full-length open reading frames for all 3 sequences exhibited extensive sequence similarity at the amino acid level to previously characterized plant type III polyketide synthases (Austin and Noel, supra), and contained conserved residues and motifs putatively associated with catalysis and substrate binding, based on the crystal structures determined for *Medicago sativa* (CHS2) and *Gerbera hybrida* (2-PS) type III enzymes (Ferrer et al., supra; Jez et al., supra; FIG. 3). The predicted ORFs derived from all 3 PKS-like sequences encode approximately 43 kDa proteins with predicted isoelectric points of 6.27 (2_127), 5.67 (2_1.26), and 5.78 (0_1848). Additionally, the ORFs predicted from 2_126 and 2_127 share approximately 91% identity at the amino acid level, and both share approximately 60% amino acid identity with the predicted ORF for 0_1848.

Example 4

Heterologous Expression of Recombinant Polyketide Synthases

Partial (5'-truncated) coding sequences for *S. bicolor* ARS1, ARS2, and PKS-like 0_1848 were obtained from previously-generated root hair expressed sequence tag assemblies (Baerson et al. 2008a, supra), which served as the basis to obtain full-length ORFs by Rapid Amplification of cDNA ends (5'-RACE). For these experiments, a SMART RACE cDNA Amplification Kit (Clontech Laboratories Inc., Palo Alto, Calif.) was used per manufacturer's instructions with total RNA isolated from *S. bicolor* genotype BTX623 root hairs. PCR amplification products containing the complete ORFs for ARS1, ARS2, and PKS-like 0_1848 flanked by NDeI (5' end) and BamH1 (3' end) restriction sites were then generated by PCR amplification, to facilitate direct ligation with NdeI- and BamHI-digested pET15b (EMD Biosciences, La Jolla, Calif.). Similarly, the predicted full-length open reading frames for the *O. sativa* PKS-like sequences encoded by LOC_Os05g12180, LOC_Os10g08620, and LOC_Os10g07040 flanked by NdeI (5' end) and BgIII (3' end) restriction sites were directly amplified from cDNA prepared from 2 week-old greenhouse-grown *O. sativa* (cv. Nipponbare) seedlings, digested with NdeI and BgIII, then ligated with NdeI- and BamHI-digested pET15b. The resulting expression vectors contained the 6 different PKS full-length ORFs in-frame with pET15b poly-histidine tract and thrombin cleavage site, as confirmed by DNA sequence analysis. The primer pairs used for PCR amplifications were as follows: ARS1 forward, 5'-CATATGGGGAGCGCAC- CGC-3'(SEQ ID NO:26), and reverse, 5'-GGATCCT-CAATTTCCCTCCAGTTCCAGGT-3'(SEQ ID NO:27); ARS2 forward, 5'-CATATGGGGTCCATGGGGAAGG-3' (SEQ ID NO:28), and reverse, 5'-GGATCCTCAATTTC-CCTCCAGTTCCGG-3'(SEQ ID NO:29); 0_1848 forward, 5'-CATATGGGAAAGTAGTGCTGCTCCG-3'(SEQ ID NO:30), and reverse, 5'-GGATCCTCAATGCCTCCGC-CAGTTTC-3'(SEQ ID NO:31); Os05g12180 forward, 5'-ATATCATATGCCTGGAACAGCTACTGC-3'(SEQ ID NO:32), and reverse, 5'-ATATAGATCTTCAT-GAGAGTGGGTTACGCAAC-3'(SEQ ID NO:33); Os10g08620 forward, 5'-ATATCATATGCCTGGAGCAGC-TACCAC-3'(SEQ ID NO:34), and reverse, 5'-ATATA-GATCTCTAATTTTGCTTAAGACCACGTG-3'(SEQ ID NO:35); Os10g07040 forward, 5'-ATATCATATGCCTG-GAGCAACTACCCG-3'(SEQ ID NO:36), and reverse, 5'-ATATAGATCTTTAATTTTCCTTCAAACCACGTG-3' (SEQ ID NO:37). All plasmids were transformed into E. coli strain BL21/DE3 (EMD Biosciences) for recombinant enzyme studies.

For recombinant protein production, E. coli cultures were grown at 37° C. to an optical density of 0.6 at 600 nm, then induced with 0.5 mM IPTG and allowed to grow 5 additional hours at 25° C. Cells were harvested by centrifugation at approximately 3000×g for 20 min at 4° C., washed with cold 0.9% NaCl, then collected by re-centrifugation at 3000×g. Pellets were resuspended in cold lysis buffer (100 mM potassium phosphate, pH 7.0, 1 M NaCl, 5 mM imidazole, 10% glycerol, 1 µg/ml leupeptin) and extracted using a French Press at a pressure of 1500 p.s.i. Benzonase (25 U/ml) and 1 mM PMSF were added immediately to the lysate. After 15 min incubation at room temperature, the lysate was centrifuged at 15,000×g for 20 min, and supernatant was loaded onto a Ni-column activated with 2 ml of 0.1 M NiSO4 and washed with 10 ml of distilled water. The Ni-column was previously equilibrated with 10 ml buffer A (100 mM potassium phosphate, pH 7.0, 500 mM NaCl, 5 mM imidazole). The column was washed with 3.5 ml buffer A between each 2 ml of supernatant. After the whole sample was loaded, the column was washed with 8 ml of buffer A followed with 8 ml of buffer B (100 mM potassium phosphate, pH 7.0, 500 mM NaCl, 50 mM imidazole). Recombinant polyketide synthases were then eluted with 2.5 ml of elution buffer (100 mM potassium phosphate, pH 7.0, 500 mM NaCl, 250 mM imidazole). The recombinant protein-containing fraction. (250 mM imidazole) was desalted on a PD-10 column equilibrated with cold desalting buffer (100 mM potassium phosphate, pH 7.0, 10 mM DTT, 10% glycerol). Protein concentrations were determined using a Bio-Rad protein assay kit (Bio-Rad Laboratories, Hercules, Calif.). Enzyme preparations were stored at −80° C. prior to use.

Example 5

Polyketide Synthase Enzyme Assays

Polyketide synthase enzyme assays, performed in triplicate, contained 100 mM potassium phosphate buffer (pH 7.0), 40 µM malonyl-CoA, 25 µM starter unit (e.g., palmitoyl-CoA), and 2 µg protein in a 200 µL volume at 30° C. for 15 min. Temperature and buffer pH optima for ARS1/2-containing assays were determined to be 30° C. and pH 7.0, respectively, and protein concentrations and time points used for activity measurements were controlled to insure linearity of the assays. Reactions were quenched by addition of 10 µL of 20% HCl, and products were extracted by phase partitioning with 1 ml of ethyl acetate. The organic phase (upper layer) obtained by centrifugation at ~14,000×g for 1 min was transferred to a fresh tube, dried under vacuum, and subsequently analyzed by GC-EI-MS as a trimethysilyl (TMS) derivative. Product formation was quantified using selective ion monitoring at m/z 268, a fragment ion common to all alkylresorcinols, generated by benzylic cleavage of the alkyl side chain. The identification of the m/z 268 [(5-methyl-1,3 phenylene)bis(oxy)bis(TMS)]$^+$ base ion and the parent [M]$^+$ provide confirmation of the 5-alkylresorcinolic structure as well as the length and degree of saturation of the associated side chain (Occolowitz, 1964. *Anal. Chem.* 36:2177-2181; Suzuki et al. 1996, supra; Suzuki at al. 2003, supra). Spectral data obtained for all identified alkylresorcinolic products are provided in Table 1. Further confirmation for the formation of olivetol (AR5:0) and pentadecylresorcinol (AR15:0) in assays provided with hexanoly- and palmitoly-CoA starters was obtained by comparison of product retention times and mass spectra relative to authentic standards. GC-EI-MS: AR5:0—R$_t$ 5.40 min, m/z 324 [M]$^+$, m/z 309 [M-CH$_3$]$^+$, m/z 295 [5-propyl-1,3-phenylene)bis(oxy)bis(TMS)]$^+$, m/z 281 [(5-ethyl-1,3-phenylene)bis(oxy)bis(TMS)]$^+$, m/z 268 [(5-methyl-1,3-phenylene)bis(oxy)bis(TMS)]$^+$; AR15:0—R$_t$ 10.17 min, m/z 464 [M]$^+$, m/z 449 [M-CH$_3$]$^+$, m/z 361 [449$^+$-2(CH$_2$)]$^+$, m/z 361 [449$^+$-OTMS, +H]$^+$, m/z 323 [5-pentyl-1,3-phenylene)bis(oxy)bis(TMS)+H]$^+$, m/z 310 [5-butyl-1,3-phenylene)bis(oxy)bis(TMS)]$^+$, m/z 310 [5-propyl-1,3-phenylene)bis(oxy)bis(TMS)]$^+$, m/z 281 [5-ethyl-1,3-phenylene)bis(oxy)bis(TMS)]$^+$, m/z 268 [5-methyl-1,3-phenylene)bis(oxy)bis(TMS)]$^+$, m/z 253 [268$^+$-CH$_3$]$^+$.

TABLE 1

Mass Spectral Characteristics of 5-Alykylresorcinols produced in ARS1, ARS2, Os05g12180, Os10g08620, and Os10g07040 Enzymatic Assays

| Acyl-CoA Starter | Product | m/z | Difference (amu)[a] |
|---|---|---|---|
| C6:0[b] | 5-pentyl resorcinol (AR5:0; C$_{11}$H$_{16}$O$_2$) | 324 [M]$^+$ | 56 |
| C8:0 | 5-heptyl resorcinol (AR7:0; C$_{13}$H$_{20}$O$_2$) | 352 [M]$^+$ | 84 |
| C10:0 | 5-nonyl resorcinol (AR9:0; C$_{15}$H$_{24}$O$_2$) | 380 [M]$^+$ | 112 |
| C12:0 | 5-undecyl resorcinol (AR11:0; C$_{17}$H$_{28}$O$_2$) | 408 [M]$^+$ | 140 |
| C14:0 | 5-tridecyl resorcinol (AR13:0; C$_{19}$H$_{32}$O$_2$) | 436 [M]$^+$ | 168 |
| C16:0 | 5-pentadecyl resorcinol (AR15:0; C$_{21}$H$_{36}$O$_2$) | 464 [M]$^+$ | 196 |
| C16:1 | 5-pentadecenyl resorcinol (AR15:1; C$_{21}$H$_{34}$O$_2$) | 462 [M]$^+$ | 194 |
| C16:3 | 5-pentadecatrienyl resorcinol (AR15:3; C$_{21}$H$_{30}$O$_2$) | 458 [M]$^+$ | 190 |
| C18:0 | 5-heptadecyl resorcinol (AR17:0; C$_{23}$H$_{40}$O$_2$) | 492 [M]$^+$ | 224 |
| C18:1 | 5-heptadecenyl resorcinol (AR17:1; C$_{23}$H$_{38}$O$_2$) | 490 [M]$^+$ | 222 |
| C18:2 | 5-heptadecadienyl resorcinol (AR17:2; C$_{23}$H$_{36}$O$_2$) | 488 [M]$^+$ | 220 |
| C20:0 | 5-nonadecyl resorcinol (AR19:0; C$_{25}$H$_{44}$O$_2$) | 520 [M]$^+$ | 252 |
| C20:4[b] | 5-nonadecatetraenyl resorcinol (AR19:4; C$_{25}$H$_{36}$O$_2$) | 512 [M]$^+$ | 244 |

[a]Difference denotes the mass value inferred by subtraction of the m/z 268 [(5-methyl-1,3 phenylene)bis(oxy)bis-(trimethylsilane)]$^+$ base ion from the [M]$^+$.
[b]Those substrates not utilized by Os05g12180, Os10g08620, or Os10g07040 are indicated.

Enzyme assays, performed in triplicate, for starter unit CoA kinetics contained 100 mM potassium phosphate buffer (pH 7.0), 40 µM [2-$^{14}$C]-malonyl-CoA (50-60 mCi/mmol, 1.85-2.22 GBq/mmol; American Radiolabeled Chemicals, Inc., St. Louis, Mo.), 1.43-10 µM starter unit (e.g., palmitoyl- CoA), and 0.75 μg protein in a 200 μL volume at 30° C. for 5 min. Enzyme assays for malonyl-CoA kinetics contained 100 mM potassium phosphate buffer (pH 7.0), 1.66-25 μM [2-$^{14}$C]-malonyl-CoA, 25 μM starter unit (palmitoleoyl-CoA), and 0.75 μg protein in a 200 μL volume at 30° C. for 5 min. Reactions were quenched by addition of 10 μL of 20% HCl. The products were extracted as described above, and were separated by thin layer chromatography (silica gel 60 F$_{254}$; chloroform:ethyl acetate=70:30; 15 min). Product detection and formation was quantified through the use of the Cyclone storage phosphor system and OptiQuant 3.0 image analysis software (PerkinElmer, Wellesley, Mass.). Data were fit to the Michaelis-Menten equation using the Sigma Plot 9.01 enzyme kinetics module (Systat, Inc., San Jose, Calif.). Thin layer chromatographs of ARS1, ARS2, Os05g12180, Os10g08620, and Os10g07040 reaction products in assays using saturated acyl-CoA substrates from hexanoyl-CoA (C6) to myristoyl-CoA (C14) revealed the formation of secondary products, which were subsequently identified by GC-EI-MS as triketide pyrones from the mass spectrum of the peaks appearing in reconstructed ion chromatograms, supported by the appearance of fragment ions characteristic of the specific triketide pyrone. GC-EI-MS (starter substrate, m/z triketide pyrone): hexanoly-CoA (C6), m/z 254 [M]$^+$, m/z 239 [M–CH$_3$]$^+$, m/z 224 [M-CO, -2H]$^+$, m/z 195 [M-CO, -2(CH$_3$), +H]$^+$, m/z 211 [3-OTMS-5-methylfuran, —H]$^+$; capryloyl-CoA (C8), m/z 282 [M]$^+$, m/z 253 [M-CO, —H]$^+$, m/z 211 [M-TMS, +2H]$^+$, m/z 166 [282$^+$-CO, -OTMS]$^+$, m/z 139 [166$^+$-CO, +H]$^+$; caproyl-CoA (C10), m/z 311 [M+H]$^+$, m/z 281 [M-CO, —H]$^+$, m/z 221 [M-OTMS]$^+$, m/z 191 [281$^+$-OTMS, —H]$^+$; lauroyl-CoA (C12), m/z 337 [M–H]$^+$, m/z 312 [M-CO, +2H]$^+$, 325 [M-CH$_3$, +2H]$^+$, m/z 249 [M-OTMS]$^+$, m/z 221 [249$^+$-CO]$^+$, m/z 197 [221$^+$-CO+H]$^+$; myristoyl-CoA (C14), m/z 366 [M]$^+$, m/z 351 [M-CH$_3$]$^+$, m/z 221 [M-C$_2$O$_2$H-OTMS]+, m/z 207 [221+–CH$_2$]+, m/z 170 [3-OTMS-5-methylfuran]$^+$.

Recombinant enzyme studies were next performed to examine substrate preferences for the 3 putative type III PKS enzymes maximally expressed in root hairs. The full-length ORFs determined for the sequences 2_127, 2_126 and 0_1848 were over-expressed in E. coli as N-terminal polyhistidine fusions, and purified by Ni$^{2+}$ affinity chromatography. Acyl-CoAs varying in length and degree of saturation were tested in enzymatic assays with all three recombinant enzymes, as well as the non-linear starter units benzoyl-CoA, isovaleryl-CoA, and isobutryl-CoA used by several other plant type III PKS enzymes (Austin and Noel, supra). Trimethylsilyl (TMS) derivatized products were detected by GC-MS selective ion monitoring at m/z 268 for the quantification of 5-alkyresorcinols, as previously described (Suzuki et al. 2003. Bioorg. Chem. 31:437-452).

Figure 4:
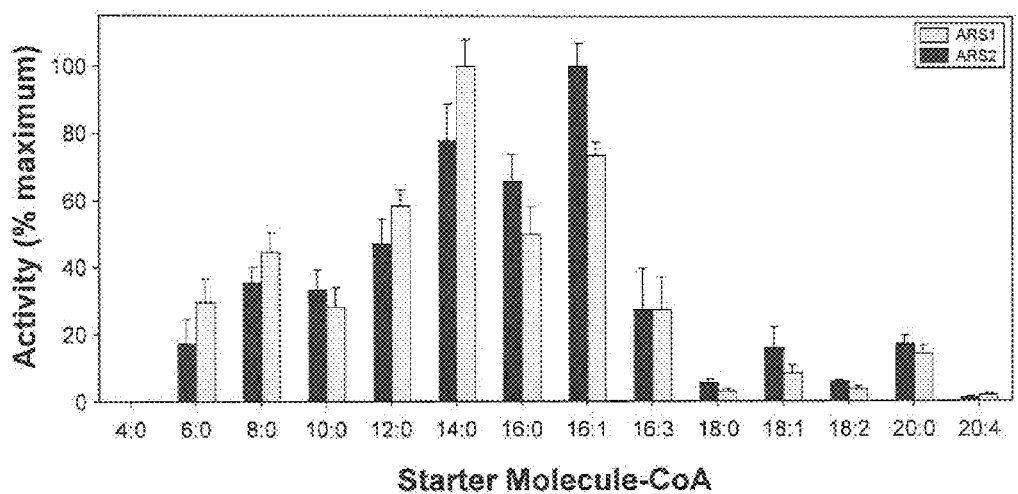
FIG. 4 depicts the enzymatic activities of recombinant ARS1 and ARS2. Relative activities were determined for recombinant ARS1 and ARS1 in assays using acyl-CoA starter units varying in chain length and degree of saturation For these experiments, the full-length ORFs determined for the sequences 2_126 (ARS1) and 2_127 (ARS2) were heterologously expressed as N-terminal polyhistidine fusions in *E. coli*, then purified by affinity chromatography. Data are expressed as relative mean±SD from assays performed in triplicate.

The results of the recombinant enzyme assays with the enzymes encoded by 2_126 and 2_127 are shown in FIG. 4. Both enzymes were able to catalyze the formation of 5-alkylresorcinols using various fatty acyl-CoA starter units with malonyl-CoA as the extender unit, and will therefore be, hereafter referred to as ARS1 (Alkyl Resorcinol Synthase) and ARS2, respectively (FIG. 4). Overall, the activity profiles exhibited by ARS1 and ARS2 were quite similar; for example, nearly overlapping profiles were obtained for fatty acyl-CoA starter units possessing saturated chains ranging in length from C6 (hexanoyl-CoA) to C20 (arachidoyl-CoA; FIG. 4). Furthermore, similar preferences were observed for both enzymes among the unsaturated acyl-CoA substrates palmitoleoyl-CoA (C16:1Δ$^9$), hexadecatrienyl-CoA (C16:3Δ$^{9,12,15}$), oleoyl-CoA (C18:1Δ$^9$), linoleoyl-CoA (C18:2Δ$^{9,12}$), and arachidonoyl-CoA (C20:4Δ$^{5,8,11,14}$), with maximal activities observed with palmitoleoyl-CoA (FIG. 4). Among all the acyl-CoAs evaluated, maximal 5-alkylresorcinol-forming activity was observed with myristoyl-CoA (C14) and palmitoleoyl-CoA (C16:1Δ$^9$) for ARS1 and ARS2, respectively, and these starter units represented the two most highly preferred substrates for both enzymes. No activity was observed for either ARS1 or ARS2 when benzoyl-CoA, isovaleryl-CoA, or isobutyryl-CoA were provided as starter units (data not shown).

Figure 13:
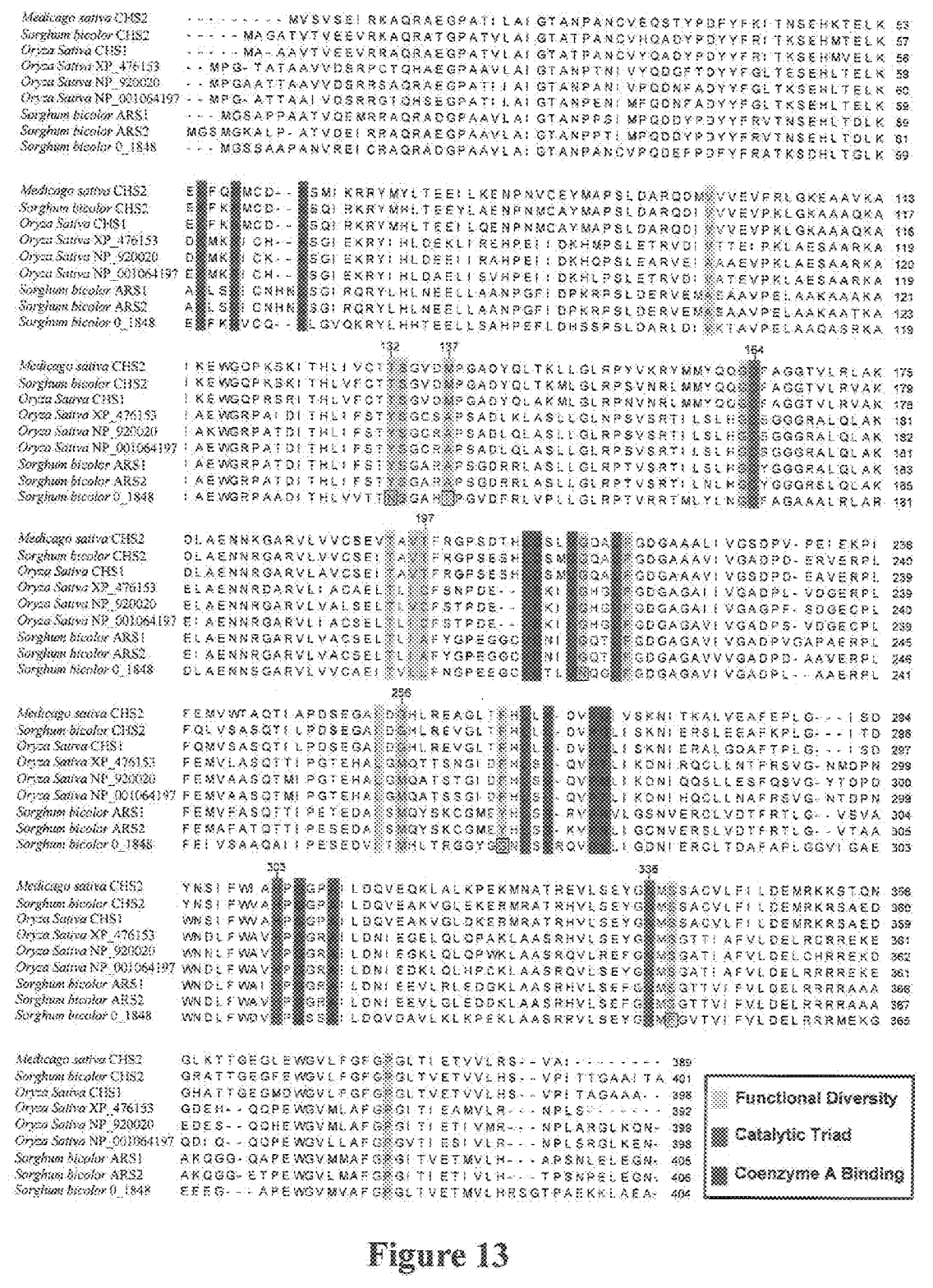

The recombinant PKS-like protein encoded by root hair contig 0_1848 exhibited no activity with any of the substrates analyzed, despite associating with the soluble fraction of the E. coli protein extracts and migrating at the expected position in SDS-PAGE analysis. Presumably 0_1848 encodes a non-functional protein, or the enzyme does not act on any of the substrates used in the present work. The comparison of the predicted 0_1848 ORF sequence with other type III plant PKS enzymes (including ARS1 and ARS2) did indeed reveal several differences in positions known to affect substrate specificity and contributing to the functional diversification of this family of enzymes (Austin and Noel, supra; FIG. 3). The potential significance of these differences was further underscored from sequence comparisons which included three additional proteins from rice exhibiting ARS activity (FIG. 13). These amino acid substitutions could therefore account for either the inactivity of, or alternatively, for a different catalytic function of the 0_1848-encoded polypeptide.

Evaluation of steady-state kinetic parameters for reaction of ARS1 and ARS2 with the starter units palmitoyl-CoA (C16) and palmitoleoyl-CoA (C16:1), as well as the malonyl-CoA extender (Table 2), indicated k$_{cat}$ and k$_{cat}$/k$_m$ values in range with those obtained for other type III plant PKSs utilizing preferred substrates (e.g., Jez et al., supra; Liu et al. 2003. Plant J. 34:847-855; Abe et al. 2005b, supra; Katsuyama et al. 2009. J. Biol. Chem. 284:11160-11170; Taura et al., 2009. FEBS Lett. 583:2061-2066). A single derailment product was observed for ARS1 and ARS2 in enzyme assays using saturated acyl-CoA substrates from hexanoyl-CoA (C6) to myristoyl-CoA (C14), which was not detectable for substrates longer than C14. Analysis of the total ion chromatograms and mass spectra from the corresponding enzymatic assays revealed characteristic parent and fragment ions supporting the identification of these derailment products as triketide pyrones. For ARS1, the triketide pyrone constituted approximately 9% of the total moles product derived from hexanoyl-CoA, 33% of the product derived from capryloyl-CoA (C8), 20-22% of the products derived from caproyl-(C10) and lauroyl-CoA (C12), and 15% of the product derived from myristoyl-CoA. For ARS2, the triketide pyrone constituted approximately 9% of the total moles product derived from hexanoyl-CoA, 19-24% of the product derived from capryloyl-(C8), lauroyl-(C12), and caproyl-CoA (C10), and <5% of the product derived from myristoyl-CoA.

TABLE 2

Kinetic Parameters for Recombinant ARS1 and ARS2 with C16:0 and C16:1 Starter Units and Malonyl-CoA Extender

| | ARS1 | | | ARS2 | | |
|---|---|---|---|---|---|---|
| Substrate | k$_{cat}$ (min$^{-1}$) | K$_m$ (μM) | k$_{cat}$/K$_m$ (M$^{-1}$ s$^{-1}$) | k$_{cat}$ (min$^{-1}$) | K$_m$ (μM) | k$_{cat}$/K$_m$ (M$^{-1}$ s$^{-1}$) |
| C16:0-CoA | 0.79 | 2.3 ± 1.0 | 5656 | 1.1 | 4.1 ± 1.0 | 4520 |

TABLE 2-continued

Kinetic Parameters for Recombinant ARS1 and ARS2 with C16:0 and C16:1 Starter Units and Malonyl-CoA Extender

| Substrate | ARS1 | | | ARS2 | | |
|---|---|---|---|---|---|---|
| | $k_{cat}$ (min$^{-1}$) | $K_m$ (µM) | $k_{cat}/K_m$ (M$^{-1}$ s$^{-1}$) | $k_{cat}$ (min$^{-1}$) | $K_m$ (µM) | $k_{cat}/K_m$ (M$^{-1}$ s$^{-1}$) |
| C16:1-CoA | 1.1 | 2.3 ± 1.1 | 7680 | 1.4 | 3.6 ± 1.1 | 6201 |
| Malonyl-CoA | 0.89 | 5.2 ± 0.9 | 2842 | 0.74 | 5.8 ± 1.3 | 2149 |

Importantly, both recombinant ARS1 and ARS2 enzymes utilized hexadecatrienyl-CoA (C16:3$\Delta^{9,12,15}$), the physiological substrate proposed for alkylresorcinol synthases participating in sorgoleone biosynthesis (FIG. 1), although higher activities were obtained for both enzymes using substrates such as palmitoyl-CoA (C16) and palmitoleoyl-CoA (C16:1) (FIG. 4). Such starter units would be predicted to generate congeners of sorgoleone possessing C15:0 and C15:1$\Delta^8$ alkyl side chains in vivo, allowing that subsequent O-methylation and di-hydroxylation could proceed in root hairs. Sorgoleone congeners possessing C15:0 and C15:1$\Delta^8$ side chains have in fact been identified in sorghum root exudates, but only as minor constituents (Kagan et al., supra), despite the fact that fatty acid methyl ester (FAME) profiling of *S. bicolor* (genotype BTx623) root hairs has shown that palmitate (C16:0) and palmitoleate (C16:1) are far more abundant than C16:3 fatty acids in this cell type (Pan et al., supra). While the possibility cannot be eliminated that ARS1 and ARS2 are dedicated to the biosynthesis of minor exudate constituents rather than sorgoleone, this would seem somewhat unlikely given that their transcripts represent the two most highly expressed PKS-like sequences in *S. bicolor* root hairs, each accounting for approximately 0.055% of all transcripts based on EST counts (Baerson et al. 2008a, supra), and no other PKS-like sequences encoding alkylresorcinol synthases were identified among the 5,468 root hair ESTs analyzed.

Example 6

Plant Transformation

Phenolic Lipid (Sorgoleone) Production in Transgenic *Arabidopsis*

To test for the production of phenolic lipids in transgenic plants by expression of sorghum PKSs ARS1 or ARS2, binary vectors were developed for expression of these sequences in planta (FIG. 5). For this approach, the complete open reading frames of ARS1 or ARS2 were positioned downstream of an enhanced CaMV 35S promoter (Kay et al. 1987. *Science* 236:1299-1302), and directly upstream of the CaMV 35S transcript polyadenylation region. In addition, the 5' untranslated region of the Tobacco Etch Virus (TEV) was positioned directly upstream of the ARS1 and ARS2 coding sequences to enhance translation (Carrington and Freed. 1990. *J. Virol.* 64:1590-1597). The ARS1 and ARS2 overexpression transgene cassettes were cloned within the T-DNA borders of the binary vector pZP212 (Hajdukiewicz et al. 1994. *Plant Mol. Biol.* 25:989). The resulting constructs, shown in FIG. 5, contain the expression cassettes arranged in a head-to-tail orientation with respect to the NPTII selectable-marker cassette, and were designated pZP212_ARS1 and pZP212_ARS2. All DNA manipulations involved in the construction of pZP212_ARS1 and pZP212_ARS2 involved standard cloning procedures (Sambrook et al., supra). Recombinant *A. tumefaciens* strains harboring pZP212_ARS1 and pZP212_ARS2, or the parent ('empty') vector control were used to transform *Arabidopsis thaliana* (cv. Col-0) using the 'floral-dip' procedure (Clough and Bent. 1998. *Plant J.* 16:735-743), and transgenic $T_1$ individuals were identified by selection on MS plates containing 50 µg/ml kanamycin. Twenty five to twenty eight-day-old $T_2$ generation seedlings were used for all chemical analyses described.

For experiments involving ARS1 and ARS2 overexpression in *Arabidopsis* plants, expression of both transgene cassettes in the various transgenic lines generated was confirmed by quantitative real-time PCR analyses, performed using leaf tissues samples as previously described (Baerson et al. 2005, supra). Total RNAs prepared for use in real-time PCR assays were isolated from flash-frozen, pulverized transgenic leaf samples using the RNeasy Plant Mini-Kit (Qiagen Inc., Valencia, Calif.), including an additional homogenization step of 30 s at 25,000 rpm using a handheld homogenizer. RNA recovery and purity were determined spectrophotometrically, and sample integrity was assessed by agarose gel electrophoresis.

All real-time PCR reactions were performed in triplicate using a GenAmp® 7300 Sequence Detection System (Applied Biosystems, Foster City, Calif.). First strand cDNAs were synthesized from 2 µg of total RNA in a 100 mL reaction volume using the TaqMan Reverse Transcription Reagents Kit (Applied Biosystems) per manufacturer's instructions. Independent PCR reactions were performed using the same cDNA for both the gene of interest (ARS1 or ARS2) and 18S rRNA, using the SYBR® Green PCR Master Mix (Applied Biosystems) with the following primer pairs: ARS1 or ARS2—forward: 5'-GAGTTTGGCAACATGAGTGGC-3' (SEQ ID NO:38), reverse: 5'-TCATCG AGCACGAAGAT-CACC-3'(SEQ ID NO:39); 18S rRNA—forward: 5'-GGCTCGAAGAC GATCAGATACC-3'(SEQ ID NO:40), reverse: 5'-TCGGCATCGTTTATGGTT-3'(SEQ ID NO:41). Due to the high degree of nucleotide identity between ARS1 and ARS2, one primer pair was designed which was complementary to both sequences. Primers were designed using Primer Express® software (Applied Biosystems) and the Amplify program (Engels W R., supra). A dissociation curve was generated at the end of each PCR cycle to verify that a single product was amplified using software provided with the GeneAmp® 7300 sequence detection system. A negative control reaction in the absence of template (no template control) was also routinely performed in triplicate for each primer pair. The change in fluorescence of SYBR® Green I dye in every cycle was monitored by the GenAmp® 7300 system software, and the threshold cycle ($C_T$) above background for each reaction was calculated. The $C_T$ value of 18S rRNA was subtracted from that of the gene of interest to obtain a $\Delta C_T$ value. The $C_T$ value of an arbitrary calibrator (e.g., the tissue sample from which the largest $\Delta C_T$ values were obtained) was subtracted from the $\Delta C_T$ value to obtain a $\Delta\Delta C_T$ value. The fold-changes in expression level relative to the calibrator were expressed as $2^{-\Delta\Delta C_T}$.

As is the case for the majority of type III PKS enzymes, ARS1 and ARS2 can both utilize malonyl-CoA as the extender substrate, a compound ubiquitously present in plant tissues. Furthermore ARS1 and ARS2 can both utilize fatty acyl-CoAs of various chain lengths as starter units, directly leading to the formation phenolic lipids possessing resorcinolic head groups. In leaf tissues of *Arabidopsis thaliana*, palmitoyl-CoA (16:0) represents one of the predominant acyl-CoA pools (Browse and Somerville. 1991. *Annu. Rev.*

Figure 6:
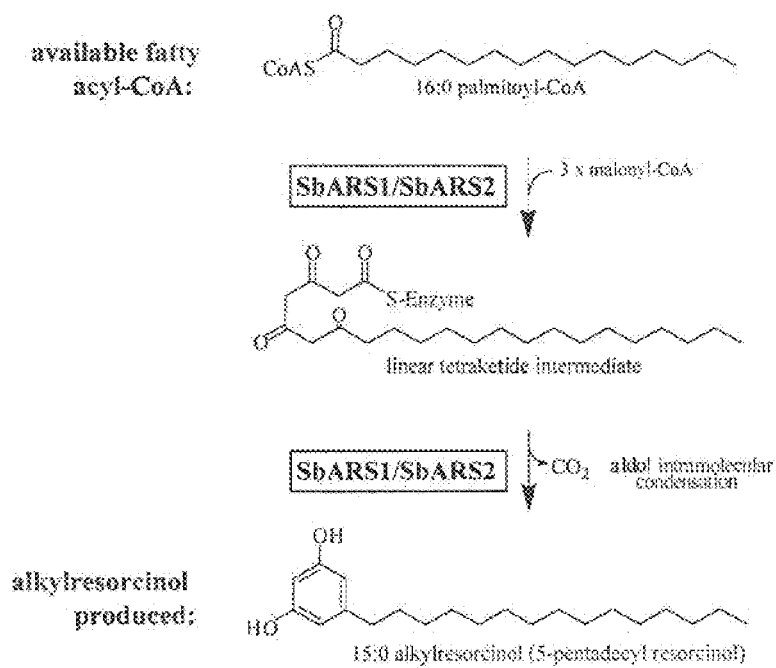
FIG. 6 shows the predicted reaction product for sorghum PKSs ARS1 or ARS2 expressed in *Arabidopsis* leaves utilizing available palmitoyl- and malonyl-CoA as substrates.

*Plant Physiol. Plant Mol. Biol.* 42: 467-506), thus a C15:0 alkylresorcinol would be predicted to accumulate in leaf tissues ARS1 or ARS2-overexpressing *Arabidopsis* transformants (FIG. 6).

To assess whether C15:0 alkylresorcinol (5-pentadecyl resorcinol) was produced in plants harboring pZP212_ARS1 or pZP212_ARS2 (FIG. 5), leaf tissues were harvested and pooled from 10-15 3-week old $T_1$ seedlings per line, and analyzed by gas chromatography/mass spectrometry (GC-MS). Flash-frozen, pulverized tissues (50 mg) were first homogenized in 1.0 ml chloroform, and homogenates were then filtered through Whatman No. 1 filter discs, then evaporated using a rotary evaporator (Büchi Rotovapor, Brinkmann Instruments) at 30° C. Products were analyzed as trimethysilyl derivatives using a JEOL GCMate II System (JEOL USA Inc., Peabody, Mass.) using a J&W DB-5 capillary column (0.25 mm internal diameter, 0.25 mm film thickness, 30 m length; Agilent Technologies, Foster City, Calif.). Product formation was quantified using selective ion monitoring at m/z 268, a common fragment to all alkylresorcinols. The identity of the product formed was verified by their retention times and mass specta relative to authentic standards for pentadecylresorcinol (Chem Service Inc., West Chester, Pa.).

The results of both the quantitative real-time PCR gene expression assays and C15:0 alkylresorcinol analyses are shown in FIG. 7. Five independent *Arabidopsis* lines transformed using the pZP212_ARS1 binary vector, and 5 lines transformed using pZP212_ARS2, were screened for expression of the 35S::ARS1 and 35S::ARS2 transcripts, respectively, as well as for the presence of the C15:0 alkylresorcinol. Due to the extensive sequence identity shared between the ARS1 and ARS2 coding sequences, the same real-time PCR assay was used to monitor both 35S::ARS1 and 35S::ARS2 transcript levels, thus their relative expression could be directly compared (FIG. 7A). As is typically seen in transformed plant populations, significant variation was observed in transcript accumulation levels among the various transformants. Importantly, in the three lines exhibiting the highest relative transgene expression levels (PKS40-8, PKS44-13, PKS44-14), significant accumulation of the C15:0 alkylresorcinol (5-pentadecyl resorcinol) was also detected by GC-MS (FIG. 7B). Of further interest, the relative levels of alkylresorcinol detected in these three lines (ranging from approximately 1.2 to 4.8 ng/mg fresh weight), roughly paralleled their respective transgene expression levels (compare FIGS. 7A and 7B), suggesting that higher C15:0 alkylresorcinol levels could be achievable via increased ARS1 and ARS2 expression in planta. Additionally, while lower transgene expression levels were detected among several of the lines in which alkylresorcinol was not detected, it is possible that C15:0 did accumulate to levels below the limit of detection of the GC-MS procedures employed.

These experiments demonstrate a utility of the invention described herein: transgenic plants expressing polyketide synthases such as ARS1 or ARS2 from *Sorghum bicolor* accumulate alkylresorcinols by utilizing available host fatty acyl-CoA and malonyl-CoA pools. The ability ALRS1 and ARS2 to efficiently utilize fatty acyl-CoA substrates in planta yielding phenolic lipids such as 5-pentadecyl resorcinol (FIG. 6) is a central feature of this technology. In this *Arabidopsis* transgenic experiment, we are actually detecting the production of 5-pentadecyl resorcinol here because *Arabidopsis* lacks the 16:3 fatty acyl-CoA precursor found in sorghum root hair cells. The present proof-of-concept represents a relatively simple test case, which can be further optimized for the production of phenolic lipids at higher levels or in specific tissues, for example, by the use of alternative promoter elements or other genetic elements required for the optimal expression of the transgene cassettes employed. It is anticipated that these relatively straight-forward modifications would result in significant increases in phenolic lipid production, or in the production in specific plant organs such as developing seeds or fruits. Related polyketide synthase enzymes could also be identified with more favorable kinetics that could also significantly enhance compound production. Such alternative polyketide synthase sequences could be isolated from diverse species by virtue of their sequence similarity to ARS1 and ARS2 using standard molecular biology techniques. In addition, while in the present example both ARS1 and ARS2 transgene cassettes used the strong, constitutively-expressed CaMV 35S promoter (FIG. 5), gene promoters specifically induced by chemicals, pathogen infection, and other types of elicitors could be employed. In this case, the phenolic lipid would only be produced when crops are treated with specific chemical elicitors by growers, or automatically produced when plants are under attack by microorganisms or other adverse circumstances where phenolic lipid production would be beneficial to overall crop yields.

Example 7

Binary Vector Construction

Analysis of pARS1-RNAi and pARS-RNAi Transgenic Events

Hairpin RNA-forming binary vectors were developed for RNAi-mediated repression of ARS1 (SEQ ID NO:1) and ARS2 (SEQ ID NO:3) using target regions of 602 and 556 bp in length, respectively, cloned in both sense and antisense orientation, separated by a 1.13 kb intron sequence derived from the *Arabidopsis* FAD2 gene (Okuley of al., supra) and positioned downstream of the constitutive polyubiquitin-1 promoter from *Zea mays* with its cognate intron (Christensen et al., supra). The specific target sequences selected for ARS1 correspond to nucleotides 758-1215 (3' end) of the coding sequence plus an additional 145 bp of contiguous 3' UTR sequence; the specific target sequences selected for ARS2 correspond to nucleotides 762-1218 (3' end) of the coding sequence plus an additional 100 bp of contiguous 3' UTR sequence. The target regions chosen represent just one example of ARS1 and ARS2 gene sequences useful for RNAi-mediated repression of phenolic lipid synthesis in sorghum, however in principle any transcribed region from these genes could be used with potentially similar efficacy.

To minimize the possibility of off-target silencing of related sequences, all publicly-available genomic and EST sequence data for *S. bicolor* were analyzed to avoid target sequences containing regions possessing ≥21 nt of contiguous identity with other gene coding sequences (Xu of al. 2006. *Plant Physiol*. 142:429-440). It is important to take into account that the sequences for ARS1 and ARS2 are closely related, sharing 93% overall nucleotide sequence identity within coding regions, and within the chosen RNAi target regions share approximately 80% identity, including numerous contiguous stretches >21 nt in length of 100% identity. Thus, in principle, hairpin RNA (hpRNA) generated from either vector (FIG. 8) would be inhibitory to the expression of both ARS1 and ARS2, however, given the paucity of information concerning RNAi-mediated inhibition in sorghum, both vectors were tested in stable transformation experiments.

ARS1 and ARS2 target regions flanked by EcoRI (5' end) and BamHI (3' end) restriction sites were first generated by PCR amplification using *S. bicolor* (genotype Btx623) genomic DNA as template (described in 'Methods'), to facilitate direct ligation with EcoRI- and BamHI-digested pUbi-IF2 (DNA Cloning Service, Hamburg, Germany). The primer pairs used for these PCR amplifications were as follows: ARS1 forward, 5'-CCCTGAATTCAGACCACGATACC GGA-3' (SEQ ID NO: 42, and reverse, 5'-CTCTG GATCCT-TACGCACCGCCTTAT-3' (SEQ ID NO:43; ARS2 forward, 5'-CCCTGAATT CGACCACGATACCGGA-3' (SEQ ID NO:44, and reverse, 5'-CCCCGGATCCACCTT ATGGTC-CAT-3' (SEQ ID NO:45). The resulting intermediate constructs were then digested with BsrGI and MluI, and ARS1 and ARS2 target regions flanked by BsrGI (5' end) and MluI (3' end) were also generated in a second round of PCR amplifications as above. The primer pairs used for the second round of PCR amplifications were as follows: ARS1 forward, 5'-CCCTTG TACAGACCACGATACCGGA-3' (SEQ ID NO:46), and reverse, 5'-CTCTACGCGTTAC GCACCGC-CTTAT-3' (SEQ ID NO:47); ARS2 forward, 5'-CCTCtGTA-CAGACCACGAT ACCGGA-3' (SEQ ID NO:48), and reverse, 5'-CTCTACGCGTCCACCTTATGGTCCAT-3' (SEQ ID. NO:49). Following digestion with BsrGI and MluI, the PCR products were ligated with their corresponding intermediate vectors, resulting in the final intermediate vectors, pUbi-ARS1 and pUbi-ARS2 (not shown), containing the complete hpRNA-generating transgene cassettes for ARS1 and ARS2 as confirmed by DNA sequence analysis. Finally, pUbi-ARS1 and pUbi-ARS2 were digested with SfiI, then the approximately 4.0 kb RNAi cassette-containing fragments were gel-purified and ligated with SfiI-digested pLH9000 (Hausmann and Töepfer, supra). The resulting binary vectors contain the hpRNA-generating cassettes arranged in a head-to-tail orientation with respect to the nptII selectable-marker cassette, and were designated pARS1-RNAi and pARS2-RNAi (FIG. 8). All DNA manipulations involved in the construction of pARS1-RNAi and pARS2-RNAi involved standard cloning procedures (Sambrook et al., supra). For the generation of transgenic *S. bicolor* events, recombinant *A. tumefaciens* strains (NTL4/Chry5) harboring pARS1-RNAi and pARS2-RNAi were prepared, and used to transform immature embryos of *Sorghum bicolor* (genotype Tx430) as previously described (Howe et al. 2006. Plant Cell Rep. 25:784-791).

To confirm expression of the hpRNA in the various transgenic events, 30 $T_1$ seeds were sown per event in perlite (Hummert's, Earth City, Mo.) saturated with 0.5× Hoagland's solution (Sigma-Aldrich, St. Louis, Mo.), and maintained for 10 days at 25° C. in a growth chamber under a 16 h photoperiod, and light intensity of approximately 400 μmole $m^{-2}s^{-1}$. On day 10, the perlite was gently removed and root systems from each seedling were individually numbered and harvested into 3.0 mL polypropylene tubes, flash-frozen in liquid nitrogen, then stored at −80° C. prior to use. As a control, root systems were also harvested from non-transformed *S. bicolor* genotype Tx430 seedlings grown in an identical manner.

For detection of transgene-derived hpRNA transcripts, individual root systems were first hand-pulverized using a mortar and pestle, then 10 mg tissue aliquots from each root system were used for total RNA extractions. Total RNAs were prepared using an RNeasy Plant Mini-Kit (Qiagen Inc., Valencia, Calif.) with the inclusion of an additional homogenization step of 30 s at 25,000 rpm using a handheld homogenizer to aid tissue disruption, and an "on column" DNase I treatment using a RNase-Free DNase kit as per manufacturer's instructions, to remove residual DNA contamination (Qiagen, Inc., Valencia, Calif.). RNA recovery and purity were determined spectrophotometrically, and sample integrity was assessed by agarose gel electrophoresis. Eight different transgenic events were initially screened for hpRNA expression (4 transformed with pARS1-RNAi and 4 transformed with pARS2-RNAi), thus a total of 240 root systems (30 seedlings per event) were independently analyzed in triplicate assays by quantitative real-time RT-PCR. To distinguish the transgene-derived hpRNA transcripts from endogenous ARS1 and ARS2 transcripts, the reverse primer used for real-time PCR assays was complementary to sequences within the octopine synthase (OCS) polyadenylation region immediately adjacent to the RNAi target sequences within pARS1-RNAi and pARS2-RNAi (FIG. 8). Since identical OCS polyadenylation regions were present in both vectors, the same reverse primer (5'-CGCATATCT CATTAAAG-CAGGGTC-3'; SEQ ID NO:50) was used to screen both pARS1-RNAi and pARS2-RNAi transformants. For pARS1-RNAi transformants the forward primer used was 5'-CTCCT-TGTGGCTAATTCATGGAC-3'(SEQ ID NO:51), and for pARS2-RNAi transformants the forward primer used was 5'-CACATATATCGCCAATTCATGGAC-3' (SEQ ID NO:52).

Figure 9:
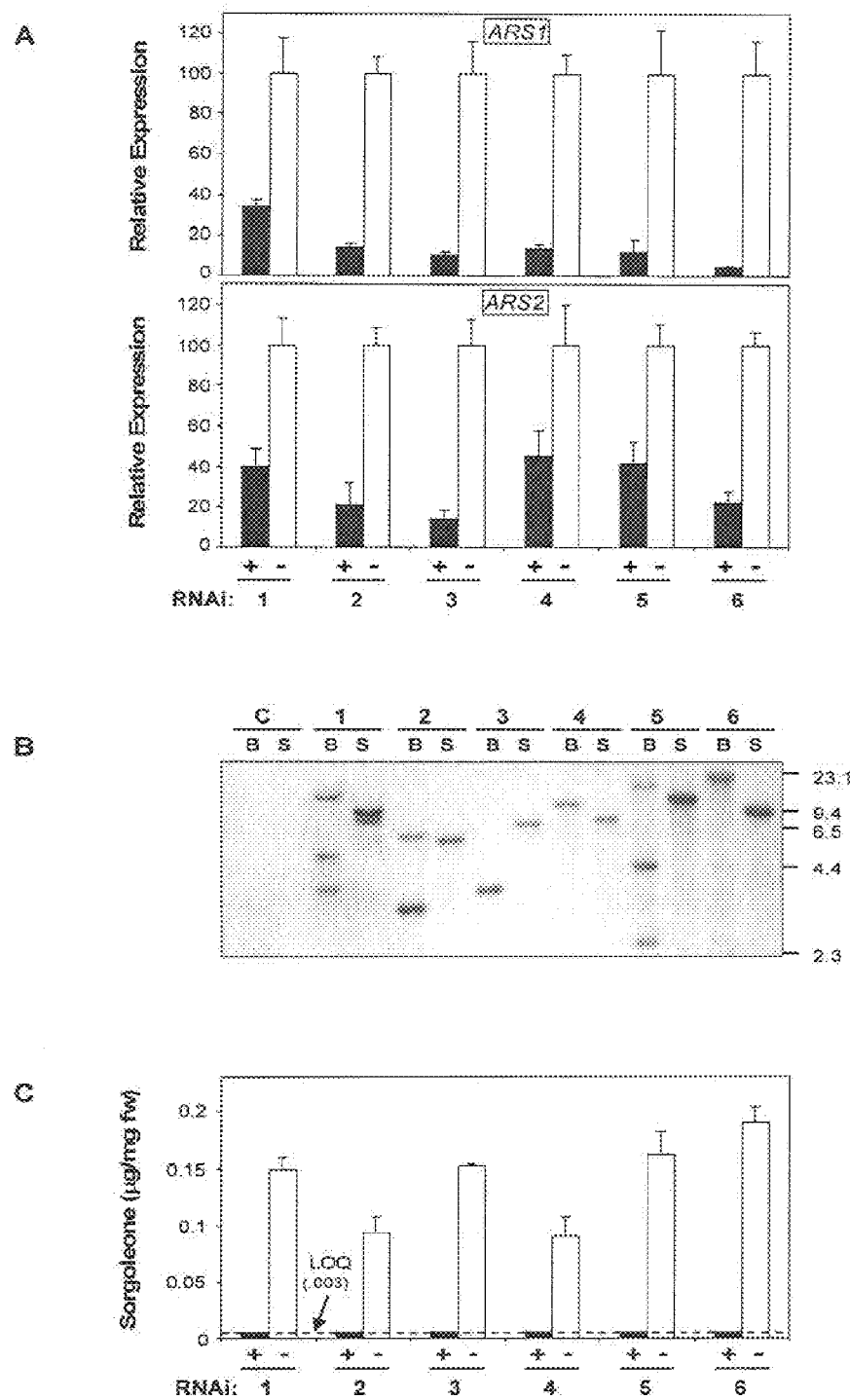
FIGS. 9A-9C depict the evaluation of *S. bicolor* RNAi transformant events.

Based on the real-time PCR analyses described above, individual seedlings were scored as either hpRNA "+" (hpRNA transcript detected) or hpRNA "−" (hpRNA transcript not detected). Within each transgenic event, equal samples from all hpRNA "+" individuals were pooled, and a second pool of tissues was similarly prepared from all hpRNA "−" individuals. The results for the analysis of the remaining transgenic events where hpRNA expression was detected are shown in FIG. 9. The expression levels for endogenous ARS1 and ARS2 transcripts in "+" and "−" individuals were independently assayed for each event by quantitative real-time RT-PCR using gene-specific primers as shown in FIG. 9A. In all events, ARS1 and ARS2 expression levels were significantly reduced in hpRNA "+" individuals relative to hpRNA "−", reflecting the successful down-regulation of ARS1 and ARS2 in hpRNA-expressing individuals. ARS1 silencing appeared somewhat more effective overall than ARS2, however sufficient sequence identity ostensibly existed between the 3' coding regions of the two genes to trigger silencing of both, as this was observed irrespective of the vector used (FIG. 9A). For these analyses, PCR primers were designed within coding sequences excluded from ARS1 and ARS2 RNAi-targeted regions, and were as follows: pARS1-RNAi transformants—forward, 5'-AGCTCCT-TGTGGCTAATTCATGG-3'(SEQ ID NO:53), reverse, 5'-TATAGGCACAAATACAATATAACACACTTGC-3' (SEQ ID NO:54); pARS2-RNAi transformants—forward, 5'-ATGGGGTCCATGGGGAAG-3'(SEQ ID NO:55), reverse, 5'-GGTGGCCGGTAGTGCCT-3'(SEQ ID NO:56). Reduction of ARS1 transcript accumulation in hpRNA "+" individuals ranged from approximately 66-96% relative to corresponding hpRNA "−" individuals for each event, and ARS2 transcript levels were reduced from approximately 55-86% (FIG. 9A). Complete loss of ARS1/2 expression was not observed for any event, however relatively few studies have employed real-time RT-PCR to quantify target inhibition in plant RNAi studies, thus it is somewhat difficult to draw direct comparisons at present.

Additionally, Southern analyses were performed to estimate the number of T-DNA loci in transformants. Southern analyses indicated approximately 1-2 T-DNAs per event, with 3 of the 6 events (events 3, 4, and 6) harboring a single T-DNA locus (FIG. 9B).

For T-DNA loci number estimates, genomic DNAs were extracted from leaves harvested from 10 day-old pARS1-RNAi or pARS2-RNAi *S. bicolor* transformants, as well as wild-type (genotype Tx430) seedlings using a DNeasy Plant Mini Kit (Qiagen, Valencia, Calif.) per manufacturer's instructions. Restriction endonuclease digestions and Southern blotting procedures were performed according to standard protocols (Sambrook et al., supra). Probe sequences corresponding to nucleotides 56-1129 of intron 1 from the *A. thaliana* FAD2 gene (FIG. 8) were generated by PCR amplification of pARS1-RNAi plasmid templates with PfuUltra DNA polymerase (Stratagene, La Jolla, Calif.), using a thermal profile of 95° C. for 30 s, then 60° C. for 30 s, followed by 72° C. for 90 s for 25 cycles. The PCR primer pair used for probe sequence amplification was forward: 5'-CCAG-TAGCTCCTGCTCTGTGAA-3'(SEQ ID NO:57), and reverse: 5'-TGCAGAAAACCAAAAGCAAAAG-3'(SEQ ID NO:58). The resulting PCR product was gel-purified, then radio-labeled with [α-$^{32}$F]-dCTP (6000 Ci/mmol, 20 mCi/mL; PerkinElmer, Waltham, Mass.) using a Rediprime II DNA Labeling Kit (GE Healthcare, Piscataway, N.J.). Membranes were hybridized at 65° C. for 16 h, washed twice for 10 min in 2×SSC, 0.2% SDS at 55° C.: then twice for 10 min in 0.2×SSC, 0.2% SDS at 65° C., followed by two additional washes for 20 min in 0.1×SSC, 0.1% SDS at 65° C., then subjected to autoradiography for approximately 18 h.

To determine whether hpRNA expression in roots correlated with inhibition of sorgoleone biosynthesis, all hpRNA "+" and "−" pooled samples were subjected to GC-MS (FIG. 9C), as described in 'Methods'. For determination of sorgoleone levels in transgenic *S. bicolor* (genotype Tx430) root tissues, 50 mg aliquots of flash frozen, pulverized tissues were first extracted by gentle swirling in 1 mL chloroform for 30 s, followed by centrifugation at 16,000×g for 10 min at 4° C. Supernatants were then collected and filtered through 0.22 μm Fluoropore PTFE membranes (Millipore, Billerica, Mass.) into tared vials, dried to completion under a stream of nitrogen gas, and weighed using an analytical balance. Dried extracts were then re-dissolved in chloroform, and analyzed by GC-MS on a JEOL GCMate II System (JEOL USA Inc., Peabody, Mass.) using a J&W DB-5 capillary column (0.25 mm internal diameter, 0.25 μm film thickness, 30 m length; Agilent Technologies, Foster City, Calif.). The GC temperature program was initially set to 210° C., raised to 310° C. at a rate of 4° C./min, then held at this temperature for 1 min. The carrier gas was ultra high purity helium with a flow rate of 1.0 mL/min. The inlet (splitless), GC interface, and ion chamber temperatures were 250° C., 250° C., and 230° C., respectively. The sample injection volume used was 2.0 μL. Sorgoleone quantification was performed using a calibration curve of purified sorgoleone, and verified by comparison of sample retention times and mass spectra relative to this standard. GC-EI-MS: $R_t$ 15.9 min, m/z 359 [M+H]$^+$, m/z 168 (benzylic cleavage), m/z 236 [M-CH$_2$CH=CHCH$_2$CH=CHCH$_2$CH=CH, −2H]$^+$, m/z 207 [C$_{15}$ side chain, +2H]$^+$, m/z 189 [C$_{15}$ side chain —CH$_3$, −H]$^+$, m/z 153 [M-C$_{15}$ side chain, +H]$^+$, m/z 139 [153$^+$-CH$_3$, +H]$^+$.

Overall, a complete correlation was observed between hpRNA expression and a dramatic reduction in sorgoleone accumulation. In all cases where hpRNA expression was detected ("+" samples, FIG. 9A), sorgoleone levels were reduced to amounts below the limit of quantitation of the GC-MS analysis employed (approximately 0.003 μg/mg fresh weight). Importantly, this trend was observed in 6 independently transformed events (FIG. 9B), thus establishing that the observed reduction in sorgoleone accumulation was dependent on the expression of the hpRNA-generating transgene, and was not transformation event-specific. As mentioned, two additional (kanamycin-resistant) transformant events were analyzed in which hpRNA expression was not detected in any individuals, and in those cases sorgoleone levels were comparable to those observed for hpRNA "−" individuals in events 1-6 (data not shown). Taken together, the results obtained from ARS1/2-targeting RNAi experiments (FIG. 9A-C), enzymatic assays using recombinant ARS1 and ARS2 (FIG. 4), and the tissue-specific expression pattern determined for ARS1 and ARS2 (FIG. 2B) strongly suggest that ARS1 and ARS2 represent the alkylresorcinol synthase enzymes proposed for the biosynthesis of sorgoleone.

Example 8

Phylogenetic Analysis

Amino acid sequences of putative type III polyketide synthases were retrieved from the NCBI non-redundant peptide sequence database by BLASTP searches using default parameters (Retrieved from the Internet: <URL:blast.ncbi.nlm.nih.gov). A candidate list was screened for redundancy and errors, and a final data set was assembled containing 72 sequences including the three *S. bicolor* and three *O. sativa* sequences biochemically characterized in the present work. Multiple sequence alignments were constructed with GENEIOUS ver. 4.6.2 (Biomatters Ltd., Auckland, NZ) employing the BLOSUM62 log-odds probability matrix (Henikoff and Henikoff. 1993. *Proteins* 17:49-61) and gap open and extension penalties of 12 and 3, respectively. Terminal amino acids with less than 50% coverage were trimmed to yield a final alignment of 409 residues.

Assessment of phylogenetic relationships among sequences employed the Bayesian Markov chain Monte Carlo simulation technique implemented in MRBAYES v. 3.1 (Ronquist and Huelsenbeck. 2003. *Bioinfomatics* 19:15721574). This analytical approach takes advantage of probabilistic models of amino acid substitution and has been shown to be robust to among-site rate heterogeneity and branch-length differences (Mar of al. 2005. *BMC Evol. Biol.* 5:8). Two separate analyses, each containing two independent searches, were run for 10$^8$ generations, sampling every 2000. To incorporate the uncertainty in the appropriate amino acid substitution model, we used mixed priors with gamma-distributed rate variation; posterior support for the Wagner model (Wheland and Goldman. 2001. *Mol. Biol. Evol.* 18:691-699) was 1.0. From this posterior sample of trees from each analysis (n=5000), the first 1000 were discarded as burnin. Adequacy of this burnin was assessed by examining likelihood values of the cold chain for stationarity using TRACER v1.4 (Retrieved from the Internet: <URL: beast.bio.ed.ac.uk/tracer). Support for proposed relationships was assessed by examining the bipartition posterior probability, the frequency of occurrence of a relationship, in the 16,000 pooled post-burnin trees.

Figure 10:
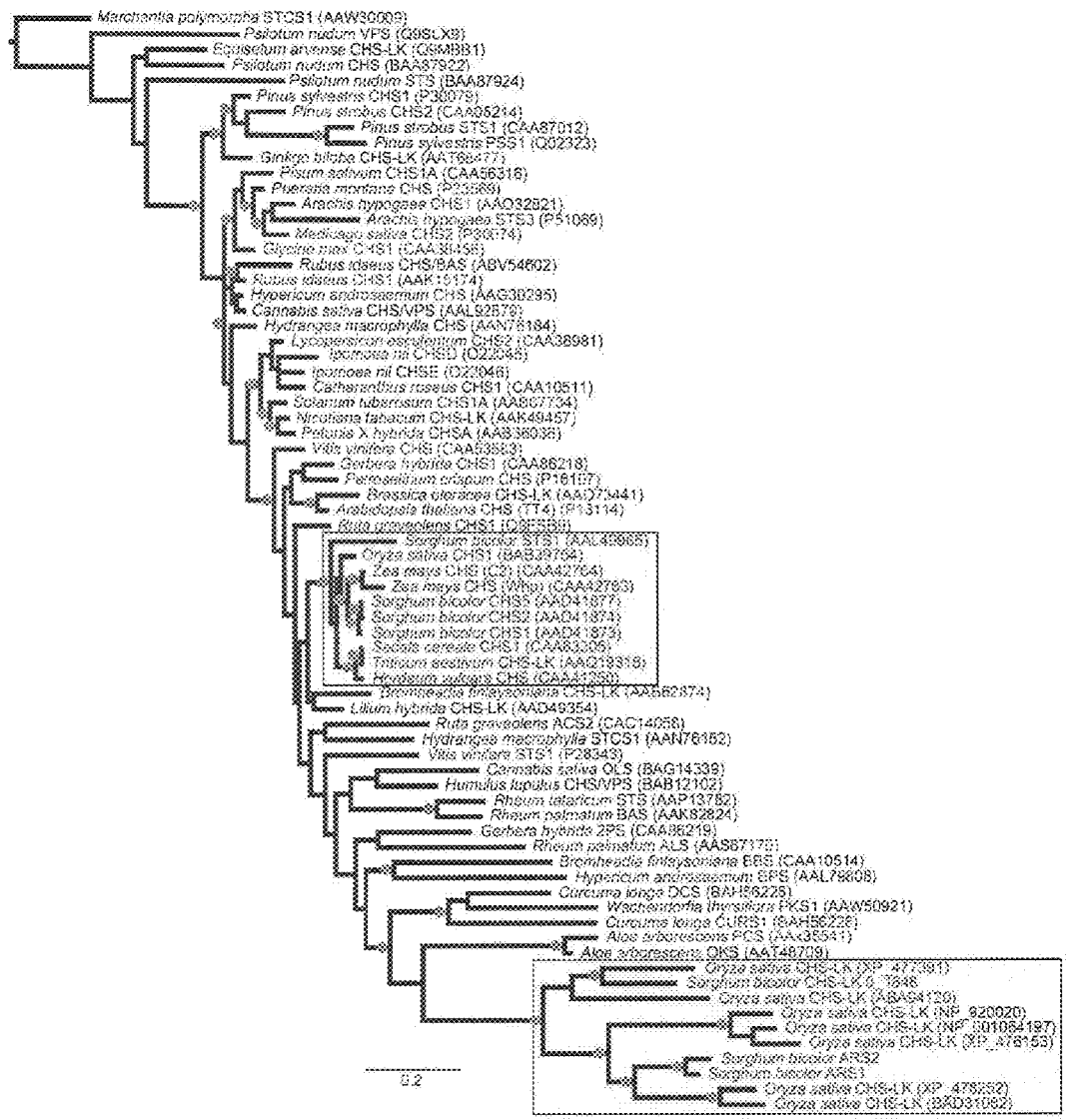
FIG. 10 depicts the phylogenetic analysis of ARS1, ARS2 relatives. Strongly supported nodes (posterior probability greater than 0.95) are indicated by shaded circles. Shaded boxes are included to highlight the placement of *S. bicolor* CHS and non CHS-type sequences, and the bar at bottom represents the distance corresponding to 0.2 substitutions per amino acid. 2PS, 2-pyrone synthase; ACS, acridone synthase; ALS, aloesone synthase; ARS, alkylresorcinol synthase; BAS, benzalacetone synthase; BBS, bibenzyl synthase; BPS, benzophenone synthase; CHS, chalcone synthase; CHS-LK, chalcone synthase-like (unknown function); CURS, curcumin synthase; DCS, diketide CoA synthase; OKS, octaketide synthase; OLS, olivetol synthase; PCS, pentaketide chromone synthase; PSS, pinosylvin synthase; STS, stilbene synthase; STCS, stilbene carboxylate synthase; VPS, valerophenone synthase.

A phylogenetic tree was constructed from 72 representative type III polyketide synthases from various plant families, including functionally characterized enzymes accepting a diversity CoA thioester units (FIG. 10). The stilbene carboxylate synthase 2 (STCS2) enzyme from liverwort, *Marchantia polymorpha*, was chosen to represent the outgroup for this analysis. Overall, these results indicated separate clustering of chalcone synthase and non-chalcone synthase type III PKSs among the diverse angiosperm taxa represented, indicating that the divergence of these enzyme families predates the emergence of angiosperms, as previously suggested by Jiang et al. (2008. *Mol Phylogenet. Evol.* 49:691-701). Additionally, the close relationships between specific CHS- and non-CHS-type enzymes in genera such as *Pinus, Arachis*, and *Sorghum* strongly suggest that the non-CHS-type enzymes are likely polyphyletic in origin, as has also been previously proposed (e.g., Tropf et al. 1994. *J. Mol. Evol.* 38:610-618; Huang et al. 2004. *Acta Bot. Sin.* 46:10-19; Jiang et al., supra).

Figure 11:
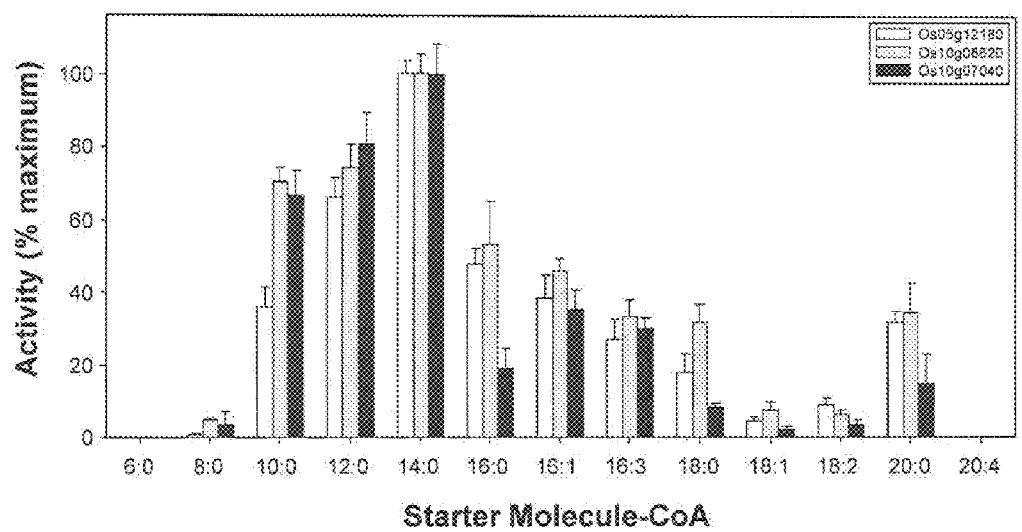
FIG. 11 depicts the enzymatic activities of alkylresorcinol synthases encoded by *O. sativa* LOC_Os05g12180, LOC_Os10g08620, and LOC_Os10g07040. Relative activities were determined for all three recombinant enzymes in assays using acyl-CoA starter units varying in chain length and degree of saturation. For these experiments, the full-length ORFs were heterologously expressed as N-terminal polyhistidine fusions in *E. coli*, then purified by affinity chromatography (see Example 8). Data are expressed as relative mean±SD from assays performed in triplicate.

Interestingly, ARS1 and ARS2 fall within a Glade of monocotyledonous type III PKSs clearly separated from a second monocotyledonous Glade containing predominantly CHS-type enzymes (FIG. 10), which include predicted sequences from rice whose functions are presently obscure. Given that rice is known to synthesize alkylresorcinols thought to function as antimicrobial defense compounds (e.g., Suzuki et at 1998, 2003, supra), it is tempting to speculate that at least a subset of the predicted rice PKS-like sequences closely related to ARS1 and ARS2 could also possess alkyresorcinol synthase activity. To explore this possibility, the predicted open reading frames encoded by *O. sativa* (cv. Nipponbare) LOC_Os05g12180, LOC_Os10g08620, and LOC_Os10g07040, were also expressed in *E. coli* as N-terminal polyhistidine fusions, and tested for alkylresorcinol synthase activity with the same panel of fatty acyl-CoA substrates used for recombinant ARS1 and ARS2 enzymatic studies (FIG. 4). As shown in FIG. 11, all three recombinant rice enzymes accepted various saturated and unsaturated fatty acyl-CoA starter units to produce the corresponding 5-alkylresorcinols, and as was observed for recombinant ARS1 (FIG. 4), exhibited maximal 5-alkylresorcinol-forming activity with myristoyl-CoA (C14). Among the unsaturated acyl-CoA starters tested, maximal activity was observed with palmitoleoyl-CoA (C16:1$\Delta^9$) for all three rice enzymes, as was also seen for both ARS1 and ARS2. No activity was detected for Os05g12180, Os10g08620, and Os10g07040 with the starters hexanoyl-CoA (C6) and arachidonoyl-CoA (C20:4$\Delta^{5,8,11,14}$), potentially indicating that a wider range of fatty acyl-CoA starters can be accepted by the sorghum alkyresorcinol synthase enzymes. The maximal activities obtained for recombinant Os05g12180 and Os10g08620 utilizing the preferred myristoyl-CoA substrate (66.6 pkat mg$^{-1}$ and 48.6 pkat mg$^{-1}$, respectively) were comparable to those observed for ARS1 with myristoyl-CoA and ARS2 with palmitoleoyl-CoA (81.0 pkat mg$^{-1}$ and 60.1 pkat mg$^1$, respectively), however lower activity levels were observed for recombinant Os10g07040 with myristoyl-CoA (13.2 pkat mg$^{-1}$).

As was the case for ARS1 and ARS2, recombinant Os05g12180, Os10g08620, and Os10g07040 each generated a single derailment product from specific saturated fatty acyl-CoA starters, which were also identified as triketide pyrones by analysis of the total ion chromatograms and corresponding mass spectra (see "Methods"). For Os05g12180, triketide pyrone derailment products were produced in assays using C8, C10, and C12 fatty acyl-CoAs, constituting approximately 7%, 11%, and 8% of the total moles product derived from these starters, respectively. For Os10g08620, the triketide pyrone derailment products were produced in assays using C8 and C10 fatty acyl-CoA starters, constituting approximately 8% and 17% of the total moles product formed, respectively. For Os10g07040, the derailment products were produced in assays containing C8, C10, C12, and C14 fatty acyl-CoA starters and constituted approximately 8%, 20%, 6%, and <5% of the total moles product formed, respectively (see "Methods"). Taken together, the results summarized in FIG. 11 strongly suggest a role for Os05g12180, Os10g08620, and Os10g07040 in the biosynthesis of rice alkylresorcinol phytoanticipins, and furthermore, these enzymes likely serve analogous functions given the overall similarity of their substrate utilization profiles.

Example 9

Molecular Modeling

Figure 12:
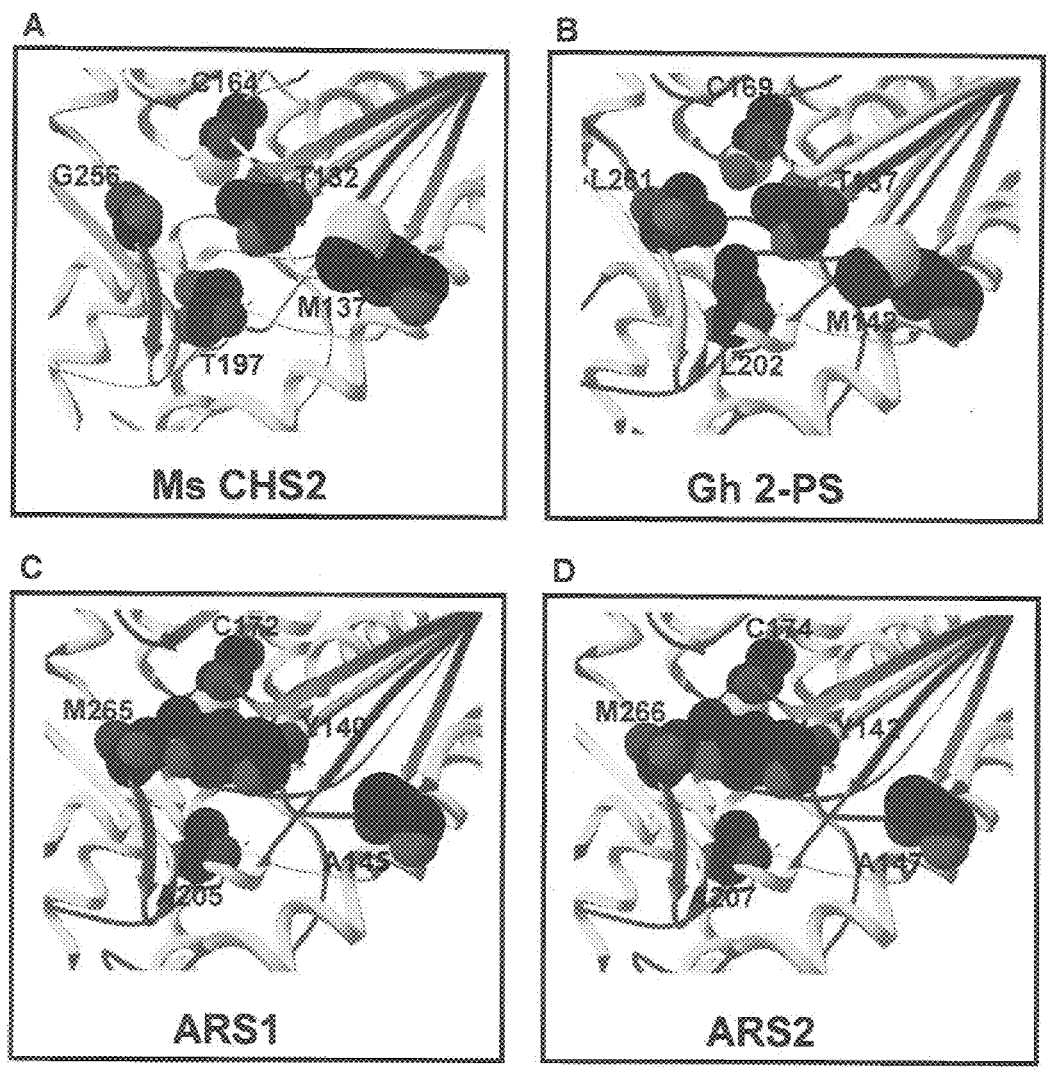
FIGS. 12A-12D depict molecular modeling of ARS1 and ARS2 active sites. The three-dimensional active site structures of *Medicago sativa* CHS2 (Ferrer et al., supra) and *Gerbera hybrida* 2-pyrone synthase (Jez et al., supra) were used to model the active site structures for ARS1 and ARS2. The models were developed with SWISS-MODEL, the automated protein homology-modeling server (Retrieved from the Internet: <URL:expasy.org/spdbv), and visualized with the Swiss-Pdb Viewer (Guex and Peitsch. 1997. *Electrophoresis* 18:2714-2723; Schwede et al. 2003. *Nucleic Acids Res.* 31:3381-3385). Selected residues contributing to the shape/size of the active site architecture are shown in space-filling representation.

To examine the potential structural basis for the observed substrate specificity of ARS1 and ARS2, the crystal structure of *Medicago sativa* CHS2 [Ms CHS2; (Ferrer et al., supra) and *Gerbera hybrida* 2-PS [Gh 2-PS; (Jez at al., supra) were used as templates to create a model of their hypothetical structures, including the proposed active sites (FIG. 12). The overall 3-dimensional structure of ARS1 and ARS2 were very similar to Ms CHS2 and Gh 2-PS (not shown), however, more detailed analyses directed toward the enzyme active sites revealed significant differences that could account for the observed substrate preference of these enzymes (FIG. 12; also indicated in FIGS. 3 and 13), the most significant of which are briefly discussed below.

ARS1 Tyr140, ARS2 Tyr142 versus Ms CHS2 Thr132, Gh 2-PS Thr 137—A threonine in this position is highly conserved among plant type III PKS enzymes, and the presence of tyrosine at this position in ARS1 and ARS2 occurs in no other characterized enzyme within this family. The substitution of a much larger residue suggests a constriction or narrowing of the active site cavity within this region. The significance of this Thr→Tyr exchange is further supported by the observation that the *O. sativa* ARS enzymes identified in the present work (FIG. 11) also contain a tyrosine at this position (FIG. 13).

ARS1 Ala145, ARS2 Ala147 versus Ms CHS2 Met137, Gh 2-PS Met142—The majority of type III PKS enzymes contain a methionine in this position, which provides the sole contribution of the second subunit to the opposing subunit's active site cavity within the PKS homodimer (reviewed in Austin and Noel. 2003. *Nat. Prod. Rep.* 20: 79-110). The corresponding alanine found in ARS1 and ARS2 is fairly unique among type III PKSs, and an identical Met→Ala exchange is also present in the *O. sativa* ARS enzymes investigated in this work (FIG. 13). The substitution of the much smaller alanine residue for methionine would likely result in the significant alteration of the dimensions of the active site cavity, supported by the finding that the simultaneous substitution of Met137→Ala with Gly256→Leu (numbering based on MsCHS2) appears to be an important factor in defining the tunnel necessary for accepting long-chain fatty acyl-CoA substrates in PKS18, a pyrone synthase identified from *Mycobacterium tuberculosis* (Sankaranarayanan et al., 2004. *Nat. Struct. Mol. Biol.* 11:894-900).

ARS1 Ala205, ARS2 Ala207 versus Ms CHS2 Thr197, Gh 2-PS Leu202—Previous studies indicate that this position appears to be of particular significance for determining the accepted substrate size and extent of the active site cavity in type III PKSs. Several important examples where Thr197 is replaced in the corresponding position by other residues in non-chalcone synthase type PKSs include aloesone synthase (ALS) from *Rheum palmatum* [Thr→Ala; (Abe et al. 2004. *FEBBS Lett.* 562: 171-176; Abe et al., 2006. *FEBS J.* 272: 208-218)], as well as several enzymes from *Aloe arborescens* including pentaketide chromone synthase [PCS, Thr→Ala; (Abe et al. 2005b. *J. Amer. Chem. Soc.* 127: 1362-1363; Abe et al. 2007. *J. Amer. Chem. Soc.*, 1299: 5976-5980; Morita et al., 2007. *Chem. Biol.* 14: 359-369)], octaketide synthase [OKS, Thr→Gly; (Abe et al., 2005a. *J. Amer. Chem. Soc.* 127: 12709-12716)], and a second ALS [Thr→Ala; (Mizuuchi et al. 2009. *FEBS J.* 276: 2391-2401)]. A large number of in vitro studies performed with these enzymes have shown that single amino acid substitutions at this position drastically alter the size of the active site cavity and resulting products formed. Specifically, an inverse relationship has been demonstrated between residue side-chain bulk and the active site cavity volume and product size, resulting from the enzyme performing between four to seven condensation reactions (Abe et al., 2004, 2005a, 2005b, 2007, supra; Morita et al., supra; Mizuuchi et al., supra). It therefore seems likely that the corresponding Ala205 in ARS1 and Ala207 in ARS2 similarly contribute to the size of their respective active site cavities, facilitating the utilization of long-chain fatty acyl-CoA starter units.

ARS1 Met265, ARS2 Met266 versus Ms CHS2 Gly256, Gh 2-PS Leu261—The importance of this amino acid position for determining the shape and size of the Ms CHS2 and Gh 2-PS active sites has long been recognized, and site-directed mutagenesis studies where Ms CHS2 Gly256 was replaced with residues containing bulkier side chains resulted in altered substrate utilization and a reduction in the number of condensation reactions performed (reviewed in Austin and Noel, supra). In fact, in studies performed by Jez et al. (supra), it was demonstrated that a T197L/G256L/S338I triple mutant of Ms CHS2 was sufficient to convert the chalcone synthase into a pyrone synthase which would no longer accept bulky phenylpropanoid starter units. An additional example is the *M. tuberculosis* PKS18 enzyme which, like ARS-type enzymes, utilizes long-chain fatty acyl-CoA starter units, and contains both a (Ms CHS2 numbering) Met137→Ala substitution (corresponding to ARS1 Ala145, ARS2 Ala 147—see above), and in addition the substitution of Gly256 (Ms CHS2 numbering) with the much bulkier leucine residue. This combination is believed to be important for determining the dimensions of the tunnel required for interacting with the aliphatic long chain fatty acyl-CoA starter units (Sankaranarayanan et al., supra). The substitution of the bulkier methionine residue for Gly256 in ARS1 and ARS2 would be anticipated to play a role similar to the corresponding leucine substitution in *M. tuberculosis* PKS18, and importantly, the same Gly256→Met substitution (as well as the Met137→Ala substitution, discussed above) is also seen in the three *O. sativa* proteins identified with ARS function (FIG. 13).

Taken together, the models predict that the active sites of both ARS1 and ARS2 are narrower near the upper region adjacent to a catalytically important conserved cysteine residue (ARS1 Cys172, ARS2 Cys174; FIG. 12), and also are of increased overall length relative to that of CHS2 and 2-pyrone synthase (Jez et al., supra), producing a cavity appearing more adequately suited to accommodating long- to medium-chain fatty acyl-CoA starter units (FIG. 12C-D). Interestingly, the sharp drop in activity observed for both ARS1 and ARS2 with fatty acyl-CoAs longer than C16 (FIG. 4) could indicate that this cavity length becomes limiting for the type of substrates that can be accepted. Additionally, the lack of activity with acyl-CoAs less than C6 (FIG. 4) could indicate that substrate filling of this elongated active cavity is critical to enzyme activity. Consistent with this notion, structural studies recently performed with PKSIIINc, a type III PKS from *Neurospora crassa* utilizing long chain fatty acyl-CoAs for the production of various resorcinolic metabolites (Funa et al. 2007, supra), have demonstrated that a similar hydrophobic active site tunnel is involved in determining the starter fatty acyl-CoA chain length specificity for this enzyme (Goyal et al., supra).

Example 10

Substrates 5-n-Pentadecyl resorcinol was purchased from Chem Service, Inc. (West Chester, Pa.). Benzoyl-CoA, malonyl-CoA, butryl-CoA, isobutryl-CoA, isovaleryl-CoA, hexanoyl-CoA, capryloyl-CoA, caproyl-CoA, lauroyl-CoA, myristoyl-CoA, palmitoyl-CoA, palmitoleoyl-CoA, stearoyl-CoA, oleoyl-CoA, linoleoyl-CoA, arachidoyl-CoA, arachidonoyl-CoA, and olivetol were purchased from Sigma-Aldrich (St. Louis, Mo.). For the preparation of hexadecatrienyl ((9Z,12Z)-hexadeca-9,12,15-trienyl)-CoA, the identities of all compounds were confirmed using both physical and spectroscopic methods, including $^1$H-NMR, $^{13}$C-NMR, and high-resolution time-of-flight mass spectroscopy (HRTOFMS), as described below. 5-Hexen-2-yn-1-ol was prepared from allyl bromide and propagyl alcohol using the method described by Taber and You (1995. *J. Org. Chem.* 60:139-142), 5-Hexen-2-yn-1-ol was converted to 1-bromohexen-5-en-2-yne by the method described by Tyman and Visani (1997. Chem. Phys. Lipids 85: 157-174), and 9-decynoic acid was prepared from 8-bromooctanoic acid and lithium acetylide using the method described by Singh and Schnur (1986. Synth. Commun. 16:847-852). 9-Decynoic acid was then converted to its methyl ester using the method described by Itoh et al. (2002. *Biosci. Biotechnol. Biochem.* 66:1591-1596). For preparation of methyl hexadeca-15-en-9,12-diynoate, methyl dec-9-ynoate (1.0 g, 5.5 mmol) was added to a stirred mixture containing $CsCO_3$ (1.79 g, 5.5 mmol), NaI (825 mg, 5.5 mmol), and CuI (825 mg, 5.5 mmol) in dry DMF (10 ml) at room temperature under nitrogen, then allowed to stir for an additional 20 min. To this mixture 6-bromohexen-1-en-4-yne (880 mg, 5.5 mmol) in DMF (2 mL) was added drop-wise, and allowed to stir overnight at room temperature. The reaction mixture was then quenched with saturated $NH_4Cl$, extracted with ethyl acetate, and the organic layer was dried over $MgSO_4$ and evaporated to completion. The residue was then chromatographed over silica gel and eluted with hexanes:ethyl acetate to yield methyl hexadeca-15-en-9,12-diynoate (1.3 g). The characterization data for methyl hexadeca-15-en-9,12-diynoate is provided below.

HRTOFMS: m/e (M+1) 261.18534 (calculated for $C_{17}H_{25}O_2$, 261.18545)

$^1$H NMR: (δ, $CDCl_3$) 5.79 (1H, m, 15-H), 5.29 (1H, dd, J=16.8, 1.6 Hz, 16-H), 5.13 (1H, dd, J=10.0, 1.6 Hz, 16-H), 3.65 (3H, s, $OCH_3$), 3.14 (2H, m, 14-H), 2.93 (2H, m, 11-H), 2.28 (2H, t, J=7.2 Hz, 2CH2), 2.13 (2H, m, 8-H), 1.60 (2H, m), 1.46 (2H, m), 1.34 (2H, m), 1.23 (4H, m)

$^{13}$C-NMR: (δ, $CDCl_3$) 174.2 (C=O), 132.7 (C-15), 115.9 (C-14), 80.5, 77.1, 76.8, 74.3 (C-13, 12, 10, 9), 51.4 (OMe), 34.0 29.0, 28.7, 28.6, 24.8, 23.0, 22.7, 18.6, 9.7. (9Z,12Z)

For the preparation of methyl hexadeca-9,12,15-trienoate, a solution of methyl hexadeca-15-en-9,12-diynoate (800 mg) in ethyl acetate (15 mL) was hydrogenated in the presence of Lindlar catalyst (300 mg) at ambient pressure using a balloon for 20 h. The catalyst was then removed by filtration, and the solvent was evaporated to yield (9Z,12Z)-methyl hexadeca-9,12,15-trienoate as the major product. A portion of the product was then purified by preparative thin layer chromatography using hexanes:ethyl acetate 98:2 (3 developments) to yield pure (9Z,12Z)-methyl hexadeca-9,12,15-trienoate. The characterization data for (9Z,12Z)-methyl hexadeca-9,12,15-trienoate is provided below.

HRTOFMS: m/e (M+1) 265.21701 (calcd for $C_{17}H_{29}O_2$, 265.21675)

¹H NMR: (δ, CDCl₃) 5.79 (1H, m, 15-H), 5.45-5.33 (4H, m, 13, 12, 10, 9-H), 5.03 (1H, dd, J=17.2, 1.6 Hz, 16-H), 4.97 (1H, dd, J=10.0, 1.6 Hz, 16-H), 3.65 (3H, s, OCH₃), 2.80 (4H, m, 11,14-H), 2.29 (2H, t, J=7.6 Hz, 2-H), 2.07 (2H, m, 8-H), 1.61 (2H, m, 3-H), 1.30 (10H, brs, 7,6,5,4,3-H)

¹³C-NMR: (δ, CDCl₃) 174.2 (C=O), 136.7 (C-15), 130.2 (C-9), 129.2 (C-12), 127.6 (C-10), 126.8 (C-13), 114.6 (C-16), 51.3 (OMe), 34.0, 31.5, 29.5, 29.1, 29.1, 29.0, 27.1, 25.5, 24.9

For the preparation of (9Z,12Z)-hexadeca-9,12,15-trienoic acid, 10 mL of 0.5 M LiOH was added dropwise while stirring to a solution of (9Z,12Z)-methyl hexadeca-9,12,15-trienoate (75 mg) in THF (25 mL) at 0° C. The reaction mixture was then stirred for an additional 30 min, allowed to cool to room temperature, then left stirring for an additional 12 h. The majority of the THF was removed under vacuum, then the remaining solution was adjusted to pH 2.0 with HCl (1 M), and extracted with ether. The organic phase was then dried to completion, yielding pure (9Z,12Z)-hexadeca-9,12,15-trienoic acid. The characterization data for (9Z,12Z)-hexadeca-9,12,15-trienoic acid is provided below.

¹H NMR: (δ, CDCl₃) 5.83 (1H, m, 15-H), 5.49-5.33 (4H, m, 13, 12, 10, 9-H), 5.07 (1H, dd, J=17.2, 1.6 Hz, 16-H), 5.00 (1H, dd, J=10.0, 1.6 Hz, 16-H), 2.82 (4H, m, 11,14-H), 2.36 (2H, t, J=7.2 Hz, 2-H), 2.07 (2H, m, 8-H), 1.65 (2H, m, 3-H), 1.34 (10H, brs, 7,6,5,4,3-H)

¹³C-NMR: (δ, CDCl₃) 180.4 (C=O), 136.8 (C-15), 130.3 (C-9), 129.3 (C-12), 127.7 (C-10), 126.8 (C-13), 114.7 (C-16), 34.1, 31.5, 29.5, 29.1, 29.0, 29.0, 27.2, 25.6, 24.6.

For the preparation of (9Z,12Z)-Hexadeca-9,12,15-trienyl chloride, (9Z,12Z)-Hexadeca-9,12,15-trienoic acid in toluene (3.5 mL) was first treated with oxalyl chloride (0.5 mL) at 35-40° C. for 1 h, then the solvent and excess oxalyl chloride was evaporated under vacuum. The residue was then re-dissolved in toluene and the solvent was evaporated under vacuum. This process was repeated twice more, then the product, (9Z,12Z)-hexadeca-9,12,15-trienyl chloride, was directly used in the subsequent reaction. (9Z,12Z)-Hexadeca-9,12,15-trienyl-CoA was then prepared from (9Z,12Z)-hexadeca-9,12,15-trienyl chloride and coenzyme A using a modification of the procedure described by Bishop and Hajra (1980. *Anal. Biochem.* 106:3434-350). Briefly, to a stirred solution of 300 mg (0.38 mmol) coenzyme A in 5 mL of a 1:2.2 mixture of aqueous NaHCO₃ (150 mM, pH adjusted to 8.8 with NaOH) and tetrahydrofuran at 35° C. under nitrogen, (9Z,12Z)-hexadeca-9,12,15-trienoyl chloride (48 mg, 0.19 mmol) was added. After 30 min, the reaction was quenched by the addition of 80 □L of 10% HClO₄, and then concentrated under a stream of nitrogen. The precipitate was then recovered by centrifugation at 20,000×g for 15 min at 4° C., decanted, then mixed with 8 mL of 1.3% perchloric acid. The mixture was then chilled using an ice bath, and re-centrifuged at 20,000×g for 15 min at 4° C. The pellet was then washed with ice-cold perchloric acid (1.3%, 8 mL), then washed with 12 mL acetone, followed by two additional washes with 12 mL ether, and finally air-dried to completion and resuspended in phosphate buffer (pH 7.0) at a final concentration of 1.0 mM. The molecular weight of (9Z,12Z)-Hexadeca-9,12,15-trienyl-CoA was determined to be m/e (M+1) 1000.7276 by HRTOFMS.

For the above synthesis, allyl bromide, propagyl alcohol, 8-bromooctanoic acid and lithium acetylide ethylenediamine complex were purchased from Sigma-Aldrich (St. Louis, Mo.). ¹H-NMR and ¹³C-NMR spectra were recorded using an Avance DPX-400 spectrometer (400 MHz for ¹H NMR, 100 MHz for ¹³C NMR; Bruker Biospin Corp., Billerica, Mass.) in CDCl₃, using tetramethylsilane as an internal standard. HRTOFMS were measured on an Agilent Series 1100 SL mass spectrometer equipped with an ESI source (Agilent Technologies, Santa Clara, Calif.).

5-n-[8',11',14']-Pentadecatrienyl resorcinol was purified from *Anacardium occidentale* (cashew) nutshell liquid using the method developed by Paramashivappa et al. (2001. *J. Agric. Food Chem.* 49:2548-2551).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method of manipulating alkylresorcinol synthase content in a plant or plant cell thereby increasing the level of alkylresorcinol accumulation in the plant or plant cell as compared to the level of alkylresorcinol accumulation in a wild type plant of the same variety comprising:

introducing into a plant or a plant cell at least one construct comprising a cDNA sequence operably linked to a promoter that drives expression in a plant cell wherein the cDNA is an isolated or recombinant cDNA consisting of a nucleotide sequence that encodes SEQ ID NO:2; that encodes an amino acid sequence having 99% identity to SEQ ID NO:2; that is SEQ ID NO:1; or that is a sequence having at least 99% identity to SEQ ID NO:1; wherein the cDNA sequence increases the accumulation of alkylresorcinol in the plant or plant cell when expressed therein; and selecting the resulting transgenic plant for having increased levels of alkylresorcinol accumulation as compared to a wild type plant of the same variety.

2. A method for increasing accumulation of phenolic lipids in a plant cell comprising transfecting the cell with the cDNA sequence operatively linked to a nucleic acid which is a regulatory sequence enabling expression of the nucleic acid in the cell, wherein the cDNA is an isolated or recombinant cDNA consisting of a nucleotide sequence that encodes SEQ ID NO:2; that encodes an amino acid sequence having 99% identity to SEQ ID NO:2; that is SEQ ID NO:1: or that is a sequence having at least 99% identity to SEQ ID NO:1, wherein the cDNA sequence increases the accumulation of alkylresorcinol in the plant or plant cell when expressed therein; and selecting the resulting transfected plant cells for their increased levels of alkylresorcinol accumulation as compared to a wild type plant cells.

3. The method of claim 2 wherein the regulatory sequence is an enhancer or a tissue specific promoter.

4. A transgenic plant made by the method of claim 1, or a progeny thereof comprising said cDNA, wherein said plant or progeny thereof is selected for increased levels of alkylresorcinol accumulation as compared to the alkylresorcinol accumulation in a wild type plant of the same variety.

5. A transgenic plant cell made by the method of claim 2, or a progeny thereof comprising said cDNA, wherein said plant cell or progeny thereof is selected for increased levels of alkylresorcinol accumulation as compared to the alkylresorcinol accumulation in a wild type plant cell of the same variety.

* * * * *

SEQUENCE LISTING

<160> NUMBER OF SEQ ID NOS: 61

<210> SEQ ID NO 1
<211> LENGTH: 1215
<212> TYPE: DNA
<213> ORGANISM: Sorghum bicolor

<400> SEQUENCE: 1

```
atggggagcg caccgccggc ggccaccgtc caggagatga ggcgtgcgca gcgcgcggat      60
gggccggccg ccgtgctcgc catcggcacg gcgaaccctc cgagcatcat gccccaggac     120 gattacccc g actactactt ccgcgtcacc aacagcgagc acctcacgga cctcaaggcc     180
aagctcagcc ggatctgcaa ccacaacaag tccggcatca ggcagcgcta cctgcacctc     240
aacgaggagc tgctggccgc caacccgggc ttcatcgacc ccaagcggcc gtccctggac     300
gagcgcgtgg agatggcctc cgccgccgtc ccggagctgg ccgcgaaagc cgccgccaag     360
gccatcgcgg agtggggccg cccggccacc gacatcaccc acctcatctt cagcacctac    420
```

```
tccggcgcgc gtgccccgag cggcgaccgc cgcctggcct ccctcctggg cctccgcccc    480
acggtgtccc gcaccatcct cagcctccac ggctgctacg gcgggggggag ggcgctccag   540
ctcgccaagg agctcgccga gaacaaccgc ggcgcgcgcg tcctcgtcgc ctgctctgag    600
ctcacgctca tcgccttcta cgggcccgag ggaggctgcg tcgacaacat catcggccag    660
accttgttcg gtgacggcgc cggcgccgtc atcgtcggcg ccgaccccgt cggcgcccct    720
gccgagcgcc cgctgttcga gatggtgttc gcgtcgcaga ccacgatacc ggagaccgag    780
gacgccatct ccatgcagta cagcaaatgc ggcatggagt accacctctc cagccgggtg    840
ccccgcgtgc tggggtccaa cgtcgaacgc tgccttgttg acacgttccg cacgctcggc    900
gtcagcgtcg catggaacga ccttttctgg gcgatccatc ccggcggccg tgccatcctg    960
gacaacatcg aggaagtgct ccgtctggag gacgggaaac tggcggcgag tcgccatgtg   1020
ctcagcgagt ttggcaacat gagtggcacc acggtgatct tcgtgctcga tgagttgcgc   1080
cgccgtcggg cagcagcggc caagcaggga gggcaagcgc cggagtgggg agtgatgatg   1140
gcttttggac cgggaatcac agttgagacc atggtgctcc acgccccaag caacctggaa   1200
ctggagggaa attga                                                    1215

<210> SEQ ID NO 2
<211> LENGTH: 404
<212> TYPE: PRT
<213> ORGANISM: Sorghum bicolor

<400> SEQUENCE: 2

Met Gly Ser Ala Pro Ala Ala Thr Val Gln Glu Met Arg Arg Ala
1               5                   10                  15

Gln Arg Ala Asp Gly Pro Ala Ala Val Leu Ala Ile Gly Thr Ala Asn
            20                  25                  30

Pro Pro Ser Ile Met Pro Gln Asp Asp Tyr Pro Asp Tyr Tyr Phe Arg
        35                  40                  45

Val Thr Asn Ser Glu His Leu Thr Asp Leu Lys Ala Lys Leu Ser Arg
    50                  55                  60

Ile Cys Asn His Asn Lys Ser Gly Ile Arg Gln Arg Tyr Leu His Leu
65                  70                  75                  80

Asn Glu Glu Leu Leu Ala Ala Asn Pro Gly Phe Ile Asp Pro Lys Arg
                85                  90                  95

Pro Ser Leu Asp Glu Arg Val Glu Met Ala Ser Ala Val Pro Glu
            100                 105                 110

Leu Ala Ala Lys Ala Ala Lys Ala Ile Ala Glu Trp Gly Arg Pro
        115                 120                 125

Ala Thr Asp Ile Thr His Leu Ile Phe Ser Thr Tyr Ser Gly Ala Arg
    130                 135                 140

Ala Pro Ser Gly Asp Arg Arg Leu Ala Ser Leu Leu Gly Leu Arg Pro
145                 150                 155                 160

Thr Val Ser Arg Thr Ile Leu Ser Leu His Gly Cys Tyr Gly Gly Gly
                165                 170                 175

Arg Ala Leu Gln Leu Ala Lys Glu Leu Ala Glu Asn Asn Arg Gly Ala
            180                 185                 190

Arg Val Leu Val Ala Cys Ser Glu Leu Thr Leu Ile Ala Phe Tyr Gly
        195                 200                 205

Pro Glu Gly Gly Cys Val Asp Asn Ile Ile Gly Gln Thr Leu Phe Gly
    210                 215                 220
```

```
Asp Gly Ala Gly Ala Val Ile Val Gly Ala Asp Pro Val Gly Ala Pro
225                 230                 235                 240

Ala Glu Arg Pro Leu Phe Glu Met Val Phe Ala Ser Gln Thr Thr Ile
            245                 250                 255

Pro Glu Thr Glu Asp Ala Ile Ser Met Gln Tyr Ser Lys Cys Gly Met
        260                 265                 270

Glu Tyr His Leu Ser Ser Arg Val Pro Arg Val Leu Gly Ser Asn Val
    275                 280                 285

Glu Arg Cys Leu Val Asp Thr Phe Arg Thr Leu Gly Val Ser Val Ala
290                 295                 300

Trp Asn Asp Leu Phe Trp Ala Ile His Pro Gly Gly Arg Ala Ile Leu
305                 310                 315                 320

Asp Asn Ile Glu Glu Val Leu Arg Leu Glu Asp Gly Lys Leu Ala Ala
            325                 330                 335

Ser Arg His Val Leu Ser Glu Phe Gly Asn Met Ser Gly Thr Thr Val
        340                 345                 350

Ile Phe Val Leu Asp Glu Leu Arg Arg Arg Ala Ala Ala Ala Ala Lys
    355                 360                 365

Gln Gly Gly Gln Ala Pro Glu Trp Gly Val Met Met Ala Phe Gly Pro
370                 375                 380

Gly Ile Thr Val Glu Thr Met Val Leu His Ala Pro Ser Asn Leu Glu
385                 390                 395                 400

Leu Glu Gly Asn

<210> SEQ ID NO 3
<211> LENGTH: 1218
<212> TYPE: DNA
<213> ORGANISM: Sorghum bicolor

<400> SEQUENCE: 3
atggggtcca tggggaaggc actaccggcc accgtcgacg agatcaggcg tgcgcagcgc    60
gcggaagggc cggccgccgt gctcgccatc ggcacggcga acccgcccac aatcatgccc   120
caggacgact accccgacta ctacttccgc gtcaccaaca gcgagcacct caccgacctc   180
aaggccaagc tcagcaggat ctgcaaccac aacaagtccg gcatcaggca gcgctacctg   240
cacctcaacg aggagcttct cgccgccaac ccgggcttca tcgaccccaa gcggccgtcc   300
ctggacgagc gcgtggagat ggcctccgcc gccgtcccgg agctggccgc gaaagccgcc   360
accaaggcca tcgcggagtg gggccgtccc gccaccgaca tcacccacct catcttcagc   420
acctactccg gcgcgcgtgc cccgagcgga accgccgcc tcgcctccct gctgggcctc   480
cgccccaccg tgtcccgcac catcctcaac ctccacggct gctacggcgg ggggcggtcg   540
ctccagctcg ccaaggagat cgccgagaac aaccgcggcg cgcgcgtcct cgtcgcctgc   600
tccgagctca cgctcatcgc cttctacggg cccgagggag gctgcgtcga acatcatc    660 ggccagacct tgttcggcga cggtgccggc ccgtcgtcg tcggcgccga ccctgacgcc   720
gccgtcgagc gcccgctgtt cgagatggcg ttcgcgacgc agaccacgat accggagagc   780
gaggacgcca tctccatgca gtacagcaaa tgtggcatgg agtaccacct ctccagcaag   840
gtgccacgcc tgatagggtg caacgtggaa cgctcccttg tcgacacgtt ccgcacgctc   900
ggcgtcaccg ccgcatggaa tgacctgttc tgggcggttc accccggagg tcgtgccatc   960
ctggacaaca tcgaggaagt gctcggtctg gaggacgaca aactggcggc gagtcgccat  1020
gtgctcagtg agtttggcaa catgagtggc accacggtga tcttcgtgct cgatgagttg  1080
```

-continued

```
cgccgacgtc gggcagcggc ggcgaagcag gaggggaaa cgccggagtg gggagtgctc    1140
atggcttttg gacccgggaat cacaatcgag accatagtgc tccacacccc aagcaacccg   1200
gaactggagg gaaattga                                                   1218
```

<210> SEQ ID NO 4
<211> LENGTH: 405
<212> TYPE: PRT
<213> ORGANISM: Sorghum bicolor

<400> SEQUENCE: 4

```
Met Gly Ser Met Gly Lys Ala Leu Pro Ala Thr Val Asp Glu Ile Arg
1               5                   10                  15

Arg Ala Gln Arg Ala Glu Gly Pro Ala Ala Val Leu Ala Ile Gly Thr
            20                  25                  30

Ala Asn Pro Pro Thr Ile Met Pro Gln Asp Asp Tyr Pro Asp Tyr Tyr
        35                  40                  45

Phe Arg Val Thr Asn Ser Glu His Leu Thr Asp Leu Lys Ala Lys Leu
    50                  55                  60

Ser Arg Ile Cys Asn His Asn Lys Ser Gly Ile Arg Gln Arg Tyr Leu
65                  70                  75                  80

His Leu Asn Glu Glu Leu Leu Ala Ala Asn Pro Gly Phe Ile Asp Pro
                85                  90                  95

Lys Arg Pro Ser Leu Asp Glu Arg Val Glu Met Ala Ser Ala Ala Val
            100                 105                 110

Pro Glu Leu Ala Ala Lys Ala Ala Thr Lys Ala Ile Ala Glu Trp Gly
        115                 120                 125

Arg Pro Ala Thr Asp Ile Thr His Leu Ile Phe Ser Thr Tyr Ser Gly
    130                 135                 140

Ala Arg Ala Pro Ser Gly Asp Arg Arg Leu Ala Ser Leu Leu Gly Leu
145                 150                 155                 160

Arg Pro Thr Val Ser Arg Thr Ile Leu Asn Leu His Gly Cys Tyr Gly
                165                 170                 175

Gly Gly Arg Ser Leu Gln Leu Ala Lys Glu Ile Ala Glu Asn Asn Arg
            180                 185                 190

Gly Ala Arg Val Leu Val Ala Cys Ser Glu Leu Thr Leu Ile Ala Phe
        195                 200                 205

Tyr Gly Pro Glu Gly Gly Cys Val Asp Asn Ile Ile Gly Gln Thr Leu
    210                 215                 220

Phe Gly Asp Gly Ala Gly Ala Val Val Gly Ala Asp Pro Asp Ala
225                 230                 235                 240

Ala Val Glu Arg Pro Leu Phe Glu Met Ala Phe Ala Thr Gln Thr Thr
                245                 250                 255

Ile Pro Glu Ser Glu Asp Ala Ile Ser Met Gln Tyr Ser Lys Cys Gly
            260                 265                 270

Met Glu Tyr His Leu Ser Ser Lys Val Pro Arg Leu Ile Gly Cys Asn
        275                 280                 285

Val Glu Arg Ser Leu Val Asp Thr Phe Arg Thr Leu Gly Val Thr Ala
    290                 295                 300

Ala Trp Asn Asp Leu Phe Trp Ala Val His Pro Gly Gly Arg Ala Ile
305                 310                 315                 320

Leu Asp Asn Ile Glu Glu Val Leu Gly Leu Glu Asp Asp Lys Leu Ala
                325                 330                 335

Ala Ser Arg His Val Leu Ser Glu Phe Gly Asn Met Ser Gly Thr Thr
            340                 345                 350
```

```
Val Ile Phe Val Leu Asp Glu Leu Arg Arg Arg Ala Ala Ala
            355                 360                 365
Lys Gln Gly Gly Glu Thr Pro Glu Trp Gly Val Leu Met Ala Phe Gly
    370                 375                 380
Pro Gly Ile Thr Ile Glu Thr Ile Val Leu His Thr Pro Ser Asn Pro
385                 390                 395                 400
Glu Leu Glu Gly Asn
                405

<210> SEQ ID NO 5
<211> LENGTH: 389
<212> TYPE: PRT
<213> ORGANISM: Medicago sativa

<400> SEQUENCE: 5

Met Val Ser Val Ser Glu Ile Arg Lys Ala Gln Arg Ala Glu Gly Pro
1               5                   10                  15
Ala Thr Ile Leu Ala Ile Gly Thr Ala Asn Pro Ala Asn Cys Val Glu
            20                  25                  30
Gln Ser Thr Tyr Pro Asp Phe Tyr Phe Lys Ile Thr Asn Ser Glu His
        35                  40                  45
Lys Thr Glu Leu Lys Glu Lys Phe Gln Arg Met Cys Asp Lys Ser Met
    50                  55                  60
Ile Lys Arg Arg Tyr Met Tyr Leu Thr Glu Glu Ile Leu Lys Glu Asn
65                  70                  75                  80
Pro Asn Val Cys Glu Tyr Met Ala Pro Ser Leu Asp Ala Arg Gln Asp
                85                  90                  95
Met Val Val Val Glu Val Pro Arg Leu Gly Lys Glu Ala Ala Val Lys
            100                 105                 110
Ala Ile Lys Glu Trp Gly Gln Pro Lys Ser Lys Ile Thr His Leu Ile
        115                 120                 125
Val Cys Thr Thr Ser Gly Val Asp Met Pro Gly Ala Asp Tyr Gln Leu
    130                 135                 140
Thr Lys Leu Leu Gly Leu Arg Pro Tyr Val Lys Arg Tyr Met Met Tyr
145                 150                 155                 160
Gln Gln Gly Cys Phe Ala Gly Gly Thr Val Leu Arg Leu Ala Lys Asp
                165                 170                 175
Leu Ala Glu Asn Asn Lys Gly Ala Arg Val Leu Val Val Cys Ser Glu
            180                 185                 190
Val Thr Ala Val Thr Phe Arg Gly Pro Ser Asp Thr His Leu Asp Ser
        195                 200                 205
Leu Val Gly Gln Ala Leu Phe Gly Asp Gly Ala Ala Ala Leu Ile Val
    210                 215                 220
Gly Ser Asp Pro Val Pro Glu Ile Glu Lys Pro Ile Phe Glu Met Val
225                 230                 235                 240
Trp Thr Ala Gln Thr Ile Ala Pro Asp Ser Glu Gly Ala Ile Asp Gly
                245                 250                 255
His Leu Arg Glu Ala Gly Leu Thr Phe His Leu Leu Lys Asp Val Pro
            260                 265                 270
Gly Ile Val Ser Lys Asn Ile Thr Lys Ala Leu Val Glu Ala Phe Glu
        275                 280                 285
Pro Leu Gly Ile Ser Asp Tyr Asn Ser Ile Phe Trp Ile Ala His Pro
    290                 295                 300
Gly Gly Pro Ala Ile Leu Asp Gln Val Glu Gln Lys Leu Ala Leu Lys
305                 310                 315                 320
```

```
Pro Glu Lys Met Asn Ala Thr Arg Glu Val Leu Ser Glu Tyr Gly Asn
            325                 330                 335

Met Ser Ser Ala Cys Val Leu Phe Ile Leu Asp Glu Met Arg Lys Lys
        340                 345                 350

Ser Thr Gln Asn Gly Leu Lys Thr Thr Gly Glu Gly Leu Glu Trp Gly
            355                 360                 365

Val Leu Phe Gly Phe Gly Pro Gly Leu Thr Ile Glu Thr Val Val Leu
        370                 375                 380

Arg Ser Val Ala Ile
385

<210> SEQ ID NO 6
<211> LENGTH: 402
<212> TYPE: PRT
<213> ORGANISM: Gerbera hybrida

<400> SEQUENCE: 6

Met Gly Ser Tyr Ser Ser Asp Asp Val Glu Val Ile Arg Glu Ala Gly
1               5                   10                  15

Arg Ala Gln Gly Leu Ala Thr Ile Leu Ala Ile Gly Thr Ala Thr Pro
            20                  25                  30

Pro Asn Cys Val Ala Gln Ala Asp Tyr Ala Asp Tyr Tyr Phe Arg Val
        35                  40                  45

Thr Lys Ser Glu His Met Val Asp Leu Lys Glu Lys Phe Lys Arg Ile
    50                  55                  60

Cys Glu Lys Thr Ala Ile Lys Lys Arg Tyr Leu Ala Leu Thr Glu Asp
65                  70                  75                  80

Tyr Leu Gln Glu Asn Pro Thr Met Cys Glu Phe Met Ala Pro Ser Leu
            85                  90                  95

Asn Ala Arg Gln Asp Leu Val Val Thr Gly Val Pro Met Leu Gly Lys
        100                 105                 110

Glu Ala Ala Val Lys Ala Ile Asp Glu Trp Gly Leu Pro Lys Ser Lys
        115                 120                 125

Ile Thr His Leu Ile Phe Cys Thr Thr Ala Gly Val Asp Met Pro Gly
    130                 135                 140

Ala Asp Tyr Gln Leu Val Lys Leu Leu Gly Leu Ser Pro Ser Val Lys
145                 150                 155                 160

Arg Tyr Met Leu Tyr Gln Gln Gly Cys Ala Ala Gly Gly Thr Val Leu
                165                 170                 175

Arg Leu Ala Lys Asp Leu Ala Glu Asn Asn Lys Gly Ser Arg Val Leu
            180                 185                 190

Ile Val Cys Ser Glu Ile Thr Ala Ile Leu Phe His Gly Pro Asn Glu
        195                 200                 205

Asn His Leu Asp Ser Leu Val Ala Gln Ala Leu Phe Gly Asp Gly Ala
    210                 215                 220

Ala Ala Leu Ile Val Gly Ser Gly Pro His Leu Ala Val Glu Arg Pro
225                 230                 235                 240

Ile Phe Glu Ile Val Ser Thr Asp Gln Thr Ile Leu Pro Asp Thr Glu
                245                 250                 255

Lys Ala Met Lys Leu His Leu Arg Glu Gly Gly Leu Thr Phe Gln Leu
            260                 265                 270

His Arg Asp Val Pro Leu Met Val Ala Lys Asn Ile Glu Asn Ala Ala
        275                 280                 285

Glu Lys Ala Leu Ser Pro Leu Gly Ile Thr Asp Trp Asn Ser Val Phe
    290                 295                 300
```

```
Trp Met Val His Pro Gly Gly Arg Ala Ile Leu Asp Gln Val Glu Arg
305                 310                 315                 320

Lys Leu Asn Leu Lys Glu Asp Lys Leu Arg Ala Ser Arg His Val Leu
            325                 330                 335

Ser Glu Tyr Gly Asn Leu Ile Ser Ala Cys Val Leu Phe Ile Ile Asp
        340                 345                 350

Glu Val Arg Lys Arg Ser Met Ala Glu Gly Lys Ser Thr Thr Gly Glu
    355                 360                 365

Gly Leu Asp Cys Gly Val Leu Phe Gly Phe Gly Pro Gly Met Thr Val
370                 375                 380

Glu Thr Val Val Leu Arg Ser Val Arg Val Thr Ala Ala Val Ala Asn
385                 390                 395                 400

Gly Asn

<210> SEQ ID NO 7
<211> LENGTH: 401
<212> TYPE: PRT
<213> ORGANISM: Sorghum bicolor

<400> SEQUENCE: 7

Met Ala Gly Ala Thr Val Thr Val Glu Glu Val Arg Lys Ala Gln Arg
1               5                   10                  15

Ala Thr Gly Pro Ala Thr Val Leu Ala Ile Gly Thr Ala Thr Pro Ala
            20                  25                  30

Asn Cys Val His Gln Ala Asp Tyr Pro Asp Tyr Tyr Phe Arg Ile Thr
        35                  40                  45

Lys Ser Glu His Met Thr Glu Leu Lys Glu Lys Phe Lys Arg Met Cys
50                  55                  60

Asp Lys Ser Gln Ile Arg Lys Arg Tyr Met His Leu Thr Glu Glu Tyr
65                  70                  75                  80

Leu Ala Glu Asn Pro Asn Met Cys Ala Tyr Met Ala Pro Ser Leu Asp
                85                  90                  95

Ala Arg Gln Asp Ile Val Val Glu Val Pro Lys Leu Gly Lys Ala
            100                 105                 110

Ala Ala Gln Lys Ala Ile Lys Glu Trp Gly Gln Pro Lys Ser Lys Ile
        115                 120                 125

Thr His Leu Val Phe Cys Thr Thr Ser Gly Val Asp Met Pro Gly Ala
130                 135                 140

Asp Tyr Gln Leu Thr Lys Met Leu Gly Leu Arg Pro Ser Val Asn Arg
145                 150                 155                 160

Leu Met Met Tyr Gln Gln Gly Cys Phe Ala Gly Gly Thr Val Leu Arg
                165                 170                 175

Val Ala Lys Asp Leu Ala Glu Asn Asn Arg Gly Ala Arg Val Leu Val
            180                 185                 190

Val Cys Ser Glu Ile Thr Ala Val Thr Phe Arg Gly Pro Ser Glu Ser
        195                 200                 205

His Leu Asp Ser Met Val Gly Gln Ala Leu Phe Gly Asp Gly Ala Ala
    210                 215                 220

Ala Val Ile Val Gly Ala Asp Pro Asp Glu Arg Val Glu Arg Pro Leu
225                 230                 235                 240

Phe Gln Leu Val Ser Ala Ser Gln Thr Ile Leu Pro Asp Ser Glu Gly
                245                 250                 255

Ala Ile Asp Gly His Leu Arg Glu Val Gly Leu Thr Phe His Leu Leu
            260                 265                 270
```

-continued

```
Lys Asp Val Pro Gly Leu Ile Ser Lys Asn Ile Glu Arg Ser Leu Glu
            275                 280                 285

Glu Ala Phe Lys Pro Leu Gly Ile Thr Asp Tyr Asn Ser Ile Phe Trp
    290                 295                 300

Val Ala His Pro Gly Gly Pro Ala Ile Leu Asp Gln Val Glu Ala Lys
305                 310                 315                 320

Val Gly Leu Glu Lys Glu Arg Met Arg Ala Thr Arg His Val Leu Ser
                325                 330                 335

Glu Tyr Gly Asn Met Ser Ser Ala Cys Val Leu Phe Ile Leu Asp Glu
            340                 345                 350

Met Arg Lys Arg Ser Ala Glu Asp Gly Arg Ala Thr Thr Gly Glu Gly
        355                 360                 365

Phe Glu Trp Gly Val Leu Phe Gly Phe Gly Pro Gly Leu Thr Val Glu
    370                 375                 380

Thr Val Val Leu His Ser Val Pro Ile Thr Thr Gly Ala Ala Ile Thr
385                 390                 395                 400

Ala

<210> SEQ ID NO 8
<211> LENGTH: 398
<212> TYPE: PRT
<213> ORGANISM: Sorghum bicolor

<400> SEQUENCE: 8

Met Thr Thr Gly Lys Val Thr Leu Glu Ala Val Arg Lys Ala Gln Arg
1               5                   10                  15

Ala Glu Gly Pro Ala Thr Val Leu Ala Ile Gly Thr Ala Thr Pro Ala
                20                  25                  30

Asn Cys Val Tyr Gln Ala Asp Tyr Pro Asp Tyr Tyr Phe Arg Val Thr
            35                  40                  45

Lys Ser Glu His Leu Thr Asp Leu Lys Glu Lys Phe Lys Arg Ile Cys
        50                  55                  60

His Lys Ser Met Ile Arg Lys Arg Tyr Met His Leu Thr Glu Asp Ile
65                  70                  75                  80

Leu Glu Glu Asn Pro Asn Met Ser Ser Tyr Trp Ala Pro Ser Leu Asp
                85                  90                  95

Ala Arg Gln Asp Ile Leu Ile Gln Glu Ile Pro Lys Leu Gly Ala Glu
            100                 105                 110

Ala Ala Glu Lys Ala Leu Lys Glu Trp Gly Gln Pro Arg Ser Arg Ile
        115                 120                 125

Thr His Leu Val Phe Cys Thr Thr Ser Gly Val Asp Met Pro Gly Ala
    130                 135                 140

Asp Tyr Gln Leu Ile Lys Leu Leu Gly Leu Cys Pro Ser Val Asn Arg
145                 150                 155                 160

Ala Met Met Tyr His Gln Gly Cys Phe Ala Gly Gly Met Val Leu Arg
                165                 170                 175

Leu Ala Lys Asp Leu Ala Glu Asn Asn Arg Gly Ala Arg Val Leu Ile
            180                 185                 190

Val Cys Ser Glu Ile Thr Val Thr Phe Arg Gly Pro Ser Glu Ser
        195                 200                 205

His Leu Asp Ser Leu Val Gly Gln Ala Leu Phe Gly Asp Gly Ala Ala
    210                 215                 220

Ala Val Ile Val Gly Ala Asp Pro Ser Glu Pro Ala Glu Arg Pro Leu
225                 230                 235                 240
```

```
Phe His Leu Val Ser Ala Ser Gln Thr Ile Leu Pro Asp Ser Glu Gly
                245                 250                 255

Ala Ile Glu Gly His Leu Arg Glu Val Gly Leu Thr Phe His Leu Gln
            260                 265                 270

Asp Arg Val Pro Gln Leu Ile Ser Met Asn Ile Glu Arg Leu Leu Glu
        275                 280                 285

Asp Ala Phe Ala Pro Leu Gly Ile Ser Asp Trp Asn Ser Ile Phe Trp
290                 295                 300

Val Ala His Pro Gly Gly Pro Ala Ile Leu Asn Met Val Glu Ala Lys
305                 310                 315                 320

Val Gly Leu Asp Lys Ala Arg Met Cys Ala Thr Arg His Ile Leu Ala
                325                 330                 335

Glu Tyr Gly Asn Met Ser Ser Val Cys Val Leu Phe Ile Leu Asp Glu
            340                 345                 350

Met Arg Asn Arg Ser Ala Lys Asp Gly His Thr Thr Gly Glu Gly
        355                 360                 365

Met Glu Trp Gly Val Leu Phe Gly Phe Gly Pro Gly Leu Thr Val Glu
370                 375                 380

Thr Ile Val Leu His Ser Val Pro Ile Thr Thr Val Ala Ala
385                 390                 395

<210> SEQ ID NO 9
<211> LENGTH: 404
<212> TYPE: PRT
<213> ORGANISM: Sorghum bicolor

<400> SEQUENCE: 9

Met Gly Ser Ser Ala Ala Pro Ala Asn Val Arg Glu Ile Cys Arg Ala
1               5                   10                  15

Gln Arg Ala Asp Gly Pro Ala Ala Val Leu Ala Ile Gly Thr Ala Asn
            20                  25                  30

Pro Ala Asn Cys Val Pro Gln Asp Glu Phe Pro Asp Phe Tyr Phe Arg
        35                  40                  45

Ala Thr Lys Ser Asp His Leu Thr Gly Leu Lys Glu Lys Phe Lys Arg
    50                  55                  60

Val Cys Gln Lys Leu Gly Val Gln Lys Arg Tyr Leu His Thr Glu
65              70                  75                  80

Glu Leu Leu Ser Ala His Pro Glu Phe Leu Asp His Ser Ser Pro Ser
                85                  90                  95

Leu Asp Ala Arg Leu Asp Ile Val Lys Thr Ala Val Pro Glu Leu Ala
            100                 105                 110

Ala Gln Ala Ser Arg Lys Ala Ile Ala Glu Trp Gly Arg Pro Ala Ala
        115                 120                 125

Asp Ile Thr His Leu Val Val Thr Thr Asn Ser Gly Ala His Ile Pro
130                 135                 140

Gly Val Asp Phe Arg Leu Val Pro Leu Leu Gly Leu Arg Pro Thr Val
145                 150                 155                 160

Arg Arg Thr Met Leu Tyr Leu Asn Gly Cys Phe Ala Gly Ala Ala Ala
                165                 170                 175

Leu Arg Leu Ala Arg Asp Leu Ala Glu Asn Asn Ser Gly Ala Arg Val
            180                 185                 190

Leu Val Val Cys Ala Glu Ile Thr Val Leu Leu Phe Asn Gly Pro Glu
        195                 200                 205

Glu Gly Cys Phe Gln Thr Leu Val Asn Gln Gly Leu Phe Gly Asp Gly
210                 215                 220
```

```
Ala Gly Ala Val Ile Val Gly Ala Asp Pro Leu Ala Glu Arg Pro
225                 230                 235                 240

Leu Phe Glu Ile Val Ser Ala Ala Gln Ala Ile Ile Pro Glu Ser Glu
                245                 250                 255

Asp Val Ile Thr Met His Leu Thr Arg Gly Gly Tyr Gly Gly Asn Ile
            260                 265                 270

Ser Thr Arg Gln Val Pro Val Leu Ile Gly Asp Asn Ile Glu Arg Cys
        275                 280                 285

Leu Thr Asp Ala Phe Ala Pro Leu Gly Gly Val Ile Gly Ala Glu Trp
    290                 295                 300

Asn Asp Leu Phe Trp Asp Val His Pro Gly Ser Ser Ala Ile Leu Asp
305                 310                 315                 320

Gln Val Asp Ala Val Leu Lys Leu Lys Pro Glu Lys Leu Ala Ala Ser
                325                 330                 335

Arg Arg Val Leu Ser Glu Tyr Gly Asn Met Phe Gly Val Thr Val Ile
            340                 345                 350

Phe Val Leu Asp Glu Leu Arg Arg Arg Met Glu Lys Gly Glu Glu
        355                 360                 365

Gly Ala Pro Glu Trp Gly Val Met Val Ala Phe Gly Pro Gly Leu Thr
    370                 375                 380

Val Glu Thr Met Val Leu His Arg Ser Gly Thr Pro Ala Glu Lys Lys
385                 390                 395                 400

Leu Ala Glu Ala

<210> SEQ ID NO 10
<211> LENGTH: 398
<212> TYPE: PRT
<213> ORGANISM: Oryza sativa

<400> SEQUENCE: 10

Met Ala Ala Ala Val Thr Val Glu Glu Val Arg Arg Ala Gln Arg Ala
1               5                   10                  15

Glu Gly Pro Ala Thr Val Leu Ala Ile Gly Thr Ala Thr Pro Ala Asn
                20                  25                  30

Cys Val Tyr Gln Ala Asp Tyr Pro Asp Tyr Tyr Phe Arg Ile Thr Lys
            35                  40                  45

Ser Glu His Met Val Glu Leu Lys Glu Lys Phe Lys Arg Met Cys Asp
    50                  55                  60

Lys Ser Gln Ile Arg Lys Arg Tyr Met His Leu Thr Glu Glu Ile Leu
65                  70                  75                  80

Gln Glu Asn Pro Asn Met Cys Ala Tyr Met Ala Pro Ser Leu Asp Ala
                85                  90                  95

Arg Gln Asp Ile Val Val Val Glu Val Pro Lys Leu Gly Lys Ala Ala
            100                 105                 110

Ala Gln Lys Ala Ile Lys Glu Trp Gly Gln Pro Arg Ser Arg Ile Thr
    115                 120                 125

His Leu Val Phe Cys Thr Thr Ser Gly Val Asp Met Pro Gly Ala Asp
130                 135                 140

Tyr Gln Leu Ala Lys Met Leu Gly Leu Arg Pro Asn Val Asn Arg Leu
145                 150                 155                 160

Met Met Tyr Gln Gln Gly Cys Phe Ala Gly Gly Thr Val Leu Arg Val
                165                 170                 175

Ala Lys Asp Leu Ala Glu Asn Asn Arg Gly Ala Arg Val Leu Ala Val
            180                 185                 190
```

```
Cys Ser Glu Ile Thr Ala Val Thr Phe Arg Gly Pro Ser Glu Ser His
            195                 200                 205

Leu Asp Ser Met Val Gly Gln Ala Leu Phe Gly Asp Gly Ala Ala Ala
    210                 215                 220

Val Ile Val Gly Ser Asp Pro Asp Glu Ala Val Glu Arg Pro Leu Phe
225                 230                 235                 240

Gln Met Val Ser Ala Ser Gln Thr Ile Leu Pro Asp Ser Glu Gly Ala
                245                 250                 255

Ile Asp Gly His Leu Arg Glu Val Gly Leu Thr Phe His Leu Leu Lys
            260                 265                 270

Asp Val Pro Gly Leu Ile Ser Lys Asn Ile Glu Arg Ala Leu Gly Asp
        275                 280                 285

Ala Phe Thr Pro Leu Gly Ile Ser Asp Trp Asn Ser Ile Phe Trp Val
    290                 295                 300

Ala His Pro Gly Gly Pro Ala Ile Leu Asp Gln Val Glu Ala Lys Val
305                 310                 315                 320

Gly Leu Asp Lys Glu Arg Met Arg Ala Thr Arg His Val Leu Ser Glu
                325                 330                 335

Tyr Gly Asn Met Ser Ser Ala Cys Val Leu Phe Ile Leu Asp Glu Met
            340                 345                 350

Arg Lys Arg Ser Ala Glu Asp Gly His Ala Thr Thr Gly Glu Gly Met
        355                 360                 365

Asp Trp Gly Val Leu Phe Gly Phe Gly Pro Gly Leu Thr Val Glu Thr
    370                 375                 380

Val Val Leu His Ser Val Pro Ile Thr Ala Gly Ala Ala Ala
385                 390                 395

<210> SEQ ID NO 11
<211> LENGTH: 392
<212> TYPE: PRT
<213> ORGANISM: Oryza sativa

<400> SEQUENCE: 11

Met Pro Gly Thr Ala Thr Ala Ala Val Val Asp Ser Arg Pro Cys Thr
1               5                   10                  15

Gln His Ala Glu Gly Pro Ala Ala Val Leu Ala Ile Gly Thr Ala Asn
                20                  25                  30

Pro Thr Asn Ile Val Tyr Gln Asp Gly Phe Thr Asp Tyr Tyr Phe Gly
            35                  40                  45

Leu Thr Glu Ser Glu His Leu Thr Glu Leu Lys Asp Lys Met Lys Arg
    50                  55                  60

Ile Cys His Arg Ser Gly Ile Glu Lys Arg Tyr Ile His Leu Asp Glu
65                  70                  75                  80

Lys Leu Ile Arg Glu His Pro Glu Ile Ile Asp Lys His Met Pro Ser
                85                  90                  95

Leu Glu Thr Arg Val Asp Ile Val Thr Thr Glu Ile Pro Lys Leu Ala
            100                 105                 110

Glu Ser Ala Ala Arg Lys Ala Ile Ala Glu Trp Gly Arg Pro Ala Ile
        115                 120                 125

Asp Ile Thr His Leu Ile Phe Ser Thr Tyr Ser Gly Cys Ser Ala Pro
    130                 135                 140

Ser Ala Asp Leu Lys Leu Ala Ser Leu Leu Gly Leu Asn Pro Ser Val
145                 150                 155                 160

Ser Arg Thr Ile Leu Ser Leu His Gly Cys Ser Gly Gly Gly Arg Ala
                165                 170                 175
```

-continued

Leu Gln Leu Ala Lys Glu Leu Ala Glu Asn Asn Arg Asp Ala Arg Val
            180                 185                 190

Leu Ile Ala Cys Ala Glu Leu Thr Leu Ile Cys Phe Ser Asn Pro Asp
        195                 200                 205

Glu Ser Lys Ile Val Gly His Gly Leu Phe Gly Asp Gly Ala Gly Ala
    210                 215                 220

Ile Ile Val Gly Ala Asp Pro Leu Val Asp Gly Glu Arg Pro Leu Phe
225                 230                 235                 240

Glu Met Val Leu Ala Ser Gln Thr Thr Ile Pro Gly Thr Glu His Ala
                245                 250                 255

Leu Gly Met Gln Thr Thr Ser Asn Gly Ile Asp Phe His Leu Ser Ile
            260                 265                 270

Gln Val Pro Thr Leu Ile Lys Asp Asn Ile Arg Gln Cys Leu Leu Asn
        275                 280                 285

Thr Phe Arg Ser Val Gly Asn Met Asp Pro Asn Trp Asn Asp Leu Phe
290                 295                 300

Trp Ala Val His Pro Gly Gly Arg Ala Ile Leu Asp Asn Ile Glu Gly
305                 310                 315                 320

Glu Leu Gln Leu Gln Pro Ala Lys Leu Ala Ala Ser Arg His Val Leu
                325                 330                 335

Ser Glu Tyr Gly Asn Met Ser Gly Thr Thr Ile Ala Phe Val Leu Asp
            340                 345                 350

Glu Leu Arg Cys Arg Arg Glu Lys Gly Asp Glu His Gln Gln Pro
        355                 360                 365

Glu Trp Gly Val Met Leu Ala Phe Gly Pro Gly Ile Thr Ile Glu Ala
370                 375                 380

Met Val Leu Arg Asn Pro Leu Ser
385                 390

<210> SEQ ID NO 12
<211> LENGTH: 399
<212> TYPE: PRT
<213> ORGANISM: Oryza sativa

<400> SEQUENCE: 12

Met Pro Gly Ala Ala Thr Thr Ala Ala Val Val Asp Ser Arg Arg Ser
1               5                   10                  15

Ala Gln Arg Ala Glu Gly Pro Ala Thr Ile Ile Ala Ile Gly Thr Ala
            20                  25                  30

Asn Pro Ala Asn Ile Val Pro Gln Asp Asn Phe Ala Asp Tyr Tyr Phe
        35                  40                  45

Gly Leu Thr Lys Ser Glu His Leu Thr Glu Leu Lys Asp Lys Met Lys
    50                  55                  60

Arg Ile Cys Lys Lys Ser Gly Ile Glu Lys Tyr Ile His Leu Asp
65                  70                  75                  80

Glu Glu Ile Ile Arg Ala His Pro Glu Ile Ile Asp Lys His Gln Pro
                85                  90                  95

Ser Leu Glu Ala Arg Val Glu Ile Ala Ala Glu Val Pro Lys Leu
            100                 105                 110

Ala Glu Ser Ala Ala Arg Lys Ala Ile Ala Lys Trp Gly Arg Pro Ala
        115                 120                 125

Thr Asp Ile Thr His Leu Ile Phe Ser Thr Tyr Ser Gly Cys Arg Ala
    130                 135                 140

Pro Ser Ala Asp Leu Gln Leu Ala Ser Leu Leu Gly Leu Arg Pro Ser
145                 150                 155                 160

Val Ser Arg Thr Ile Leu Ser Leu His Gly Cys Ser Gly Gly Arg
165                170                175

Ala Leu Gln Leu Ala Lys Glu Leu Ala Glu Asn Asn Arg Gly Ala Arg
    180                185                190

Val Leu Val Ala Leu Ser Glu Leu Thr Leu Val Cys Phe Ser Thr Pro
        195                200                205

Asp Glu Ser Lys Ile Val Gly His Gly Leu Phe Gly Asp Gly Ala Gly
    210                215                220

Ala Ile Ile Val Gly Ala Gly Pro Phe Ser Asp Gly Glu Cys Pro Leu
225                230                235                240

Phe Glu Met Val Ala Ala Ser Gln Thr Met Ile Pro Gly Thr Glu His
            245                250                255

Ala Leu Gly Met Gln Ala Thr Ser Thr Gly Ile Asp Phe His Leu Ser
        260                265                270

Val Gln Val Pro Met Leu Ile Lys Asp Asn Ile Gln Gln Ser Leu Leu
    275                280                285

Glu Ser Phe Gln Ser Val Gly Tyr Thr Asp Pro Asp Trp Asn Asn Leu
    290                295                300

Phe Trp Ala Val His Pro Gly Gly Arg Ala Ile Leu Asp Asn Ile Glu
305                310                315                320

Gly Lys Leu Gln Leu Gln Pro Trp Lys Leu Ala Ala Ser Arg Gln Val
            325                330                335

Leu Arg Glu Phe Gly Asn Met Ser Gly Ala Thr Ile Ala Phe Val Leu
        340                345                350

Asp Glu Leu Cys His Arg Arg Glu Lys Asp Glu Asp Glu Ser Gln Gln
    355                360                365

His Glu Trp Gly Val Met Leu Ala Phe Gly Pro Gly Ile Thr Ile Glu
    370                375                380

Thr Ile Val Met Arg Asn Pro Leu Ala Arg Gly Leu Lys Gln Asn
385                390                395

<210> SEQ ID NO 13
<211> LENGTH: 398
<212> TYPE: PRT
<213> ORGANISM: Oryza sativa

<400> SEQUENCE: 13

Met Pro Gly Ala Thr Thr Ala Ala Ile Val Asp Ser Arg Arg Gly Thr
1               5                   10                  15

Gln His Ser Glu Gly Pro Ala Thr Ile Leu Ala Ile Gly Thr Ala Asn
            20                  25                  30

Pro Glu Asn Ile Met Phe Gln Asp Asn Phe Ala Asp Tyr Tyr Phe Gly
        35                  40                  45

Leu Thr Lys Ser Glu His Leu Thr Glu Leu Lys Glu Lys Met Lys Arg
50                  55                  60

Ile Cys His Lys Ser Gly Ile Glu Lys Arg Tyr Ile His Leu Asp Ala
65                  70                  75                  80

Glu Leu Ile Ser Val His Pro Glu Ile Ile Asp Lys His Leu Pro Ser
            85                  90                  95

Leu Glu Thr Arg Val Asp Ile Val Ala Thr Glu Val Pro Lys Leu Ala
        100                 105                 110

Glu Ser Ala Ala Arg Lys Ala Ile Ala Glu Trp Gly Arg Pro Ala Thr
    115                 120                 125

Asp Ile Thr His Leu Ile Phe Ser Thr Tyr Ser Gly Cys Arg Ala Pro
130                 135                 140

Ser Ala Asp Leu Gln Leu Ala Ser Leu Leu Gly Leu Arg Pro Ser Val
145                 150                 155                 160

Ser Arg Thr Ile Leu Ser Leu His Gly Cys Ser Gly Gly Arg Ala
            165                 170                 175

Leu Gln Leu Ala Lys Glu Ile Ala Glu Asn Asn Arg Gly Ala Arg Val
            180                 185                 190

Leu Ile Ala Cys Ser Glu Leu Thr Leu Ile Cys Phe Ser Thr Pro Asp
            195                 200                 205

Glu Ser Lys Ile Ile Gly His Gly Leu Phe Gly Asp Gly Ala Gly Ala
            210                 215                 220

Val Ile Val Gly Ala Asp Pro Ser Val Asp Gly Glu Cys Pro Leu Phe
225                 230                 235                 240

Glu Met Val Ala Ala Ser Gln Thr Met Ile Pro Gly Thr Glu His Ala
            245                 250                 255

Leu Gly Met Gln Ala Thr Ser Ser Gly Ile Asp Phe His Leu Ser Ile
            260                 265                 270

Gln Val Pro Thr Leu Ile Lys Asp Asn Ile His Gln Cys Leu Leu Asn
            275                 280                 285

Ala Phe Arg Ser Val Gly Asn Thr Asp Pro Asn Trp Asn Asp Leu Phe
290                 295                 300

Trp Ala Val His Pro Gly Gly Arg Ala Ile Leu Asp Asn Ile Glu Asp
305                 310                 315                 320

Lys Leu Gln Leu His Pro Cys Lys Leu Ala Ala Ser Arg Gln Val Leu
            325                 330                 335

Ser Glu Tyr Gly Asn Met Ser Gly Ala Thr Ile Ala Phe Val Leu Asp
            340                 345                 350

Glu Leu Arg Arg Arg Arg Glu Lys Gln Asp Ile Gln Gln Pro
            355                 360                 365

Glu Trp Gly Val Leu Leu Ala Phe Gly Pro Gly Val Thr Ile Glu Ser
            370                 375                 380

Ile Val Leu Arg Asn Pro Leu Ser Arg Gly Leu Lys Glu Asn
385                 390                 395

<210> SEQ ID NO 14
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 14
ggctcgaaga cgatcagata cc                                             22

<210> SEQ ID NO 15
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 15
tcggcatcgt ttatggtt                                                  18

<210> SEQ ID NO 16
<211> LENGTH: 22
<212> TYPE: DNA
<213> ORGANISM: Artificial Sequence
<220> FEATURE:
<223> OTHER INFORMATION: Chemically Synthesized

```
<400> SEQUENCE: 16
ataaacccgc catagaagtt gc                                          22

<210> SEQ ID NO 17
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 17
ttagccacaa ggagctcatt ttac                                        24

<210> SEQ ID NO 18
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 18
ccctggctaa aataaggtcc ac                                          22

<210> SEQ ID NO 19
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 19
ccttatggtc catgaattgg c                                           21

<210> SEQ ID NO 20
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 20
ctggcggagg catgagac                                               18

<210> SEQ ID NO 21
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 21
tgcaatcctg atccaagttc c                                           21

<210> SEQ ID NO 22
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 22
cgctcggtct ccatgaatc                                              19
```

-continued

<210> SEQ ID NO 23
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 23
aacgatcgac gactggtgg                                                  19

<210> SEQ ID NO 24
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 24
gaatgctcca gacatggtag acag                                            24

<210> SEQ ID NO 25
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 25
ttgtcatgta atggactcta gacagg                                          26

<210> SEQ ID NO 26
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 26
catatgggga gcgcaccgc                                                  19

<210> SEQ ID NO 27
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 27
ggatcctcaa tttccctcca gttccaggt                                       29

<210> SEQ ID NO 28
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 28
catatggggt ccatggggaa gg                                              22

<210> SEQ ID NO 29
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 29
ggatcctcaa tttccctcca gttccgg    27

<210> SEQ ID NO 30
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 30
catatgggaa agtagtgctg ctccg    25

<210> SEQ ID NO 31
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 31
ggatcctcaa tgcctccgcc agtttc    26

<210> SEQ ID NO 32
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 32
atatcatatg cctggaacag ctactgc    27

<210> SEQ ID NO 33
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 33
atatagatct tcatgagagt gggttacgca ac    32

<210> SEQ ID NO 34
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 34
atatcatatg cctggagcag ctaccac    27

<210> SEQ ID NO 35
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 35
atatagatct ctaattttgc ttaagaccac gtg    33

```
<210> SEQ ID NO 36
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 36
atatcatatg cctggagcaa ctacccg                                        27

<210> SEQ ID NO 37
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 37
atatagatct ttaattttcc ttcaaaccac gtg                                 33

<210> SEQ ID NO 38
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 38
gagtttggca acatgagtgg c                                              21

<210> SEQ ID NO 39
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 39
tcatcgagca cgaagatcac c                                              21

<210> SEQ ID NO 40
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 40
ggctcgaaga cgatcagata cc                                             22

<210> SEQ ID NO 41
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 41
tcggcatcgt ttatggtt                                                  18

<210> SEQ ID NO 42
<211> LENGTH: 26
<212> TYPE: DNA
<213> ORGANISM: Artificial Sequence
<220> FEATURE:
<223> OTHER INFORMATION: Chemically Synthesized
```

```
<400> SEQUENCE: 42
ccctgaattc agaccacgat accgga                                    26

<210> SEQ ID NO 43
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 43
ctctggatcc ttacgcaccg ccttat                                    26

<210> SEQ ID NO 44
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 44
ccctgaattc gaccacgata ccgga                                     25

<210> SEQ ID NO 45
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 45
ccccggatcc accttatggt ccat                                      24

<210> SEQ ID NO 46
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 46
cccttgtaca gaccacgata ccgga                                     25

<210> SEQ ID NO 47
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 47
ctctacgcgt tacgcaccgc cttat                                     25

<210> SEQ ID NO 48
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 48
cctctgtaca gaccacgata ccgga                                     25
```

```
<210> SEQ ID NO 49
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 49
ctctacgcgt ccaccttatg gtccat                                        26

<210> SEQ ID NO 50
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 50
cgcatatctc attaaagcag ggtc                                          24

<210> SEQ ID NO 51
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 51
ctccttgtgg ctaattcatg gac                                           23

<210> SEQ ID NO 52
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 52
cacatatatc gccaattcat ggac                                          24

<210> SEQ ID NO 53
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 53
agctccttgt ggctaattca tgg                                           23

<210> SEQ ID NO 54
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 54
tataggcaca aatacaatat aacacacttg c                                  31

<210> SEQ ID NO 55
<211> LENGTH: 18
<212> TYPE: DNA
<213> ORGANISM: Artificial Sequence
<220> FEATURE:
<223> OTHER INFORMATION: Chemically Synthesized
```

<400> SEQUENCE: 55
atggggtcca tggggaag                                                       18

<210> SEQ ID NO 56
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 56
ggtggccggt agtgcct                                                        17

<210> SEQ ID NO 57
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 57
ccagtagctc ctgctctgtg aa                                                  22

<210> SEQ ID NO 58
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 58
tgcagaaaac caaaagcaaa ag                                                  22

<210> SEQ ID NO 59
<211> LENGTH: 1179
<212> TYPE: DNA
<213> ORGANISM: Oryza sativa

<400> SEQUENCE: 59
atgcctggaa cagctactgc cgctgttgtt gacagccgcc cgtgcacaca gcacgcggaa        60
ggccctgctg cggtcctcgc catcggcact gcaaacccca caaatatcgt ctatcaagat       120
gggtttaccg actactactt cggtctaacc gagagcgagc atcttactga gctgaaggac       180
aaaatgaaga gaatatgtca caggtcagga atagagaaac gctacatcca ccttgatgaa       240
aagctcatcc gtgagcaccc ggagatcatc gacaaacaca tgccctccct tgaaactcgt       300
gtagacatcg tcaccactga gatcccaaag ctcgctgagt ccgccgcacg gaaggccatc       360
gccgagtggg gccgtcctgc cattgatatt acccacctca tcttcagcac ctactccggg       420
tgcagtgctc ctagcgctga cctcaagctg gcatcactac tcgggctcaa cccttctgtc       480
tctcgcacca tcctcagcct ccacggttgc tctggaggcg gtagggccct ccaacttgcc       540
aaggagcttg ccgagaacaa ccgcgatgca cgcgttctca tagcctgcgc cgagctgacg       600
ctgatatgct tctcaaaccc agatgaaagc aaaatcgtcg ccatggacta tttggggat       660
ggtgccggag caatcattgt cggcgctgac ccattggtcg atgagaacg cccgctgttt       720
gagatggtcc ttgcctcgca acaacgata ccaggtactg agcatgcact ggcatgcag       780
accaccagca atggcataga tttccacctc tctatccagg tgccgacgct aatcaaggac       840
aacatccgac aatgcttgct caacacattc gatcggttg aaacatgga tcctaattgg       900
aatgacctct tctgggcggt gcaccctggt ggccgtgcaa tccttgacaa catagaaggt       960

```
gagcttcagc tgcaaccagc aaagcttgcg gcaagccgcc atgtgcttag cgagtacggg    1020
aatatgagtg gcacgacgat cgcgtttgtt cttgatgagt tgcgttgtcg tcgggagaag    1080
gaaggagatg agcatcaaca acctgagtgg ggagtaatgc tagcctttgg accaggtatc    1140
acaatagagg caatggtgtt gcgtaaccca ctctcatga                            1179
```

<210> SEQ ID NO 60
<211> LENGTH: 1200
<212> TYPE: DNA
<213> ORGANISM: Oryza sativa

<400> SEQUENCE: 60

```
atgcctggag cagctaccac cgccgccgtt gttgacagcc gccgtagcgc acagcgcgcg      60 gaaggcccg ccaccatcat cgccatcggc actgcaaacc cagctaatat tgttcctcag     120
gataactttg ccgactacta cttcggccta accaagagcg agcatcttac tgaacttaag    180
gacaagatga gaggatatg taaaaaatca ggcatagaga agcgatacat ccaccttgat    240
gaggagatca tccgtgccca tccagagatc attgacaaac accagccctc ccttgaagct    300
cgtgttgaaa tcgccgccgc cgaggtccca aagctcgccg agtctgctgc aaggaaggcc    360
attgccaagt ggggccgtcc agccaccgac attacccacc tcatcttcag cacctactct    420
ggatgtcgtg cccctagcgc tgacctccag ctggcatcgc tccttggcct ccgtccttct    480
gtctcccgca caatcctcag cctccacggc tgctctggcg gtggcagggc gctccaactc    540
gccaaggagc ttgctgagaa caaccgtggt gcacgcgtcc ttgtagcact ctcagagcta    600
accctggtat gtttctccac cccagacgaa agcaaaattg tcggacatgg actgtttggg    660
gatggtgccg gtgcaataat cgttggcgca ggcccgtttt ctgatggcga gtgcccgttg    720
ttcgagatgg ttgctgcctc acagaccatg ataccaggaa ccgagcacgc acttggcatg    780
caggccacta gcaccggcat agatttccac ctctctgtcc aggtgccaat gctgatcaag    840
gataacatcc agcagagctt gctcgaatcc ttccaatcgg tcggatacac agatcctgac    900
tggaacaatc tcttctgggc ggtgcacccc ggcggccgtg ctatccttga acatagag     960 ggcaagctac agttgcaacc atggaagctt gcagcaagcc ggcaagtgct acgcgagttt    1020
gggaacatga gtggtgcaac tattgcattc gttcttgatg aactatgcca ccgtcgggag    1080
aaggacgaag atgagtcaca gcagcatgaa tggggagtga tgctggcctt tggaccaggg    1140
atcacaattg agacaattgt tatgcgcaac ccattggcac gtggtcttaa gcaaaattag    1200
```

<210> SEQ ID NO 61
<211> LENGTH: 1197
<212> TYPE: DNA
<213> ORGANISM: Oryza sativa

<400> SEQUENCE: 61

```
atgcctggag caactaccgc cgctattgtt gacagccgcc gcggcacaca acattcggaa      60
ggtcctgcaa cgatcctcgc catcggcact gcaaacccgg aaaacatcat gtttcaggat    120
aactttgccg actactactt tggtctaacc aaaagcgagc accttaccga gctcaaggaa    180
aagatgaaga ggatatgtca taaatctggt atagaaaagc gctacatcca ccttgacgca    240
gagcttatca gtgtccaccc agagatcatt gacaaacatt gccctccct tgaaactcgt     300 gtagacatcg tggctactga ggtccccaag cttgctgagt ccgctgcgcg gaaagccatt    360
gctgagtggg gccgtccggc cactgacatc actcacctta tcttcagcac ctactcaggc    420
tgtcgtgcac ctagtgccga cctccaattg gcttcgttgc tcggactacg cccttccgtt    480
```

-continued

```
tctcgcacca ttctcagtct ccacggttgc tcaggtggtg gcagggcact ccaactcgca        540
aaggagatcg ccgagaataa ccgcggtgct cgtgtcctca tagcttgctc cgagctgaca        600
ctgatatgct tctctacccc agacgaaagc aaaatcattg gccatggact gttcggggat        660
ggtgctggcg cagtcatcgt cggtgccgat ccctcagtcg atggtgagtg cccgctattc        720
gagatggttg ccgcctcaca aaccatgata ccaggaaccg agcacgcgct cggcatgcag        780
gccactagta gtggaataga ttttcacctc tccatccagg tgccgacact gataaaggac        840
aacatccatc agtgcttgct caatgcgttt cgatctgttg gaaacacaga tcctaactgg        900
aacgacctct tctgggcagt gcaccctggc ggtcgcgcaa tccttgataa catagaagac        960
aagctccaac tgcatccatg taagcttgcg gcaagccgcc aagtgttgag cgagtacggg       1020
aacatgagtg gtgcaacaat tgcattcgtt cttgatgaac tacggcgccg tcgggagaag       1080
gaacaagaca tacagcaaca acctgagtgg ggagtgttgc tggcctttgg acctggagtc       1140
acaatagagt caatcgtgct gcgtaaccca ctctcacgtg gtttgaagga aaattaa         1197
```